United States Patent
Waxman et al.

(10) Patent No.: US 11,485,763 B2
(45) Date of Patent: Nov. 1, 2022

(54) CELL-BASED ASSAY FOR DETERMINING MTOR ACTIVITY

(71) Applicant: Medical Diagnostic Laboratories, L.L.C., Hamilton, NJ (US)

(72) Inventors: Elisa A Waxman, Philadelphia, PA (US); Thais Acquafreda, Philadelphia, PA (US)

(73) Assignee: Medical Diagnostics Laboratories, LLC, Hamilton, NJ (US)

( * ) Notice: Subject to any disclaimer, the term of this patent is extended or adjusted under 35 U.S.C. 154(b) by 750 days.

(21) Appl. No.: 16/413,658

(22) Filed: May 16, 2019

(65) Prior Publication Data

US 2019/0263875 A1  Aug. 29, 2019

Related U.S. Application Data

(62) Division of application No. 15/430,153, filed on Feb. 10, 2017, now Pat. No. 10,351,609.

(60) Provisional application No. 62/432,935, filed on Dec. 12, 2016.

(51) Int. Cl.
| | | |
|---|---|---|
| *C12Q 1/68* | (2018.01) | |
| *C07K 14/47* | (2006.01) | |
| *C12N 9/02* | (2006.01) | |
| *G01N 33/50* | (2006.01) | |

(52) U.S. Cl.
CPC ...... *C07K 14/4703* (2013.01); *C07K 14/4701* (2013.01); *C07K 14/4705* (2013.01); *C12N 9/0069* (2013.01); *C12Y 113/12007* (2013.01); *C12Y 207/11001* (2013.01); *G01N 33/5011* (2013.01); *C07K 2319/60* (2013.01); *G01N 2333/91215* (2013.01); *G01N 2800/52* (2013.01)

(58) Field of Classification Search
CPC ............ C07K 14/4703; C07K 14/4701; C07K 14/4705; C07K 2319/60; C12N 9/0069; C12Y 113/12007; C12Y 207/11001; G01N 33/5011; G01N 2333/91215; G01N 2800/52
See application file for complete search history.

(56) References Cited

U.S. PATENT DOCUMENTS

| | | | | |
|---|---|---|---|---|
| 2010/0144805 A1* | 6/2010 | Wagner | .................... | A61P 35/04 |
| | | | | 435/7.1 |
| 2013/0123328 A1* | 5/2013 | Yu | ..................... | G01N 33/57407 |
| | | | | 435/375 |
| 2014/0157443 A1* | 6/2014 | Grosveld | ........... | A61K 31/5377 |
| | | | | 424/139.1 |
| 2014/0378500 A1* | 12/2014 | Cohen | ................. | A61K 31/436 |
| | | | | 514/291 |
| 2018/0055816 A1* | 3/2018 | Thorson | ............... | A61K 31/665 |

OTHER PUBLICATIONS

Dixon et al. "NanoLuc Complementation Reporter Optimized for Accurate Measurement of Protein Interactions in Cells." (ACS Chem Biol Feb. 19, 2016; vol. 11, No. 2: pp. 400-408, published Nov. 16, 2015). (Year: 2015).*
Sekiyama etal (PNAS published online Jul. 13, 2015, pp. E4036-E4045). (Year: 2015).*
Kunz J. Target of rapamycin in yeast, TOR2, is an essential phosphatidylinositol kinase homolog required for G1 progression. Cell 1993; 73:585-96.
Kuruvilla FG. The PIK-related kinases intercept conventional signaling pathways. Cell Biol 1999; 6:R129-36.
Graves LM. cAMP- and rapamycin-sensitive regulation of the association of eurkaryotic initiation factor 4E and the translational regulator PHAS-I in aortic smooth muscle cells. Proc Natl Acad Sci USA 1995; 92:7222-6.
Haghighat A. Repression of cap-dependent translation by 4E-binding protein 1: competition with p220 for binding to eurkaryotic initiation factor-4E. EMBO J 1995; 14:5701-9.
Beretta L Rapamycin blocks the phosphorylation of 4E-BP1 and inhibits cap-dependent initiation of translation. EMBO J 1996; 15:658-64.
Murakami M. mTOR is essential for growth and proliferation in early mouse embryos and embryonic stem cells. Mol Cell Biol 2004; 24:6710-8.
Zhang H. Regulation of cellular growth by the *Drosophila* target of rapamycin dTOR. Genes Dev 2000; 14:2712-24.
Brown EJ. A mammalian protein targeted by G1-arresting rapamycin-receptor complex. Nature 1994; 369:756-8.
Grabiner BC. A diverse array of cancer-associated MTOR mutations are hyperactivating and can predict rapamycin sensitivity. Cancer Discov 2014; 4:554-63.
Wagle N. Response and acquired resistance to everolimus in anaplastic thyroid cancer. N Engl J Med 2014; 371:1426-33.
Luker KE. Kinetics of regulated protein-protein interactions revealed with firefly luciferase complementation imaging in cells and living animals. Proc Natl Acad Sci USA 2004; 101:12288-93.
Dixon AS. NanoLuc Complementation Reporter Optimized for Accurate Measurement of Protein Interactions in Cells. ACS Chem Biol 2016; 11:400-8.
Thoreen CC. An ATP-competitive mammalian target of rapamycin inhibitor reveals rapamycin-resistant functions of mTORC1. J Biol Chem 2009;284:8023-32.
Schenone S. ATP-competitive inhibitors of mTOR: an update. Curr Med Chem 2011; 18:2995-3014.
Wu TJ. Identification of a Non-Gatekeeper Hot Spot for Drug-Resistant Mutations in mTOR Kinase. Cell Rep 2015; 11:446-59.

(Continued)

*Primary Examiner* — Catherine S Hibbert
(74) *Attorney, Agent, or Firm* — Arnold Braun; Terence J. Bogie; Jessica Downing

(57) ABSTRACT

Disclosed are methods of determining activity of mTOR variants upon exposure to mTOR inhibitors, such a rapamycin or rapalogs thereof, methods for determining kinase activity of a mTOR variant, and methods for determining tumor cell response to treatment with rapamycin or rapalogs thereof. A method for determining whether a compound inhibits mTOR activity in a cell is also disclosed.

24 Claims, 25 Drawing Sheets

Specification includes a Sequence Listing.

(56) References Cited

OTHER PUBLICATIONS

Rodrik-Outmezguine VS. Overcoming mTOR resistance mutations with a new-generation mTOR inhibitor. Nature 2016; 534:272-6.
Marcotrigiano J. Cap-dependent translation initiation in eukaryotes is regulated by a molecular mimic of eIF4G. Mol Cell 1999; 3:707-16.
Edwards SR. The rapamycin-binding domain of the protein kinase mammalian target of rapamycin is a destabilizing domain. J Biol Chem 2007; 282:13395-401.
Sedrani R. Chemical modification of rapamycin: the discovery of SDZ RAD. Transplant Proc 1998; 30:2192-4.
Iiboshi Y. Amino acid-dependent control of p70(s6k). Involvement of tRNA aminoacylation in the regulation. J Biol Chem 1999; 274:1092-9.
Guichard SM. AZD2014, an Inhibitor of mTORC1 and mTORC2, Is Highly Effective in ER+ Breast Cancer When Administered Using Intermittent or Continuous Schedules. Mol Cancer Ther 2015; 14:2508-18.
Hsieh AC. The translational landscape of mTOR signalling [sic] steers cancer initiation and metastasis. Nature 2012; 485:55-61.
Waxman EA. A novel, high-efficiency cellular model of fibrillar alpha-synuclein inclusions and the examination of mutations that inhibit amyloid formation. J Neurochem 2010; 113:374-388.
Sekiyama et al., PNAS published online Jul. 13, 2015, pp. E4036-E4045.
Non-confidential Slide Deck distributed to Dr. Maria Dahl of AstraZeneca, Jan. 22, 2017.

\* cited by examiner

Figure 2A

ATGGTGACCGGCTACCGGCTGTTCGAGGAGATTCTCGGGAGTTCCGGTGGTGGCGGGAGCGGAGGTGGAGGCTC
GAGCGGTATGGCGACTGTCGAACCGGAAACCACCCCTACTCCTAATCCCCCGACTACAGAAGAGGAGAAAACGGA
ATCTAATCAGGAGGTTGCTAACCCAGAACACTATATTAAACATCCCCTACAGAACAGATGGGCACTCTGGTTTTTA
AAAATGATAAAAGCAAAACTTGGCAAGCAAACCTGCGGCTGATCTCCAAGTTTGATACTGTTGAAGACTTTTGGGC
TCTGTACAACCATATCCAGTTGTCTAGTAATTTAATGCCTGGCTGTGACTACTCACTTTTTAAGGATGGTATTGAGC
CTATGTGGGAAGATGAGAAAAACAAACGGGGGGGACGATGGCTAATTACATTGAACAAACAGCAGAGACGAAG
TGACCTCGATCGCTTTTGGCTAGAGACACTTCTGTGCCTTATTGGAGAATCTTTTGATGACTACAGTGATGATGTAT
GTGGCGCTGTTGTTAATGTTAGAGCTAAAGGTGATAAGATAGCAATATGGACTACTGAATGTGAAAACAGAGAAG
CTGTTACACATATAGGGAGGGTATACAAGGAAAGGTTAGGACTTCCTCCAAAGATAGTGATTGGTTATCAGTCCC
ACGCAGACACAGCTACTAAGAGCGGCTCCACCACTAAAAATAGGTTTGTTGTTTAA

Figure 2B

ATGGTCTTCACACTCGAAGATTTCGTTGGGGACTGGGAACAGACAGCCGCCTACAACCTGGACCAAGTCCTTGAA
CAGGGAGGTGTGTCCAGTTTGCTGCAGAATCTCGCCGTGTCCGTAACTCCGATCCAAAGGATTGTCCGGAGCGGT
GAAAATGCCCTGAAGATCGACATCCATGTCATCATCCCGTATGAAGGTCTGAGCGCCGACCAAATGGCCCAGATC
GAAGAGGTGTTTAAGGTGGTGTACCCTGTGGATGATCATCACTTTAAGGTGATCCTGCCCTATGGCACACTGGTAA
TCGACGGGGTTACGCCGAACATGCTGAACTATTTCGGACGGCCGTATGAAGGCATCGCCGTGTTCGACGGCAAAA
AGATCACTGTAACAGGGACCCTGTGGAACGGCAACAAAATTATCGACGAGCGCCTGATCACCCCCGACGGCTCCA
TGCTGTTCCGAGTAACCATCAACAGTGGGAGTTCCGGTGGTGGCGGGAGCGGAGGTGGAGGCTCGAGCGGTATG
TCCGGGGGCAGCAGCTGCAGCCAGACCCCAAGCCGGGCCATCCCCGCCACTCGCCGGGTGGTGCTCGGCGACGG
CGTGCAGCTCCCGCCCGGGGACTACAGCACGACCCCGGCGGCACGCTCTTCAGCACCACCCCGGGAGGTACCAG
GATCATCTATGACCGGAAATTCCTGATGGAGTGTCGGAACTCACCTGTGACCAAAACACCCCCAAGGGATCTGCCC
ACCATTCCGGGGGTCACCAGCCCTTCCAGTGATGAGCCCCCCATGGAAGCCAGCCAGAGCCACCTGCGCAATAGC
CCAGAAGATAAGCGGGCGGGCGGTGAAGAGTCACAGTTTGAGATGGACATTTAA

Figure 2C

ATGGTCTTCACACTCGAAGATTTCGTTGGGGACTGGGAACAGACAGCCGCCTACAACCTGGACCAAGTCCTTGAA
CAGGGAGGTGTGTCCAGTTTGCTGCAGAATCTCGCCGTGTCCGTAACTCCGATCCAAAGGATTGTCCGGAGCGGT
GAAAATGCCCTGAAGATCGACATCCATGTCATCATCCCGTATGAAGGTCTGAGCGCCGACCAAATGGCCCAGATC
GAAGAGGTGTTTAAGGTGGTGTACCCTGTGGATGATCATCACTTTAAGGTGATCCTGCCCTATGGCACACTGGTAA
TCGACGGGGTTACGCCGAACATGCTGAACTATTTCGGACGGCCGTATGAAGGCATCGCCGTGTTCGACGGCAAAA
AGATCACTGTAACAGGGACCCTGTGGAACGGCAACAAAATTATCGACGAGCGCCTGATCACCCCCGACGGCTCCA
TGCTGTTCCGAGTAACCATCAACAGTGGGAGTTCCGGTGGTGGCGGGAGCGGAGGTGGAGGCTCGAGCGGTATG
TCCTCGTCAGCCGGCAGCGGCCACCAGCCCAGCCAGAGCCGCGCCATCCCCACCCGCACCGTGGCCATCAGCGAC
GCCGCGCAGCTACCTCATGACTATTGCACCACGCCCGGGGGACGCTCTTCTCCACCACACCGGGAGGAACTCGA
ATCATTTATGACAGAAAGTTTCTGTTGGATCGTCGCAATTCTCCCATGGCTCAGACCCCACCCTGCCACCTGCCCAA

Figure 2C (continued)

TATCCCAGGAGTCACTAGCCCTGGCACCTTAATTGAAGACTCCAAAGTAGAAGTAAACAATTTGAACAACTTGAAC
AATCACGACAGGAAACATGCAGTTGGGGATGATGCTCAGTTCGAGATGGACATCTAA

Figure 2D

MVTGYRLFEEILGSSGGGGSGGGGSSGMATVEPETTPTPNPPTTEEEKTESNQEVANPEHYIKHPLQNRWALWFFKN
DKSKTWQANLRLISKFDTVEDFWALYNHIQLSSNLMPGCDYSLFKDGIEPMWEDEKNKRGGRWLITLNKQQRRSDLD
RFWLETLLCLIGESFDDYSDDVCGAVVNVRAKGDKIAIWTTECENREAVTHIGRVYKERLGLPPKIVIGYQSHADTATKS
GSTTKNRFVV

Figure 2E

MVFTLEDFVGDWEQTAAYNLDQVLEQGGVSSLLQNLAVSVTPIQRIVRSGENALKIDIHVIIPYEGLSADQMAQIEEVFK
VVYPVDDHHFKVILPYGTLVIDGVTPNMLNYFGRPYEGIAVFDGKKITVTGTLWNGNKIIDERLITPDGSMLFRVTINSGS
SGGGGSGGGGSSGMSGGSSCSQTPSRAIPATRRVVLGDGVQLPPGDYSTTPGGTLFSTTPGGTRIIYDRKFLMECRNSP
VTKTPPRDLPTIPGVTSPSSDEPPMEASQSHLRNSPEDKRAGGEESQFEMDI

Figure 2F

MVFTLEDFVGDWEQTAAYNLDQVLEQGGVSSLLQNLAVSVTPIQRIVRSGENALKIDIHVIIPYEGLSADQMAQIEEVFK
VVYPVDDHHFKVILPYGTLVIDGVTPNMLNYFGRPYEGIAVFDGKKITVTGTLWNGNKIIDERLITPDGSMLFRVTINSGS
SGGGGSGGGGSSGMSSSAGSGHQPSQSRAIPTRTVAISDAAQLPHDYCTTPGGTLFSTTPGGTRIIYDRKFLLDRRNSP
MAQTPPCHLPNIPGVTSPGTLIEDSKVEVNNLNNLNNHDRKHAVGDDAQFEMDI

LB-4E-BP1 with phospho-mimetic mutations

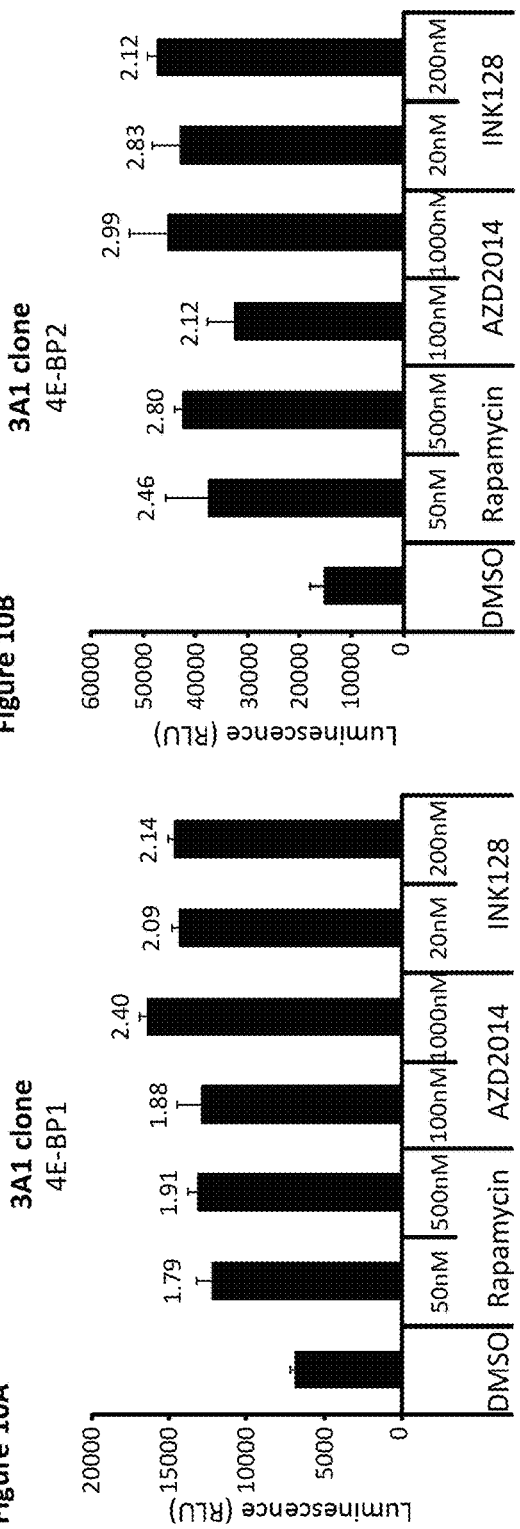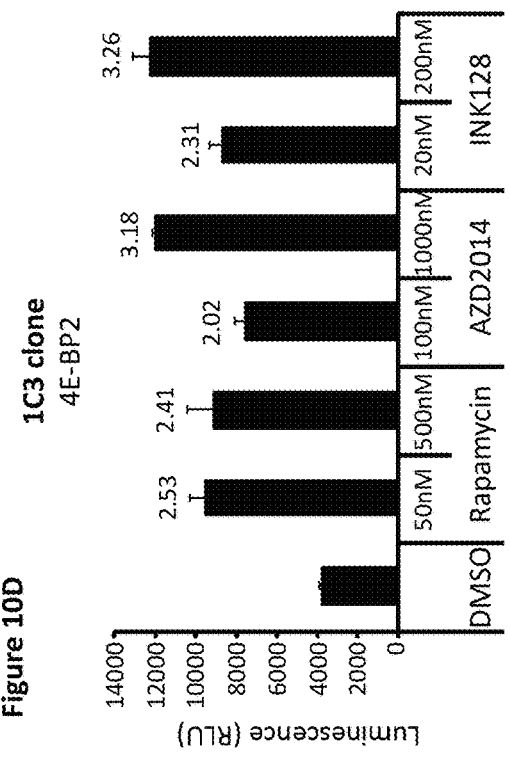

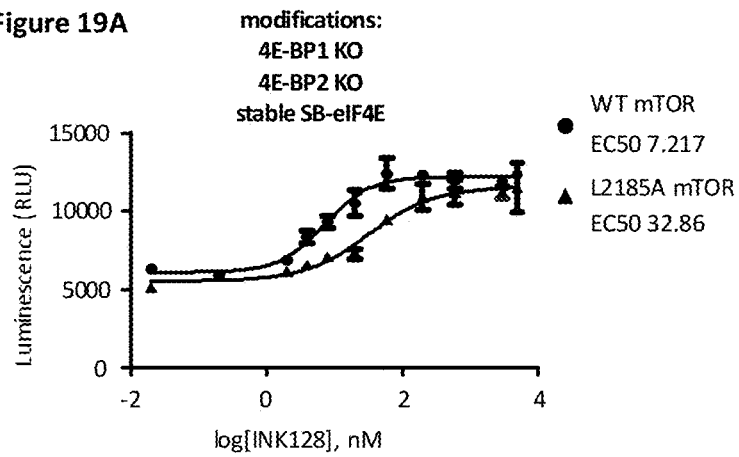
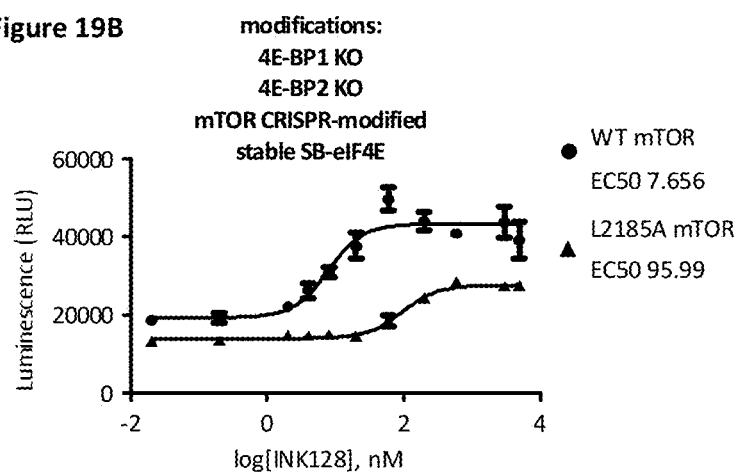
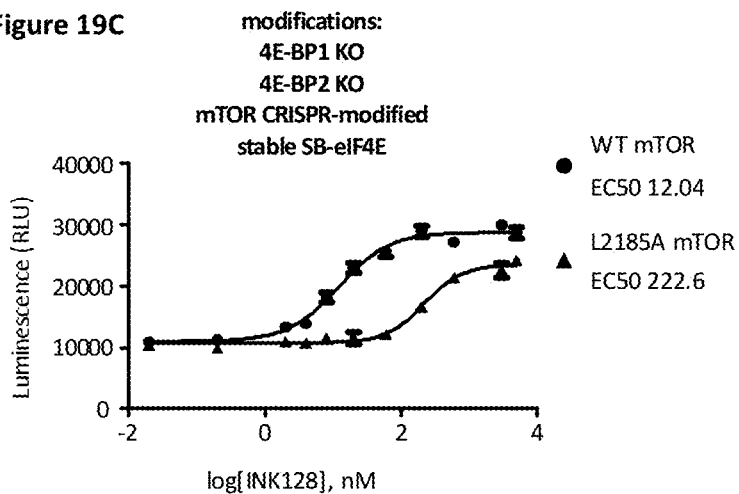

LB-4E-BP1 with phospho-mimetic mutations
(performed in transfected (transient) WT HEK293 cells with SBeIF4E)

LB-4E-BP1 with phospho-mimetic mutations
(performed in 3A1 clone with stable SBeIF4E)

SEQUENCE LISTING

```
<160> NUMBER OF SEQ ID NOS: 104

<210> SEQ ID NO 1
<211> LENGTH: 735
<212> TYPE: DNA
<213> ORGANISM: Homo sapiens

<400> SEQUENCE: 1
atggtgaccg gctaccggct gttcgaggag attctcggga gttccggtgg tggcgggagc      60
ggaggtggag gctcgagcgg tatggcgact gtcgaaccgg aaaccacccc tactcctaat     120
cccccgacta cagaagagga gaaaacggaa tctaatcagg aggttgctaa cccagaacac     180
tatattaaac atcccctaca gaacagatgg gcactctggt tttttaaaaa tgataaaagc     240
aaaacttggc aagcaaacct gcggctgatc tccaagtttg atactgttga agactttttgg    300 gctctgtaca accatatcca gttgtctagt aatttaatgc ctggctgtga ctactcactt     360
tttaaggatg gtattgagcc tatgtgggaa gatgagaaaa acaaacgggg gggacgatgg     420
ctaattacat tgaacaaaca gcagagacga agtgacctcg atcgcttttg gctagagaca     480
```

| | |
|---|---|
| cttctgtgcc ttattggaga atcttttgat gactacagtg atgatgtatg tggcgctgtt | 540 |
| gttaatgtta gagctaaagg tgataagata gcaatatgga ctactgaatg tgaaaacaga | 600 |
| gaagctgtta cacatatagg gagggtatac aaggaaaggt taggacttcc tccaaagata | 660 |
| gtgattggtt atcagtccca cgcagacaca gctactaaga gcggctccac cactaaaaat | 720 |
| aggtttgttg tttaa | 735 |

```
<210> SEQ ID NO 2
<211> LENGTH: 879
<212> TYPE: DNA
<213> ORGANISM: Homo sapiens

<400> SEQUENCE: 2
```

| | |
|---|---|
| atggtcttca cactcgaaga tttcgttggg gactgggaac agacagccgc ctacaacctg | 60 |
| gaccaagtcc ttgaacaggg aggtgtgtcc agtttgctgc agaatctcgc cgtgtccgta | 120 |
| actccgatcc aaaggattgt ccggagcggt gaaaatgccc tgaagatcga catccatgtc | 180 |
| atcatcccgt atgaaggtct gagcgccgac caaatggccc agatcgaaga ggtgtttaag | 240 |
| gtggtgtacc ctgtggatga tcatcacttt aaggtgatcc tgccctatgg cacactggta | 300 |
| atcgacgggg ttacgccgaa catgctgaac tatttcggac ggccgtatga aggcatcgcc | 360 |
| gtgttcgacg gcaaaaagat cactgtaaca gggaccctgt ggaacggcaa caaaattatc | 420 |
| gacgagcgcc tgatcacccc cgacggctcc atgctgttcc gagtaaccat caacagtggg | 480 |
| agttccggtg gtggcgggag cggaggtgga ggctcgagcg gtatgtccgg ggcagcagc | 540 |
| tgcagccaga cccaagccg ggccatcccc gccactcgcc gggtggtgct cggcgacggc | 600 |
| gtgcagctcc cgcccgggga ctacagcacg accccggcg gcacgctctt cagcaccacc | 660 |
| ccggaggta ccaggatcat ctatgaccgg aaattcctga tggagtgtcg gaactcacct | 720 |
| gtgaccaaaa accccccaag ggatctgccc accattccgg gggtcaccag cccttccagt | 780 |
| gatgagcccc ccatggaagc cagccagagc cacctgcgca atagcccaga agataagcgg | 840 |
| gcgggcggtg aagagtcaca gtttgagatg gacatttaa | 879 |

```
<210> SEQ ID NO 3
<211> LENGTH: 885
<212> TYPE: DNA
<213> ORGANISM: Homo sapiens

<400> SEQUENCE: 3
```

| | |
|---|---|
| atggtcttca cactcgaaga tttcgttggg gactgggaac agacagccgc ctacaacctg | 60 |
| gaccaagtcc ttgaacaggg aggtgtgtcc agtttgctgc agaatctcgc cgtgtccgta | 120 |
| actccgatcc aaaggattgt ccggagcggt gaaaatgccc tgaagatcga catccatgtc | 180 |
| atcatcccgt atgaaggtct gagcgccgac caaatggccc agatcgaaga ggtgtttaag | 240 |
| gtggtgtacc ctgtggatga tcatcacttt aaggtgatcc tgccctatgg cacactggta | 300 |
| atcgacgggg ttacgccgaa catgctgaac tatttcggac ggccgtatga aggcatcgcc | 360 |
| gtgttcgacg gcaaaaagat cactgtaaca gggaccctgt ggaacggcaa caaaattatc | 420 |
| gacgagcgcc tgatcacccc cgacggctcc atgctgttcc gagtaaccat caacagtggg | 480 |
| agttccggtg gtggcgggag cggaggtgga ggctcgagcg gtatgtcctc gtcagccggc | 540 |
| agcggccacc agcccagcca gagccgcgcc atccccaccc gcaccgtggc catcagcgac | 600 |
| gccgcgcagc tacctcatga ctattgcacc acgcccgggg ggacgctctt ctccaccaca | 660 |
| ccggaggaa ctcgaatcat ttatgacaga aagtttctgt tggatcgtcg caattctccc | 720 |

-continued

```
atggctcaga ccccaccctg ccacctgccc aatatcccag gagtcactag ccctggcacc      780
ttaattgaag actccaaagt agaagtaaac aatttgaaca acttgaacaa tcacgacagg      840
aaacatgcag ttggggatga tgctcagttc gagatggaca tctaa                     885
```

<210> SEQ ID NO 4
<211> LENGTH: 244
<212> TYPE: PRT
<213> ORGANISM: Homo sapiens

<400> SEQUENCE: 4

```
Met Val Thr Gly Tyr Arg Leu Phe Glu Glu Ile Leu Gly Ser Ser Gly
1               5                   10                  15

Gly Gly Gly Ser Gly Gly Gly Ser Ser Gly Met Ala Thr Val Glu
            20                  25                  30

Pro Glu Thr Thr Pro Thr Pro Asn Pro Pro Thr Glu Glu Lys
            35                  40                  45

Thr Glu Ser Asn Gln Glu Val Ala Asn Pro Glu His Tyr Ile Lys His
    50                  55                  60

Pro Leu Gln Asn Arg Trp Ala Leu Trp Phe Phe Lys Asn Asp Lys Ser
65                  70                  75                  80

Lys Thr Trp Gln Ala Asn Leu Arg Leu Ile Ser Lys Phe Asp Thr Val
                85                  90                  95

Glu Asp Phe Trp Ala Leu Tyr Asn His Ile Gln Leu Ser Ser Asn Leu
            100                 105                 110

Met Pro Gly Cys Asp Tyr Ser Leu Phe Lys Asp Gly Ile Glu Pro Met
        115                 120                 125

Trp Glu Asp Glu Lys Asn Lys Arg Gly Gly Arg Trp Leu Ile Thr Leu
    130                 135                 140

Asn Lys Gln Gln Arg Arg Ser Asp Leu Asp Arg Phe Trp Leu Glu Thr
145                 150                 155                 160

Leu Leu Cys Leu Ile Gly Glu Ser Phe Asp Tyr Ser Asp Asp Val
                165                 170                 175

Cys Gly Ala Val Val Asn Val Arg Ala Lys Gly Asp Lys Ile Ala Ile
            180                 185                 190

Trp Thr Thr Glu Cys Glu Asn Arg Glu Ala Val Thr His Ile Gly Arg
        195                 200                 205

Val Tyr Lys Glu Arg Leu Gly Leu Pro Pro Lys Ile Val Ile Gly Tyr
    210                 215                 220

Gln Ser His Ala Asp Thr Ala Thr Lys Ser Gly Ser Thr Thr Lys Asn
225                 230                 235                 240

Arg Phe Val Val
```

<210> SEQ ID NO 5
<211> LENGTH: 292
<212> TYPE: PRT
<213> ORGANISM: Homo sapiens

<400> SEQUENCE: 5

```
Met Val Phe Thr Leu Glu Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Ile Val Arg
        35                  40                  45
```

```
Ser Gly Glu Asn Ala Leu Lys Ile Asp Ile His Val Ile Ile Pro Tyr
 50                  55                  60

Glu Gly Leu Ser Ala Asp Gln Met Ala Gln Ile Glu Glu Val Phe Lys
 65                  70                  75                  80

Val Val Tyr Pro Val Asp Asp His His Phe Lys Val Ile Leu Pro Tyr
                 85                  90                  95

Gly Thr Leu Val Ile Asp Gly Val Thr Pro Asn Met Leu Asn Tyr Phe
                100                 105                 110

Gly Arg Pro Tyr Glu Gly Ile Ala Val Phe Asp Gly Lys Lys Ile Thr
                115                 120                 125

Val Thr Gly Thr Leu Trp Asn Gly Asn Lys Ile Ile Asp Glu Arg Leu
130                 135                 140

Ile Thr Pro Asp Gly Ser Met Leu Phe Arg Val Thr Ile Asn Ser Gly
145                 150                 155                 160

Ser Ser Gly Gly Gly Gly Ser Gly Gly Gly Ser Ser Gly Met Ser
                165                 170                 175

Gly Gly Ser Ser Cys Ser Gln Thr Pro Ser Arg Ala Ile Pro Ala Thr
                180                 185                 190

Arg Arg Val Val Leu Gly Asp Gly Val Gln Leu Pro Pro Gly Asp Tyr
                195                 200                 205

Ser Thr Thr Pro Gly Gly Thr Leu Phe Ser Thr Thr Pro Gly Gly Thr
                210                 215                 220

Arg Ile Ile Tyr Asp Arg Lys Phe Leu Met Glu Cys Arg Asn Ser Pro
225                 230                 235                 240

Val Thr Lys Thr Pro Pro Arg Asp Leu Pro Thr Ile Pro Gly Val Thr
                245                 250                 255

Ser Pro Ser Ser Asp Glu Pro Pro Met Glu Ala Ser Gln Ser His Leu
                260                 265                 270

Arg Asn Ser Pro Glu Asp Lys Arg Ala Gly Gly Glu Glu Ser Gln Phe
                275                 280                 285

Glu Met Asp Ile
                290

<210> SEQ ID NO 6
<211> LENGTH: 294
<212> TYPE: PRT
<213> ORGANISM: Homo sapiens

<400> SEQUENCE: 6

Met Val Phe Thr Leu Glu Asp Phe Val Gly Asp Trp Glu Gln Thr Ala
 1               5                  10                  15

Ala Tyr Asn Leu Asp Gln Val Leu Glu Gln Gly Gly Val Ser Ser Leu
                 20                  25                  30

Leu Gln Asn Leu Ala Val Ser Val Thr Pro Ile Gln Arg Ile Val Arg
                 35                  40                  45

Ser Gly Glu Asn Ala Leu Lys Ile Asp Ile His Val Ile Ile Pro Tyr
 50                  55                  60

Glu Gly Leu Ser Ala Asp Gln Met Ala Gln Ile Glu Glu Val Phe Lys
 65                  70                  75                  80

Val Val Tyr Pro Val Asp Asp His His Phe Lys Val Ile Leu Pro Tyr
                 85                  90                  95

Gly Thr Leu Val Ile Asp Gly Val Thr Pro Asn Met Leu Asn Tyr Phe
                100                 105                 110

Gly Arg Pro Tyr Glu Gly Ile Ala Val Phe Asp Gly Lys Lys Ile Thr
                115                 120                 125
```

```
Val Thr Gly Thr Leu Trp Asn Gly Asn Lys Ile Ile Asp Glu Arg Leu
130                 135                 140

Ile Thr Pro Asp Gly Ser Met Leu Phe Arg Val Thr Ile Asn Ser Gly
145                 150                 155                 160

Ser Ser Gly Gly Gly Ser Gly Gly Gly Ser Ser Gly Met Ser
                165                 170                 175

Ser Ser Ala Gly Ser Gly His Gln Pro Ser Gln Ser Arg Ala Ile Pro
            180                 185                 190

Thr Arg Thr Val Ala Ile Ser Asp Ala Ala Gln Leu Pro His Asp Tyr
            195                 200                 205

Cys Thr Thr Pro Gly Gly Thr Leu Phe Ser Thr Thr Pro Gly Gly Thr
210                 215                 220

Arg Ile Ile Tyr Asp Arg Lys Phe Leu Leu Asp Arg Arg Asn Ser Pro
225                 230                 235                 240

Met Ala Gln Thr Pro Pro Cys His Leu Pro Asn Ile Pro Gly Val Thr
                245                 250                 255

Ser Pro Gly Thr Leu Ile Glu Asp Ser Lys Val Glu Val Asn Asn Leu
            260                 265                 270

Asn Asn Leu Asn Asn His Asp Arg Lys His Ala Val Gly Asp Asp Ala
            275                 280                 285

Gln Phe Glu Met Asp Ile
            290
```

<210> SEQ ID NO 7
<211> LENGTH: 45
<212> TYPE: DNA
<213> ORGANISM: Homo sapiens

<400> SEQUENCE: 7
gaggtggagg ctcgagcggt atggcgactg tcgaaccgga aacca          45

<210> SEQ ID NO 8
<211> LENGTH: 46
<212> TYPE: DNA
<213> ORGANISM: Homo sapiens

<400> SEQUENCE: 8
gcgtacgcgt atctagatta aacaacaaac ctattttag tggtgg          46

<210> SEQ ID NO 9
<211> LENGTH: 39
<212> TYPE: DNA
<213> ORGANISM: Homo sapiens

<400> SEQUENCE: 9
gaggtggagg ctcgagcggt gagaaaacgg aatctaatc                 39

<210> SEQ ID NO 10
<211> LENGTH: 46
<212> TYPE: DNA
<213> ORGANISM: Homo sapiens

<400> SEQUENCE: 10
gcgtacgcgt atctagatta aacaacaaac ctattttag tggtgg          46

<210> SEQ ID NO 11
<211> LENGTH: 45
<212> TYPE: DNA
<213> ORGANISM: Homo sapiens

<400> SEQUENCE: 11
gaggtggagg ctcgagcggt gaggttgcta acccagaaca ctata     45

<210> SEQ ID NO 12
<211> LENGTH: 46
<212> TYPE: DNA
<213> ORGANISM: Homo sapiens

<400> SEQUENCE: 12
gcgtacgcgt atctagatta aacaacaaac ctattttag tggtgg     46

<210> SEQ ID NO 13
<211> LENGTH: 48
<212> TYPE: DNA
<213> ORGANISM: Homo sapiens

<400> SEQUENCE: 13
gaggtggagg ctcgagcggt atgtccgggg gcagcagctg cagccaga     48

<210> SEQ ID NO 14
<211> LENGTH: 43
<212> TYPE: DNA
<213> ORGANISM: Homo sapiens

<400> SEQUENCE: 14
cgcgtacgct ctagattaaa tgtccatctc aaactgtgac tct     43

<210> SEQ ID NO 15
<211> LENGTH: 45
<212> TYPE: DNA
<213> ORGANISM: Homo sapiens

<400> SEQUENCE: 15
gaggtggagg ctcgagcggt ctcccgcccg gggactacag cacga     45

<210> SEQ ID NO 16
<211> LENGTH: 43
<212> TYPE: DNA
<213> ORGANISM: Homo sapiens

<400> SEQUENCE: 16
cgcgtacgct ctagattaaa tgtccatctc aaactgtgac tct     43

<210> SEQ ID NO 17
<211> LENGTH: 34
<212> TYPE: DNA
<213> ORGANISM: Homo sapiens

<400> SEQUENCE: 17
gcgatcgcta gcatgtccgg ggcagcagc tgca     34

<210> SEQ ID NO 18
<211> LENGTH: 42
<212> TYPE: DNA
<213> ORGANISM: Homo sapiens

<400> SEQUENCE: 18
gccaccaccg ctcgagccaa tgtccatctc aaactgtgac tc     42

<210> SEQ ID NO 19
<211> LENGTH: 34
<212> TYPE: DNA
<213> ORGANISM: Homo sapiens

```
<400> SEQUENCE: 19
gcgatcgcta gcatgtccgg gggcagcagc tgca                                34

<210> SEQ ID NO 20
<211> LENGTH: 36
<212> TYPE: DNA
<213> ORGANISM: Homo sapiens

<400> SEQUENCE: 20
gccaccaccg ctcgagccct ggctggcttc catggg                              36

<210> SEQ ID NO 21
<211> LENGTH: 34
<212> TYPE: DNA
<213> ORGANISM: Homo sapiens

<400> SEQUENCE: 21
gcgatcgcta gcatgtccgg gggcagcagc tgca                                34

<210> SEQ ID NO 22
<211> LENGTH: 39
<212> TYPE: DNA
<213> ORGANISM: Homo sapiens

<400> SEQUENCE: 22
gccaccaccg ctcgagccgg aagggctggt gaccccgg                            39

<210> SEQ ID NO 23
<211> LENGTH: 34
<212> TYPE: DNA
<213> ORGANISM: Homo sapiens

<400> SEQUENCE: 23
gcgatcgcta gcatgtccgg gggcagcagc tgca                                34

<210> SEQ ID NO 24
<211> LENGTH: 42
<212> TYPE: DNA
<213> ORGANISM: Homo sapiens

<400> SEQUENCE: 24
gccaccaccg ctcgagccaa tgtccatctc aaactgtgac tc                       42

<210> SEQ ID NO 25
<211> LENGTH: 41
<212> TYPE: DNA
<213> ORGANISM: Homo sapiens

<400> SEQUENCE: 25
tggaggctcg agcggtatgt cctcgtcagc cggcagcggc c                        41

<210> SEQ ID NO 26
<211> LENGTH: 43
<212> TYPE: DNA
<213> ORGANISM: Homo sapiens

<400> SEQUENCE: 26
ccgccccgac tctagattag atgtccatct cgaactgagc atc                      43

<210> SEQ ID NO 27
<211> LENGTH: 26
<212> TYPE: DNA
<213> ORGANISM: Homo sapiens
```

<400> SEQUENCE: 27
atgatgacac aaaccccgcc cagcgt                                26

<210> SEQ ID NO 28
<211> LENGTH: 30
<212> TYPE: DNA
<213> ORGANISM: Homo sapiens

<400> SEQUENCE: 28
ctgcattcta gttgtggttt gtccaaactc                            30

<210> SEQ ID NO 29
<211> LENGTH: 35
<212> TYPE: DNA
<213> ORGANISM: Homo sapiens

<400> SEQUENCE: 29
atggagtgtc ggaacgaacc tgtgaccaaa acacc                      35

<210> SEQ ID NO 30
<211> LENGTH: 35
<212> TYPE: DNA
<213> ORGANISM: Homo sapiens

<400> SEQUENCE: 30
ggtgttttgg tcacaggttc gttccgacac tccat                      35

<210> SEQ ID NO 31
<211> LENGTH: 49
<212> TYPE: DNA
<213> ORGANISM: Homo sapiens

<400> SEQUENCE: 31
tcggaactca cctgtgacca agaaccccc aagggatctg cccaccatt        49

<210> SEQ ID NO 32
<211> LENGTH: 49
<212> TYPE: DNA
<213> ORGANISM: Homo sapiens

<400> SEQUENCE: 32
aatggtgggc agatcccttg ggggttcttt ggtcacaggt gagttccga       49

<210> SEQ ID NO 33
<211> LENGTH: 60
<212> TYPE: DNA
<213> ORGANISM: Homo sapiens

<400> SEQUENCE: 33
ggggactaca gcacggagcc cggcggcacg ctcttcagca ccgagccggg aggtaccagg    60

<210> SEQ ID NO 34
<211> LENGTH: 60
<212> TYPE: DNA
<213> ORGANISM: Homo sapiens

<400> SEQUENCE: 34
cctggtacct cccggctcgg tgctgaagag cgtgccgccg ggctccgtgc tgtagtcccc    60

<210> SEQ ID NO 35
<211> LENGTH: 44
<212> TYPE: DNA
<213> ORGANISM: Homo sapiens

<400> SEQUENCE: 35
ggcggcacgc tcttcagcac cgagccggga ggtaccagga tcat        44

<210> SEQ ID NO 36
<211> LENGTH: 44
<212> TYPE: DNA
<213> ORGANISM: Homo sapiens

<400> SEQUENCE: 36
atgatcctgg tacctcccgg ctcggtgctg aagagcgtgc cgcc        44

<210> SEQ ID NO 37
<211> LENGTH: 48
<212> TYPE: DNA
<213> ORGANISM: Homo sapiens

<400> SEQUENCE: 37
atggagtgtc ggaacgaacc tgtgaccaaa gaaccccaa gggatctg    48

<210> SEQ ID NO 38
<211> LENGTH: 48
<212> TYPE: DNA
<213> ORGANISM: Homo sapiens

<400> SEQUENCE: 38 cagatcccctt gggggttctt tggtcacagg ttcgttccga cactccat    48

<210> SEQ ID NO 39
<211> LENGTH: 43
<212> TYPE: DNA
<213> ORGANISM: Homo sapiens

<400> SEQUENCE: 39
atgaaggcct ggaagaggca attcgtttgt actttgggga aag         43

<210> SEQ ID NO 40
<211> LENGTH: 43
<212> TYPE: DNA
<213> ORGANISM: Homo sapiens

<400> SEQUENCE: 40
cttttcccca agtacaaacg aattgcctct tccaggcctt cat          43

<210> SEQ ID NO 41
<211> LENGTH: 47
<212> TYPE: DNA
<213> ORGANISM: Homo sapiens

<400> SEQUENCE: 41
aaactgcacg agtgggagga tccccttgtg gcctatgaca agaaaat      47

<210> SEQ ID NO 42
<211> LENGTH: 47
<212> TYPE: DNA
<213> ORGANISM: Homo sapiens

<400> SEQUENCE: 42
attttcttgt cataggccac aaggggatcc tcccactcgt gcagttt      47

<210> SEQ ID NO 43
<211> LENGTH: 44
<212> TYPE: DNA
<213> ORGANISM: Homo sapiens

```
<400> SEQUENCE: 43
tgggacctct attatcatgt gttacgacga atctcaaagc agct                    44

<210> SEQ ID NO 44
<211> LENGTH: 44
<212> TYPE: DNA
<213> ORGANISM: Homo sapiens

<400> SEQUENCE: 44
agctgctttg agattcgtcg taacacatga taatagaggt ccca                    44

<210> SEQ ID NO 45
<211> LENGTH: 50
<212> TYPE: DNA
<213> ORGANISM: Homo sapiens

<400> SEQUENCE: 45
acccttctgg ccaatgaccc aacatatctt cggaaaaacc tcagcatcca              50

<210> SEQ ID NO 46
<211> LENGTH: 50
<212> TYPE: DNA
<213> ORGANISM: Homo sapiens

<400> SEQUENCE: 46
tggatgctga ggttttccg aagatatgtt gggtcattgg ccagaagggt               50

<210> SEQ ID NO 47
<211> LENGTH: 49
<212> TYPE: DNA
<213> ORGANISM: Homo sapiens

<400> SEQUENCE: 47
gcaacggaca tgagtttgtt ttcgctctaa aaggccatga agatctgcg               49

<210> SEQ ID NO 48
<211> LENGTH: 49
<212> TYPE: DNA
<213> ORGANISM: Homo sapiens

<400> SEQUENCE: 48
cgcagatctt catggccttt tagagcgaaa acaaactcat gtccgttgc               49

<210> SEQ ID NO 49
<211> LENGTH: 26
<212> TYPE: DNA
<213> ORGANISM: Homo sapiens

<400> SEQUENCE: 49
gatcggccac tcgccgggtg gtgctg                                        26

<210> SEQ ID NO 50
<211> LENGTH: 26
<212> TYPE: DNA
<213> ORGANISM: Homo sapiens

<400> SEQUENCE: 50
aaaacagcac cacccggcga gtggcc                                        26

<210> SEQ ID NO 51
<211> LENGTH: 26
<212> TYPE: DNA
<213> ORGANISM: Homo sapiens
```

<400> SEQUENCE: 51
gatcgctggc tgcagctgct gccccg 26

<210> SEQ ID NO 52
<211> LENGTH: 26
<212> TYPE: DNA
<213> ORGANISM: Homo sapiens

<400> SEQUENCE: 52
aaaacggggc agcagctgca gccagc 26

<210> SEQ ID NO 53
<211> LENGTH: 26
<212> TYPE: DNA
<213> ORGANISM: Homo sapiens

<400> SEQUENCE: 53
gatcgggcca gccgtccgcc gcgccg 26

<210> SEQ ID NO 54
<211> LENGTH: 26
<212> TYPE: DNA
<213> ORGANISM: Homo sapiens

<400> SEQUENCE: 54
aaaacggcgc ggcggacggc tggccc 26

<210> SEQ ID NO 55
<211> LENGTH: 26
<212> TYPE: DNA
<213> ORGANISM: Homo sapiens

<400> SEQUENCE: 55
gatcgatagt catgaggtag ctgcgg 26

<210> SEQ ID NO 56
<211> LENGTH: 26
<212> TYPE: DNA
<213> ORGANISM: Homo sapiens

<400> SEQUENCE: 56
aaaaccgcag ctacctcatg actatc 26

<210> SEQ ID NO 57
<211> LENGTH: 25
<212> TYPE: DNA
<213> ORGANISM: Homo sapiens

<400> SEQUENCE: 57
agggcagcga gaggttcgcg ggtgc 25

<210> SEQ ID NO 58
<211> LENGTH: 25
<212> TYPE: DNA
<213> ORGANISM: Homo sapiens

<400> SEQUENCE: 58
tccaatccgc gattcccgat cctcc 25

<210> SEQ ID NO 59
<211> LENGTH: 22
<212> TYPE: DNA
<213> ORGANISM: Homo sapiens

<400> SEQUENCE: 59
acaaagccga gagcccgcgc cc                                              22

<210> SEQ ID NO 60
<211> LENGTH: 25
<212> TYPE: DNA
<213> ORGANISM: Homo sapiens

<400> SEQUENCE: 60
aagcggccgg gcaccgaggc gccga                                           25

<210> SEQ ID NO 61
<211> LENGTH: 26
<212> TYPE: DNA
<213> ORGANISM: Homo sapiens

<400> SEQUENCE: 61
gatcgcgccg ggtggtgctc ggcgag                                          26

<210> SEQ ID NO 62
<211> LENGTH: 26
<212> TYPE: DNA
<213> ORGANISM: Homo sapiens

<400> SEQUENCE: 62
aaaactcgcc gagcaccacc cggcgc                                          26

<210> SEQ ID NO 63
<211> LENGTH: 26
<212> TYPE: DNA
<213> ORGANISM: Homo sapiens

<400> SEQUENCE: 63
gatcgggcga gtggcgggga tggccg                                          26

<210> SEQ ID NO 64
<211> LENGTH: 26
<212> TYPE: DNA
<213> ORGANISM: Homo sapiens

<400> SEQUENCE: 64
aaaacggcca tccccgccac tcgccc                                          26

<210> SEQ ID NO 65
<211> LENGTH: 26
<212> TYPE: DNA
<213> ORGANISM: Homo sapiens

<400> SEQUENCE: 65
gatcgccaca ccgggaggtg agcgcg                                          26

<210> SEQ ID NO 66
<211> LENGTH: 26
<212> TYPE: DNA
<213> ORGANISM: Homo sapiens

<400> SEQUENCE: 66
aaaacgcgct cacctcccgg tgtggc                                          26

<210> SEQ ID NO 67
<211> LENGTH: 26
<212> TYPE: DNA
<213> ORGANISM: Homo sapiens

<400> SEQUENCE: 67
gatcgcgcgg cgtcgctgat ggccag                                              26

<210> SEQ ID NO 68
<211> LENGTH: 25
<212> TYPE: DNA
<213> ORGANISM: Homo sapiens

<400> SEQUENCE: 68
aaaactggcc atcagcgacg ccgcg                                               25

<210> SEQ ID NO 69
<211> LENGTH: 26
<212> TYPE: DNA
<213> ORGANISM: Homo sapiens

<400> SEQUENCE: 69
gatcgaatga aatttaagaa gcccgg                                              26

<210> SEQ ID NO 70
<211> LENGTH: 26
<212> TYPE: DNA
<213> ORGANISM: Homo sapiens

<400> SEQUENCE: 70
aaaaccgggc ttcttaaatt tcattc                                              26

<210> SEQ ID NO 71
<211> LENGTH: 26
<212> TYPE: DNA
<213> ORGANISM: Homo sapiens

<400> SEQUENCE: 71
gatcgatgaa ctagtatcca gtaagg                                              26

<210> SEQ ID NO 72
<211> LENGTH: 26
<212> TYPE: DNA
<213> ORGANISM: Homo sapiens

<400> SEQUENCE: 72
aaaaccttac tggatactag ttcatc                                              26

<210> SEQ ID NO 73
<211> LENGTH: 26
<212> TYPE: DNA
<213> ORGANISM: Homo sapiens

<400> SEQUENCE: 73
gatcgtacta gaaagaacct aggacg                                              26

<210> SEQ ID NO 74
<211> LENGTH: 26
<212> TYPE: DNA
<213> ORGANISM: Homo sapiens

<400> SEQUENCE: 74
aaaacgtcct aggttctttc tagtac                                              26

<210> SEQ ID NO 75
<211> LENGTH: 26
<212> TYPE: DNA
<213> ORGANISM: Homo sapiens

```
<400> SEQUENCE: 75
gatcgactgt ctctgacctc aagtcg                                    26

<210> SEQ ID NO 76
<211> LENGTH: 26
<212> TYPE: DNA
<213> ORGANISM: Homo sapiens

<400> SEQUENCE: 76
aaaacgactt gaggtcagag acagtc                                    26

<210> SEQ ID NO 77
<211> LENGTH: 37
<212> TYPE: DNA
<213> ORGANISM: Homo sapiens

<400> SEQUENCE: 77
aaaggcaccc aacctgtcac atccataaaa catgcag                        37

<210> SEQ ID NO 78
<211> LENGTH: 30
<212> TYPE: DNA
<213> ORGANISM: Homo sapiens

<400> SEQUENCE: 78
attttctccc ctacccccca aaagggaaa                                 30

<210> SEQ ID NO 79
<211> LENGTH: 26
<212> TYPE: DNA
<213> ORGANISM: Homo sapiens

<400> SEQUENCE: 79
gatcgcctgg tactagaaag aacctg                                    26

<210> SEQ ID NO 80
<211> LENGTH: 26
<212> TYPE: DNA
<213> ORGANISM: Homo sapiens

<400> SEQUENCE: 80
aaaacaggtt ctttctagta ccaggc                                    26

<210> SEQ ID NO 81
<211> LENGTH: 26
<212> TYPE: DNA
<213> ORGANISM: Homo sapiens

<400> SEQUENCE: 81
gatcgtttct agtaccaggg ataaag                                    26

<210> SEQ ID NO 82
<211> LENGTH: 26
<212> TYPE: DNA
<213> ORGANISM: Homo sapiens

<400> SEQUENCE: 82
aaaactttat ccctggtact agaaac                                    26

<210> SEQ ID NO 83
<211> LENGTH: 26
<212> TYPE: DNA
<213> ORGANISM: Homo sapiens
```

```
<400> SEQUENCE: 83
gatcggctgc tagaattaaa agccag                                          26

<210> SEQ ID NO 84
<211> LENGTH: 26
<212> TYPE: DNA
<213> ORGANISM: Homo sapiens

<400> SEQUENCE: 84
aaaactggct tttaattcta gcagcc                                          26

<210> SEQ ID NO 85
<211> LENGTH: 26
<212> TYPE: DNA
<213> ORGANISM: Homo sapiens

<400> SEQUENCE: 85
gatcgtagca gcagccctgg gccacg                                          26

<210> SEQ ID NO 86
<211> LENGTH: 26
<212> TYPE: DNA
<213> ORGANISM: Homo sapiens

<400> SEQUENCE: 86
aaaacgtggc ccagggctgc tgctac                                          26

<210> SEQ ID NO 87
<211> LENGTH: 31
<212> TYPE: DNA
<213> ORGANISM: Homo sapiens

<400> SEQUENCE: 87
ataacagtga ttgggatggg tttggagagt t                                    31

<210> SEQ ID NO 88
<211> LENGTH: 27
<212> TYPE: DNA
<213> ORGANISM: Homo sapiens

<400> SEQUENCE: 88
aggaggtata gttcaaacca aagaaga                                         27

<210> SEQ ID NO 89
<211> LENGTH: 25
<212> TYPE: DNA
<213> ORGANISM: Homo sapiens

<400> SEQUENCE: 89
aaggtggcat cttggccata ggtaa                                           25

<210> SEQ ID NO 90
<211> LENGTH: 26
<212> TYPE: DNA
<213> ORGANISM: Homo sapiens

<400> SEQUENCE: 90
tcagctctgg taaactgtct gaaaag                                          26

<210> SEQ ID NO 91
<211> LENGTH: 43
<212> TYPE: DNA
<213> ORGANISM: Homo sapiens
```

<400> SEQUENCE: 91
gtaccaggat catctatgac tggaaattcc tgatggagtg tcg             43

<210> SEQ ID NO 92
<211> LENGTH: 43
<212> TYPE: DNA
<213> ORGANISM: Homo sapiens

<400> SEQUENCE: 92
cgacactcca tcaggaattt ccagtcatag atgatcctgg tac             43

<210> SEQ ID NO 93
<211> LENGTH: 44
<212> TYPE: DNA
<213> ORGANISM: Homo sapiens

<400> SEQUENCE: 93
tcatctatga ccggaaattc cagatggagt gtcggaactc acct            44

<210> SEQ ID NO 94
<211> LENGTH: 44
<212> TYPE: DNA
<213> ORGANISM: Homo sapiens

<400> SEQUENCE: 94
aggtgagttc cgacactcca tctggaattt ccggtcatag atga            44

<210> SEQ ID NO 95
<211> LENGTH: 43
<212> TYPE: DNA
<213> ORGANISM: Homo sapiens

<400> SEQUENCE: 95
acagaaagtt tctgttggat cctcgcaatt ctcccatggc tca             43

<210> SEQ ID NO 96
<211> LENGTH: 43
<212> TYPE: DNA
<213> ORGANISM: Homo sapiens

<400> SEQUENCE: 96
tgagccatgg gagaattgcg aggatccaac agaaactttc tgt             43

<210> SEQ ID NO 97
<211> LENGTH: 43
<212> TYPE: DNA
<213> ORGANISM: Homo sapiens

<400> SEQUENCE: 97
gaggaactcg aatcatttat tacagaaagt ttctgttgga tcg             43

<210> SEQ ID NO 98
<211> LENGTH: 43
<212> TYPE: DNA
<213> ORGANISM: Homo sapiens

<400> SEQUENCE: 98
cgatccaaca gaaactttct gtaataaatg attcgagttc ctc             43

<210> SEQ ID NO 99
<211> LENGTH: 30
<212> TYPE: DNA
<213> ORGANISM: Homo sapiens

<400> SEQUENCE: 99
actggccggt acctgagtct aaatgagtct                                30

<210> SEQ ID NO 100
<211> LENGTH: 24
<212> TYPE: DNA
<213> ORGANISM: Homo sapiens

<400> SEQUENCE: 100
aaggagctga ctgggttgaa ggct                                      24

<210> SEQ ID NO 101
<211> LENGTH: 7650
<212> TYPE: DNA
<213> ORGANISM: Homo sapiens

<400> SEQUENCE: 101
atgcttggaa ccggacctgc cgccgccacc accgctgcca ccacatctag caatgtgagc      60
gtcctgcagc agtttgccag tggcctaaag agccggaatg aggaaaccag gccaaagcc     120 gccaaggagc tccagcacta tgtcaccatg gaactccgag agatgagtca gaggagtct     180 actcgcttct atgaccaact gaaccatcac attttttgaat tggtttccag ctcagatgcc    240
aatgagagga aggtggcat cttggccata gctagcctca taggagtgga aggtgggaat     300
gccacccgaa ttggcagatt tgccaactat cttcggaacc cctcccctc caatgaccca     360 gttgtcatgg aaatggcatc caaggccatt ggccgtcttg ccatggcagg ggacactttt     420
accgctgagt acgtggaatt tgaggtgaag cgagccctgg aatggctggg tgctgaccgc     480
aatgagggcc ggagacatgc agctgtcctg gttctccgtg agctggccat cagcgtccct     540
accttcttct tccagcaagt gcaacccttc ttttgacaaca ttttgtggc cgtgtgggac     600 cccaaacagg ccatccgtga gggagctgta gccgcccttc gtgcctgtct gattctcaca     660
acccagcgtg agccgaagga gatgcagaag cctcagtggt acaggcacac atttgaagaa     720
gcagagaagg gattttgatga gaccttggcc aaagagaagg gcatgaatcg ggatgatcgg     780
atccatggag ccttgttgat ccttaacgag ctggtccgaa tcagcagcat ggagggagag     840
cgtctgagag aagaaatgga agaaatcaca cagcagcagc tggtacacga caagtactgc     900
aaagatctca tgggcttcgg aacaaaaacct cgtcacatta ccccccttcac cagtttccag     960 gctgtacagc cccagcagtc aaatgccttg gtggggctgc tggggtacag ctctcaccaa    1020
ggcctcatgg gatttgggac ctcccccagt ccagctaagt ccaccctggt ggagagccgg    1080
tgttgcagag acttgatgga ggagaaattt gatcaggtgt gccagtgggt gctgaaatgc    1140
aggaatagca agaactcgct gatccaaatg acaatcctta atttgttgcc ccgcttggct    1200
gcattccgac cttctgcctt cacagatacc cagtatctcc aagataccat gaaccatgtc    1260
ctaagctgtg tcaagaagga gaaggaacgt acagcggcct tccaagccct ggggctactt    1320
tctgtggctg tgaggtctga gtttaaggtc tatttgcctc gcgtgctgga catcatccga    1380
gcggccctgc ccccaaagga cttcgcccat aagaggcaga aggcaatgca ggtggatgcc    1440
acagtcttca cttgcatcag catgctggct cgagcaatgg ggccaggcat ccagcaggat    1500
atcaaggagc tgctggagcc catgctggca gtgggactaa gccctgccct cactgcagtg    1560
ctctacgacc tgagccgtca gattccacag ctaaagaagg acattcaaga tgggctactg    1620
aaaatgctgt ccctggtcct tatgcacaaa ccccttcgcc acccaggcat gcccaagggc    1680
ctggcccatc agctggcctc tcctggcctc acgaccctcc ctgaggccag cgatgtgggc    1740

```
agcatcactc ttgccctccg aacgcttggc agctttgaat ttgaaggcca ctctctgacc   1800
caatttgttc gccactgtgc ggatcatttc ctgaacagtg agcacaagga gatccgcatg   1860
gaggctgccc gcacctgctc ccgcctgctc acaccctcca tccacctcat cagtggccat   1920
gctcatgtgg ttagccagac cgcagtgcaa gtggtggcag atgtgcttag caaactgctc   1980
gtagttggga taacagatcc tgaccctgac attcgctact gtgtcttggc gtccctggac   2040
gagcgctttg atgcacacct ggcccaggcg gagaacttgc aggccttgtt tgtggctctg   2100
aatgaccagg tgtttgagat ccgggagctg gccatctgca ctgtgggccg actcagtagc   2160
atgaaccctg cctttgtcat gccttttcct cgcaagatgc tcatccagat tttgacagag   2220
ttggagcaca gtgggattgg aagaatcaaa gagcagagtg cccgcatgct ggggcacctg   2280
gtctccaatg ccccccgact catccgcccc tacatggagc ctattctgaa ggcattaatt   2340
ttgaaactga aagatccaga ccctgatcca aacccaggtg tgatcaataa tgtcctggca   2400
acaataggag aattggcaca ggttagtggc ctggaaatga ggaaatgggt tgatgaactt   2460
tttattatca tcatggacat gctccaggat tcctctttgt tggccaaaag gcaggtggct   2520
ctgtggaccc tgggacagtt ggtggccagc actggctatg tagtagagcc ctacaggaag   2580
taccctactt tgcttgaggt gctactgaat tttctgaaga ctgagcagaa ccagggtaca   2640
cgcagagagg ccatccgtgt gttagggctt tagggcgctt tggatccta caagcacaaa   2700
gtgaacattg gcatgataga ccagtcccgg gatgcctctg ctgtcagcct gtcagaatcc   2760
aagtcaagtc aggattcctc tgactatagc actagtgaaa tgctggtcaa catgggaaac   2820
ttgcctctgg atgagttcta cccagctgtg tccatggtgg ccctgatgcg gatcttccga   2880
gaccagtcac tctctcatca tcacaccatg gttgtccagg ccatcacctt catcttcaag   2940
tccctgggac tcaaatgtgt gcagttcctg ccccaggtca tgcccacgtt ccttaacgtc   3000
attcgagtct gtgatggggc catccgggaa ttttgttcc agcagctggg aatgttggtg   3060
tcctttgtga agagccacat cagaccttat atggatgaaa tagtcaccct catgagagaa   3120
ttctgggtca tgaacacctc aattcagagc acgatcattc ttctcattga gcaaattgtg   3180
gtagctcttg ggggtgaatt taagctctac ctgccccagc tgatcccaca catgctgcgt   3240
gtcttcatgc atgacaacag cccaggccgc attgtctcta tcaagttact ggctgcaatc   3300
cagctgtttg gcgccaacct ggatgactac ctgcatttac tgctgcctcc tattgttaag   3360
ttgtttgatg cccctgaagc tccactgcca tctcgaaagg cagcgctaga gactgtggac   3420
cgcctgacgg agtccctgga tttcactgac tatgcctccc ggatcattca ccctattgtt   3480
cgaacactgg accagagccc agaactgcgc tccacagcca tggacacgct gtcttcactt   3540
gttttcagc tggggaagaa gtaccaaatt ttcattccaa tggtgaataa agttctggtg   3600
cgacaccgaa tcaatcatca gcgctatgat gtgctcatct gcagaattgt caagggatac   3660
acacttgctg atgaagagga ggatcctttg atttaccagc atcggatgct taggagtggc   3720
caagggggatg cattggctag tggaccagtg gaaacaggac ccatgaagaa actgcacgtc   3780
agcaccatca acctccaaaa ggcctggggc gctgccagga gggtctccaa agatgactgg   3840
ctggaatggc tgagacggct gagcctggag ctgctgaagg actcatcatc gccctccctg   3900
cgctcctgct gggccctggc acaggcctac aacccgatgg ccaggatct cttcaatgct   3960
gcatttgtgt cctgctggtc tgaactgaat gaagatcaac aggatgagct catcagaagc   4020
atcgagttgg ccctcacctc acaagacatc gctgaagtca cacagaccct cttaaacttg   4080
gctgaattca tggaacacag tgacaagggc cccctgccac tgagagatga caatggcatt   4140
```

-continued

| | |
|---|---|
| gttctgctgg gtgagagagc tgccaagtgc cgagcatatg ccaaagcact acactacaaa | 4200 |
| gaactggagt tccagaaagg ccccaccccct gccattctag aatctctcat cagcattaat | 4260 |
| aataagctac agcagccgga ggcagcggcc ggagtgttag aatatgccat gaaacacttt | 4320 |
| ggagagctgg agatccaggc tacctggtat gagaaactgc acgagtggga ggatgccctt | 4380 |
| gtggcctatg acaagaaaat ggacaccaac aaggacgacc cagagctgat gctgggccgc | 4440 |
| atgcgctgcc tcgaggcctt gggggaatgg ggtcaactcc accagcagtg ctgtgaaaag | 4500 |
| tggaccctgg ttaatgatga acccaagcc aagatggccc ggatggctgc tgcagctgca | 4560 |
| tggggtttag gtcagtggga cagcatggaa aatacacct gtatgatccc tcgggacacc | 4620 |
| catgatgggg cattttatag agctgtgctg gcactgcatc aggacctctt ctccttggca | 4680 |
| caacagtgca ttgacaaggc cagggacctg ctggatgctg aattaactgc gatggcagga | 4740 |
| gagagttaca gtcgggcata tggggccatg gtttcttgcc acatgctgtc cgagctggag | 4800 |
| gaggttatcc agtacaaact tgtccccgag cgacgagaga tcatccgcca gatctggtgg | 4860 |
| gagagactgc agggctgcca gcgtatcgta gaggactggc agaaaatcct tatggtgcgg | 4920 |
| tcccttgtgg tcagccctca tgaagacatg agaacctggc tcaagtatgc aagcctgtgc | 4980 |
| ggcaagagtg gcaggctggc tcttgctcat aaaactttag tgttgctcct gggagttgat | 5040 |
| ccgtctcggc aacttgacca tcctctgcca acagttcacc ctcaggtgac ctatgcctac | 5100 |
| atgaaaaaca tgtggaagag tgcccgcaag atcgatgcct tccagcacat gcagcatttt | 5160 |
| gtccagacca tgcagcaaca ggcccagcat gccatcgcta ctgaggacca gcagcataag | 5220 |
| caggaactgc acaagctcat ggcccgatgc ttcctgaaac ttggagagtg gcagctgaat | 5280 |
| ctacagggca tcaatgagag cacaatcccc aaagtgctgc agtactacag cgccgccaca | 5340 |
| gagcacgacc gcagctggta caaggcctgg catgcgtggg cagtgatgaa cttcgaagct | 5400 |
| gtgctacact acaaacatca gaaccaagcc cgcgatgaga agaagaaact gcgtcatgcc | 5460 |
| agcggggcca acatcaccaa cgccaccact gccgccacca cggccgccac tgccaccacc | 5520 |
| actgccagca ccgagggcag caacagtgag agcgaggccg agagcaccga aacagccccc | 5580 |
| accccatcgc cgctgcagaa aaggtcact gaggatctgt ccaaaaccct cctgatgtac | 5640 |
| acggtgcctg ccgtccaggg cttcttccgt tccatctcct tgtcacgagg caacaacctc | 5700 |
| caggatacac tcagagttct caccttatgg tttgattatg gtcactggcc agatgtcaat | 5760 |
| gaggccttag tggaggggt gaaagccatc cagattgata cctggctaca ggttatacct | 5820 |
| cagctcattg caagaattga tacgcccaga cccttggtgg gacgtctcat tcaccagctt | 5880 |
| ctcacagaca ttggtcggta ccacccccag gccctcatct acccactgac agtggcttct | 5940 |
| aagtctacca cgacagcccg gcacaatgca gccaacaaga ttctgaagaa catgtgtgag | 6000 |
| cacagcaaca ccctggtcca gcaggccatg atggtgagcg aggagctgat ccgagtggcc | 6060 |
| atcctctggc atgagatgtg gcatgaaggc ctggaagagg catctcgttt gtactttggg | 6120 |
| gaaaggaacg tgaaaggcat gtttgaggtg ctggagccct tgcatgctat gatggaacgg | 6180 |
| ggcccccaga ctctgaagga acatcctttt aatcaggcct atggtcgaga tttaatggag | 6240 |
| gcccaagagt ggtgcaggaa gtacatgaaa tcaggaatg tcaaggacct cacccaagcc | 6300 |
| tgggacctct attatcatgt gttccgacga atctcaaagc agctgcctca gctcacatcc | 6360 |
| ttagagctgc aatatgtttc cccaaaactt ctgatgtgcc gggaccttga attggctgtg | 6420 |
| ccaggaacat atgaccccaa ccagccaatc attcgcattc agtccatagc accgtctttg | 6480 |
| caagtcatca catccaagca gaggccccgg aaattgacac ttatgggcag caacggacat | 6540 |

```
gagtttgttt tccttctaaa aggccatgaa gatctgcgcc aggatgagcg tgtgatgcag    6600
ctcttcggcc tggttaacac ccttctggcc aatgacccaa catctcttcg gaaaaacctc    6660
agcatccaga gatacgctgt catcccttta tcgaccaact cgggcctcat tggctgggtt    6720
ccccactgtg acacactgca cgccctcatc cgggactaca gggagaagaa gaagatcctt    6780
ctcaacatcg agcatcgcat catgttgcgg atggctccgg actatgacca cttgactctg    6840
atgcagaagg tggaggtgtt tgagcatgcc gtcaataata cagctgggga cgacctggcc    6900
aagctgctgt ggctgaaaag ccccagctcc gaggtgtggt ttgaccgaag aaccaattat    6960
acccgttctt tagcggtcat gtcaatggtt gggtatattt taggcctggg agatagacac    7020
ccatccaacc tgatgctgga ccgtctgagt gggaagatcc tgcacattga ctttggggac    7080
tgctttgagg ttgctatgac ccagagaaag tttccagaga agattccatt tagactaaca    7140
agaatgttga ccaatgctat ggaggttaca ggcctggatg gcaactacag aatcacatgc    7200
cacacagtga tggaggtgct gcgagagcac aaggacagtg tcatggccgt gctggaagcc    7260
tttgtctatg acccccttgct gaactggagg ctgatgggaca caaataccaa aggcaacaag    7320
cgatcccgaa cgaggacgga ttcctactct gctggccagt cagtcgaaat tttggacggt    7380
gtggaacttg gagagccagc ccataagaaa acggggacca cagtgccaga atctattcat    7440
tctttcattg gagacggttt ggtgaaacca gaggccctaa ataagaaagc tatccagatt    7500
attaacaggg ttcgagataa gctcactggt cgggacttct ctcatgatga cactttggat    7560
gttccaacgc aagttgagct gctcatcaaa caagcgacat cccatgaaaa cctctgccag    7620
tgctatattg gctggtgccc tttctggtaa                                      7650

<210> SEQ ID NO 102
<211> LENGTH: 357
<212> TYPE: DNA
<213> ORGANISM: Homo sapiens

<400> SEQUENCE: 102
atgtccgggg gcagcagctg cagccagacc ccaagccggg ccatccccgc cactcgccgg      60
gtggtgctcg cgacggcgt gcagctcccg cccgggact acagcacgac ccccggcggc     120
acgctcttca gcaccacccc gggaggtacc aggatcatct atgaccggaa attcctgatg     180
gagtgtcgga actcacctgt gaccaaaaca ccccaagggg atctgcccac cattccgggg     240
gtcaccagcc cttccagtga tgagccccccc atggaagcca gccagagcca cctgcgcaat     300
agcccagaag ataagcgggc gggcggtgaa gagtcacagt ttgagatgga catttaa       357

<210> SEQ ID NO 103
<211> LENGTH: 363
<212> TYPE: DNA
<213> ORGANISM: Homo sapiens

<400> SEQUENCE: 103
atgtcctcgt cagccggcag cggccaccag cccagccaga gccgcgccat ccccaccccgc      60 accgtggcca tcagcgacgc cgcgcagcta cctcatgact attgcaccac gcccgggggg     120
acgctcttct ccaccacacc gggaggaact cgaatcattt atgacagaaa gtttctgttg     180
gatcgtcgca attctcccat ggctcagacc ccaccctgcc acctgcccaa tatcccagga     240
gtcactagcc ctggcacctt aattgaagac tccaaagtag aagtaaacaa tttgaacaac     300
ttgaacaatc acgacaggaa acatgcagtt ggggatgatg ctcagttcga gatggacatc     360
taa                                                                    363
```

```
<210> SEQ ID NO 104
<211> LENGTH: 654
<212> TYPE: DNA
<213> ORGANISM: Homo sapiens

<400> SEQUENCE: 104
atggcgactg tcgaaccgga aaccacccct actcctaatc ccccgactac agaagaggag      60
aaaacggaat ctaatcagga ggttgctaac ccagaacact atattaaaca tccoctacag     120 aacagatggg cactctggtt ttttaaaaat gataaaagca aaacttggca agcaaacctg     180
cggctgatct ccaagtttga tactgttgaa gactttggg ctctgtacaa ccatatccag      240
ttgtctagta atttaatgcc tggctgtgac tactcacttt ttaaggatgg tattgagcct     300
atgtgggaag atgagaaaaa caaacggggg ggacgatggc taattacatt gaacaaacag     360
cagagacgaa gtgacctcga tcgcttttgg ctagagacac ttctgtgcct tattggagaa     420
tcttttgatg actacagtga tgatgtatgt ggcgctgttg ttaatgttag agctaaaggt     480
gataagatag caatatggac tactgaatgt gaaaacagag aagctgttac acatataggg     540
agggtataca aggaaaggtt aggacttcct ccaaagatag tgattggtta tcagtcccac     600
gcagacacag ctactaagag cggctccacc actaaaaata ggtttgttgt ttaa           654
```

CELL-BASED ASSAY FOR DETERMINING MTOR ACTIVITY

CROSS REFERENCE TO RELATED APPLICATION

This application is a Divisional of U.S. application Ser. No. 15/430,153, filed Feb. 10, 2017, which claims the benefit under 35 U.S.C. § 119(e) to U.S. Provisional Application No. 62/432,935, filed Dec. 12, 2016, the contents of which are incorporated herein by reference in their entirety.

SEQUENCE LISTING

Filed in U.S. application Ser. No. 15/430,153, filed Feb. 10, 2017, via the EFS-Web was an ASCII text file containing the sequence listing, which is named "MDL_00064P_Seq_Listing_20161117_ST25", which was created on Dec. 12, 2016, and contains 37 kilobytes; said ASCII text file is incorporated herein by reference.

FIELD OF THE INVENTION

The present invention generally relates to a cell-based assay useful for determining the activity of mTOR and its variants. The novel cell-based assay is useful in screening mTOR inhibitors.

BACKGROUND OF THE INVENTION mTOR (mammalian target of rapamycin) was first identified in 1993 as the protein target of rapamycin (TOR2) and an essential phosphatidylinositol 3-kinase (PI3K) homolog (Kunz et al., 1993). mTOR is a serine/threonine kinase and regulates protein translation and progression from G1 to S phase of the cell cycle (Kuruvilla et al., 1999). mTOR is essential for cell survival because it promotes protein translation, cell proliferation, and growth.

MTOR gene knock-out leads to cell arrest at G1 phase and halts cell proliferation and growth (Murakami et al., 2004; Zhang et al., 2000; Kunz et al., 1993; Brown et al., 1994; Kuruvilla, et al., 1999). The mTOR inhibitor rapamycin (first identified in 1975 by Vezina et al. as an antifungal antibiotic isolated from *Streptomyces hydroscopicus*) and certain of its analogs (also known as rapalogs) have been FDA approved and used as a treatment for tumors (such as renal cell carcinoma, mantle cell lymphoma, and breast cancer), as these compounds inhibit mTOR-mediated phosphorylation and subsequent downstream cell growth and proliferation.

With the growing utilization of rapid sequencing technology, many human tumors (5-10%) have been found to contain somatic mutations in the MTOR gene (Grabiner et al., 2014). There are 463 reported somatic mutations in the MTOR gene in the COSMIC (Catalogue of Somatic Mutations in Cancer) database. The use of rapid sequencing technology such as Whole Genome Sequencing (WGS) or Next Generation Sequencing (NGS) is expected to permit identification of genetic variants that may alter treatment of genetically complex diseases, thereby promoting personalized medicine. However, the massive genome information lacks the support of interpretation because the phenotypic effects of the gene mutations are not known. The current knowledge of mutations in the MTOR gene is mostly limited to some associations with increased mTOR activity. Certain MTOR gene mutations are known to be associated with an increase in mTOR activity, thereby increasing the rate of tumor growth. (Grabiner et al., 2014). Rapamycin treatment is a cancer therapy that is targeted to reduce the mTOR activity. Information relating to specific MTOR gene mutations that confer resistance to rapamycin treatment is lacking. Additionally, ATP-competitive inhibitors of mTOR have been developed and are currently in clinical trials (Thoreen et al., 2009; Schenone et al., 2011). However, mutations in the MTOR gene can also decrease the efficacy of these newer medications (Wu et al., 2015; Rodrik-Outmezguine et al., 2016).

Several methods are available that purportedly determine mTOR activity. One such method involves detection of the phosphorylation status of the P70 S6 kinase (AlphaScreen SureFire assay, PerkinElmer). Another method relates to an ELISA that measures the kinase activity of mTOR immunoprecipitated from cell lysates (K-LISA mTOR Activity Kit, EMD Millipore). However, these two methods have significant drawbacks and do not accurately measure the effectiveness of a particular mTOR inhibitor as it related to the downstream function of mTOR activity, which is multifaceted. Another known method includes the FKBP12-FRB (FKBP12-Rapamycin binding domain of mTOR) split luciferase assay that measures emission of light signals upon binding of FKBP12 to FRB domain when rapamycin is active in reducing mTOR activity (Luker et al., 2004; Dixon et al., 2016). However, this particular method is hindered by the use of a small portion of mTOR, thus precluding its effective assessment of the entire MTOR gene. In other words, this method precludes an effective assessment of all MTOR genetic variants and is limited to evaluating the ability of rapamycin to bind to a small portion of mTOR. These methods represent an inaccurate depiction of the effectiveness of whether a particular inhibitor can reduce mTOR activity, thereby inhibiting the tumor growth.

Accordingly, there is a continuing need to develop a rapid cell-based assay that measures mTOR activity and the effectiveness of inhibitors against alterations in mTOR activity due to somatic mutations in the MTOR gene.

SUMMARY OF THE INVENTION

In one aspect the present invention concerns a method of determining whether a mTOR variant is sensitive to treatment with a mTOR inhibitor in a cell, comprising the steps of:
a. preparing a first cDNA of a mTOR variant, said mTOR variant containing at least one mutation as compared to wild-type MTOR;
b. transfecting said first cDNA into a mammalian cell, said cell having:
 i. a first construct comprising a second cDNA, said second cDNA is selected from the group consisting of cDNA encoding 4E-BP1 protein and cDNA encoding 4E-BP2 protein, said second cDNA is linked at its N-terminus to a first portion of a luciferase gene, and a second construct comprising a third cDNA encoding eIF4E, said third cDNA is linked at its N-terminus to a second portion of a luciferase gene,
  wherein when the protein products of said first construct and said second construct are expressed they interact to form a complex which generates a light emission upon addition of a luciferase substrate; and
 ii. a knockdown or knockout of endogenous 4E-BP1 or 4E-BP2;
c. exposing said transfected cell to a mTOR inhibitor;

d. repeating steps a. and b. then exposing the cell so transfected to a vehicle; and
e. determining whether said mTOR variant is sensitive to treatment with said mTOR inhibitor by measuring the generated light emission,
   wherein an increase in light emission of said transfected cell exposed to a mTOR inhibitor relative to that of said transfected cell exposed to a vehicle is indicative of mTOR variant sensitivity to treatment.

In another aspect the present invention concerns a method of determining whether a mTOR variant is sensitive to treatment with rapamycin or a rapalog in a cell, comprising the steps of:
a. preparing a first cDNA containing a mTOR variant;
b. transfecting said first cDNA into a mammalian cell, said cell having:
   a first construct comprising a second cDNA, said second cDNA selected from the group consisting of cDNA encoding 4E-BP1 protein and cDNA encoding 4E-BP2 protein, said second cDNA is linked at its N-terminus to a first portion of a luciferase gene, and a second construct comprising a third cDNA encoding eIF4E protein linked at its N-terminus to a second portion of said luciferase gene,
      wherein when the protein products of said first construct and said second construct are expressed they interact to form a complex which generates a light emission upon addition of a luciferase substrate; and
c. exposing said transfected cell to rapamycin or a rapalog;
d. repeating steps a and b, then exposing the cell so transfected to a vehicle; and
e. determining whether said mTOR variant is sensitive to treatment with said rapamycin or rapalog by measuring the generated light emission,
   wherein an increase in light emission of said transfected cell exposed to rapamycin or a rapalog relative that of said transfected cell exposed to a vehicle is indicative of mTOR variant sensitivity to treatment.

In another aspect the present invention concerns a method of determining the kinase activity a mTOR variant in a cell, comprising the steps of:
a. preparing a cDNA of a mTOR variant, said mTOR variant is suspected of having an altered kinase activity relative to a wild-type mTOR;
b. preparing a cDNA of wild-type mTOR;
c. providing a cell, said cell having, a first construct comprising cDNA selected from the group consisting of cDNA encoding 4E-BP1 protein and cDNA encoding 4E-BP2 protein, said cDNA in the first construct is linked at its N-terminus to a first portion of a luciferase gene, and a second construct comprising a cDNA encoding eIF4E protein, said cDNA in the second construct is linked at its N-terminus to a second portion of said luciferase gene,
   wherein when the protein products of said first construct and said second construct are expressed they interact to form a complex which generates a light emission upon addition of a luciferase substrate;
d. transfecting said mTOR variant prepared in step a into a cell provided in step c;
e. transfecting said wild-type cDNA prepared in step b into a different cell provided in step c;
f. measuring the light emission in said transfected cell having said mTOR variant in step d and said transfected cell having wild type mTOR in step e; and
g. determining if there is an increase or decrease in kinase activity as evidenced by a decrease or increase, respectively, in light emission in said cell transfected with said mTOR variant as compared to that in said cell transfected with said wild-type mTOR.

In another aspect the invention concerns a method of determining whether a tumor cell is sensitive to treatment with rapamycin or a rapalog, comprising the steps of:
a. obtaining a tumor cell;
b. transfecting into said tumor cell: a first construct comprising a cDNA selected from the group consisting of cDNA encoding 4E-BP1 protein and cDNA encoding 4E-BP2 protein, said cDNA in the first construct is linked at its N-terminus to a first portion of a luciferase gene, and a second construct comprising a cDNA encoding eIF4E, said cDNA in the second construct is linked at its N-terminus to a second portion of said luciferase gene,
   wherein when the protein products of said first construct and said second construct are expressed they interact to form a complex which generates a light emission upon addition of a luciferase substrate;
c. exposing said transfected cell to rapamycin or a rapalog;
d. repeating steps a and b, then exposing said cell so transfected to a vehicle; and
e. determining whether said tumor cell is sensitive to treatment with said rapamycin or a rapalog by measuring an increase in light emission relative that of said vehicle.

In another aspect the present invention concerns a method of determining whether a compound inhibits mTOR activity in a cell, comprising the steps of:
a. providing a cell, said cell having:
   i. a genomic modification of at least one gene selected from the group consisting of EIF4EBP1 and EIF4EBP2; and
   ii. a first construct comprising a cDNA selected from the group consisting of cDNA encoding 4E-BP1 protein and cDNA encoding 4E-BP2 protein, said cDNA in the first construct is linked at its N-terminus to a first portion of a luciferase gene, and a second construct comprising a cDNA encoding eIF4E protein, said cDNA in the second construct is linked at its N-terminus to a second portion of said luciferase gene,
      wherein when the protein products of said first construct and said second construct are expressed they interact to form a complex which generates a light emission upon addition of a luciferase substrate;
b. exposing said cell to a compound;
c. repeating step a, then exposing the cell to a vehicle;
d. measuring the light emissions in said exposed cells after step b and step c;
e determining whether said compound inhibits mTOR activity in said cell as indicated by an increase in said measured light emission relative that of the cell exposed to a vehicle.

In another aspect the present invention concerns a method of determining whether a 4E-BP1 variant or a 4E-BP2 variant is sensitive to treatment with a mTOR inhibitor in a cell, comprising the steps of:

a. preparing a first construct comprising a cDNA selected from the group consisting of cDNA encoding a 4E-BP1 variant protein and cDNA encoding a 4E-BP2 variant protein, said cDNA in the first construct is linked at its N-terminus to a first portion of a luciferase gene, and preparing a second construct comprising a cDNA encoding eIF4E protein, said cDNA of the second construct is linked at its N-terminus to a second portion of a luciferase gene;
b. transfecting said first construct and said second construct into a mammalian cell,
    wherein when the protein products of said first construct and said second construct are expressed they interact to form a complex which generates a light emission upon addition of a luciferase substrate;
c. exposing said cell to a mTOR inhibitor;
d. repeating steps a and b, then exposing the cell so transfected to a vehicle; and
e. determining whether said 4E-BP1 variant protein or said 4E-BP2 variant protein is sensitive to treatment with said mTOR inhibitor by measuring the generated light emissions,
    wherein an increase in light emission of the cell exposed to the mTOR inhibitor relative to that of the cell exposed to the vehicle is indicative of 4E-BP1 variant protein or 4E-BP2 variant protein sensitivity to treatment.

In another aspect the present invention concerns a method of determining whether a 4E-BP variant is capable of functioning in its capacity of binding eIF4E in a cell, comprising the steps of:
a. preparing a first construct comprising a cDNA of a 4E-BP variant, said 4E-BP variant containing at least one mutation as compared to wild-type 4E-BP, wherein said cDNA in the first construct is linked at its N-terminus to a first portion of a luciferase gene, and preparing a second construct containing a cDNA encoding eIF4E protein, said cDNA in the second construct is linked at its N-terminus to a second portion of said luciferase gene;
b. transfecting said first construct and said second construct into a mammalian cell,
    wherein when the protein products of said first construct and said second construct are expressed they interact to form a complex which generates a light emission upon addition of a luciferase substrate;
c. repeating steps a and b wherein said first construct contains cDNA of wild-type 4E-BP;
d. determining whether said 4E-BP variant is capable of functioning in its capacity of binding eIF4E by comparing the light signal generated by said cell transfected with 4E-BP variant compared to that of the cell transfected with wild-type 4E-BP.

In the methods of the invention it is preferred that the first construct comprises cDNA of SEQ. ID. NO: 2 or SEQ. ID. NO: 3 and/or that the second construct comprises cDNA of SEQ. ID. NO: 1.

In another aspect, the present invention concerns novel cell lines comprising a plurality of cells wherein the cells contain a first construct comprising a first cDNA selected from the group consisting of cDNA encoding 4E-BP1 protein and cDNA encoding 4E-BP2 protein, said first cDNA is linked at its N-terminus to a first portion of a luciferase gene, said first construct having cDNA preferably selected from the group consisting of SEQ. ID. NO: 2 or SEQ. ID. NO: 3; and a second construct comprising a second cDNA encoding eIF4E protein, said second cDNA is linked at its N-terminus to a second portion of a luciferase gene, said second construct preferably having cDNA of SEQ. ID. NO: 1, wherein when the protein products of said first construct and said second construct interact a complex is formed which generates a light emission in the presence of a luciferase substrate. In one embodiment the cell line is stable. In another embodiment the cell line is a single-cell clone. In yet another embodiment the cell line is a clonal pool.

BRIEF DESCRIPTION OF THE DRAWINGS

FIG. 1A depicts uninhibited mTOR activity in a cell. When mTOR is active, mTOR phosphorylates 4E-BP1, thereby preventing an interaction between 4E-BP1 and eIF4E. Free eIF4E induces translation. FIG. 1A also shows the attachments of the Large BiT (LB) to 4E-BP1 and the Small BiT (SB) to eIF4E. FIG. 1B depicts how the presence of the inhibitor rapamycin blocks mTOR, enabling LB-4E-BP1 and SB-eIF4E to interact, which would prevent translation.

FIG. 2A, FIG. 2B, and FIG. 2C depict the DNA sequences for the open-reading frames (ORFs) of the Small BiT (SB)-eIF4E (SEQ. ID. NO: 1), the Large BiT (LB)-4E-BP1 (SEQ. ID. NO: 2), and the Large BiT (LB)-4E-BP2 (SEQ. ID. NO: 3), respectively. FIG. 2D, FIG. 2E, and FIG. 2F depict the amino acid sequences for the ORFs of the Small BiT (SB)-eIF4E (SEQ. ID. NO: 4), the Large BiT (LB)-4E-BP1 (SEQ. ID. NO: 5), and the Large BiT (LB)-4E-BP2 (SEQ. ID. NO: 6), respectively.

FIG. 9A depicts the four CRISPR construct pairs of 4E-BP1 against wild-type 4E-BP1 in HEK293 cells. FIG. 9B depicts the four CRISPR construct pairs of 4E-BP2 against wild-type 4E-BP2 in HEK293 cells.

FIG. 10A depicts single cell clone ("3A1") with 4E-BP1/4E-BP2 deletion. The 3A1 dKO (double knockout) clone was transiently transfected with SB-eIF4E/LB-4E-BP1 and treated with rapamycin, AZD2014 (AstraZeneca), or INK128 (Intellikine). FIG. 10B depicts the 3A1 dKO clone transiently transfected with SB-eIF4E/LB-4E-BP2 and treated with rapamycin, AZD2014, or INK128. FIG. 10C depicts single cell clone ("1C3") with 4E-BP1/4E-BP2 deletion. The 1C3 dKO clone was transiently transfected with SB-eIF4E/LB-4E-BP1 and treated with rapamycin, AZD2014, or INK128. FIG. 10D depicts the 1C3 dKO clone transiently transfected with SB-eIF4E/LB-4E-BP2 and treated with rapamycin, AZD2014, or INK128.

FIG. 19A depicts the effects of INK128 on the L2185A mutation (mutation that reduces binding of ATP-competitive mTOR inhibitors) in the parent single-cell clone 3A1 with 4E-BP1 and 4E-BP2 deletion, stably expressing SB-eIF4E, and transiently expressing LB-4E-BP2 and WT or L2185A mTOR. FIG. 19B depicts the effects of INK128 on the L2185A mutation in the E2 clone with CRISPR-mediated genomic modifications to the MTOR gene, stably expressing SB-eIF4E and transiently expressing LB-4E-BP2 and WT or L2185A mTOR. FIG. 19C depicts the effects of INK128 on the L2185A mutation in the B10 clone with CRISPR-mediated genomic modifications to the MTOR gene, stably expressing SB-eIF4E and transiently expressing LB-4E-BP2 and WT or L2185A mTOR. When taken together with FIG. 17, a minimization of the endogenous effect of mTOR with E2 and B10 clones is apparent. The B10 cell line was chosen because it has the least endogenous mTOR activity.

DETAILED DESCRIPTION OF THE INVENTION

Figure 1A:
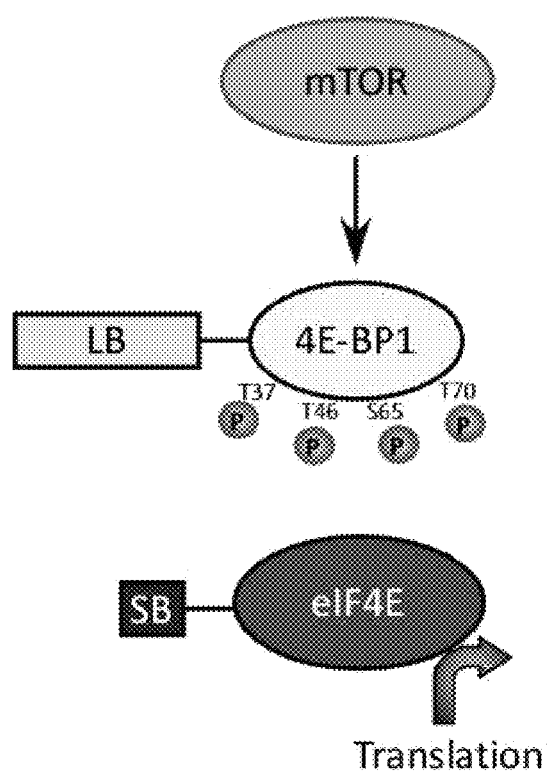
FIG. 1A and FIG. 1B show the present assay design and function.

The present invention can be better understood from the following description of preferred embodiments, taken in conjunction with the accompanying drawings. It should be apparent to those skilled in the art that the described embodiments of the present invention provided herein are merely exemplary and illustrative and not limiting. Numerous embodiments or modifications thereof are contemplated as falling within the scope of the present invention and equivalents thereto. All publications, patent applications, patents, and other references mentioned herein are incorporated by reference in their entirety.

Definitions

Various terms used in this specification shall have the definitions set out herein.

As used herein, the term "A," "T," "C", and "G" refer to adenine, thymine, cytosine, and guanine as a nucleotide base, respectively.

As used herein, the terms "complement" or "complementation" refer to two halves of a protein coming into structural complex by binding to each other and producing a functional protein. "Complement" may also be used in reference to nucleic acids as in "reverse complement" to indicate an opposing strand of nucleic acids that resides in a particular sequence to bind to a polynucleotide.

As used herein, the term "double-stranded oligonucleotide" refers to short polynucleotide sequences bound to the reverse complement nucleic acids.

As used herein, the term "double-mutant" refers to two independent mutations in a single cDNA or protein.

As used herein, the term "MTOR" refers to the gene (SEQ. ID. NO: 101) which transcribes RNA that translates into the mTOR protein.

As used herein, the term "mTOR" refers to mammalian target of rapamycin (mTOR), an essential phosphatidylinositol 3-kinase (PI3K) homolog. mTOR is a family member of phosphatidylinositol 3-kinase (PI3-kinase) related kinase.

As used herein, the term "TOR2" refers to the target of rapamycin (TOR2) and mTOR homolog, originally discovered in Saccharomyces cerevisiae.

As used herein the term "wild-type" or "WT" is a term of the art understood by skilled persons and means the typical form of an organism, strain, gene or characteristic as it occurs in nature as distinguished from mutant, variant, or modified forms.

As used herein the term "variant" means the exhibition of qualities that have a pattern that deviates from what occurs in nature or is distinct from the predominant form that occurs in nature. For the purposes of this application, the term "variant" can refer to non-dominant gene sequences, mutations or changes in resulting amino acid sequence. For purposes of this application, when the gene name is used in reference to a variant, it refers to a variant found within the DNA. When a protein name is used in reference to a variant, it refers to a DNA change that results in a "variant" amino acid change that may alter protein characteristics.

As used herein, the term "functional variant" refers to variants in a protein's amino acid sequence that acts functionally like WT protein.

As used herein, the term "eIF4E" refers to eukaryotic translation initiation factor 4E (SEQ. ID. NO: 104) and functional variants of eIF4E.

As used herein, the term "4E-BP1" refers to eIF4E binding protein 1 (SEQ. ID. NO: 102) and functional variants of 4E-BP1.

As used herein, the term "4E-BP2" refers to eIF4E binding protein 2 (SEQ. ID. NO: 103) and functional variants of 4E-BP2.

As used herein, the term "4E-BP" refers to collectively 4E-BP1, 4E-BP2, and associated family members, as determined by homology and function.

As used herein, the term "vehicle" refers to a solvent of a compound. For purposes of this application the term "vehicle" is used as a negative control in the absence of compound.

As used herein, the term "CRISPR" refers to Clustered regularly interspaced short palindromic repeats, which are sequences used by CRISPR associated proteins (Cas) for the purpose of recognizing and cutting genetic elements of polynucleotides. CRISPR/Cas9 uses sgRNA as a recognition sequence for identifying where the Cas9 will bind and cut the genetic element. For the purposes of the examples of this specification, CRISPR/Cas9 and sgRNA were used for genomic modifications of EIF4EBP1, EIF4EBP2, and MTOR genes.

As used herein, the term "siRNA" refers to refers to a small interfering RNA. RNA interference refers to the process of sequence-specific post-transcriptional gene silencing in a cell or an animal mediated through binding of short interfering RNA.

As used herein, the term "sgRNA" refers to single-guide RNA used as a recognition sequence for the CRISPR/Cas9 binding.

As used herein, the term "HEK293" refers to an immortalized cell line derived from human embryonic kidney cells.

As used herein, the term "MCF-7" refers to a breast cancer cell line isolated from a 69-year-old woman.

As used herein, the term "cancer" refers to a malignant neoplastic disease. Most cancers are characterized by hyperproliferation of a cell population.

As used herein, the term "tumor cell" refers to a malignant neoplastic cell.

As used herein, the term "luciferase activity" refers to the use of a luciferase protein or reporter to assess the amount of luciferase complementation resulting from two-parts or halves of a luciferase protein coming into complex or luciferase protein generated by transcriptional activity in a cell under the control of a promoter of interest. The activity is measured by addition of a substrate that binds to the luciferase protein and emits a light signal that can be measured using a luminometer.

As used herein, the term "promoter" refers to a region of the DNA that facilitates the transcription of a particular gene.

As used herein, the term "open-reading frame" refers to a continuous stretch of nucleotides where groups of three can be transcribed into amino acids that result in production of a protein. The stretch of nucleotides typically starts with "ATG" to indicate a methionine amino acid that initiates the translation process.

As used herein, the terms "NanoBiT," "Small BiT" and "Large BiT" refer to a split-luciferase complementation assay system consisting of two parts of a luciferase-based protein, where the Small BiT consists of 11 amino acids and the Large BiT consists of a 17.6 kDa protein. When the Small BiT and the Large BiT come into complex, the full luciferase is formed and can emit a light signal with the addition of a substrate.

As used herein, the terms "relative light units" or "RLU" refer to as the emitted light from a sample in a non-standardized scale as determined by a luminometer. The term "relative" indicates the units observed during the particular experiment and cannot be compared directly across experiments without standardization.

As used herein, the term "construct" refers to a plasmid or polynucleotide containing cDNA to encode for a given protein. As defined in the current application, the terms "first construct" and "second construct" refer to the complete plasmid and cDNA for encoding the expression of the protein linked to a portion of the luciferase gene. For the purposes of the current application, plasmids containing CRISPR/Cas9 and designed sgRNAs are also referred to as "constructs." "Constructs" can also refer to polynucleotides having the necessary components to express a desired protein.

As used herein, "expression" or "expressed" refers to the processes by which a polynucleotide is transcribed from a DNA template (such as into and mRNA or other RNA transcript) and further processed or translated into peptides, polypeptides, or proteins. Transcripts and encoded polypeptides may be collectively referred to as "gene product." If the polynucleotide is derived from genomic DNA, expression may include differential splicing of the mRNA in a eukaryotic cell leading to different forms of peptides or protein products.

As used herein, the terms "stable expression" or "stably expressing" refer to the a cell line or group of cells that express a given protein for a period greater than 1 week, normally resulting in permanent expression of that protein over months.

As used herein, the term "knockout" or "deletion" refers to the lack of expression of a given protein. For the purposes of the examples of current application, the knockout or deletion of 4E-BP1 and 4E-BP2 was created through genomic modifications resulting in a premature termination of the 4E-BP1 and 4E-BP2 translation into protein, thereby effectively "knocking out" or "deleting" 4E-BP1 and 4E-BP2 expression.

As used herein, the term "knockdown" refers to a reduced expression of a given protein. For the purposes of the examples of the current application, the knockdown of mTOR was created through genomic modifications to the MTOR gene, resulting in reduced expression of mTOR relative to unmodified MTOR.

As used herein, the term "single-cell clone" refers to a cell line that is derived from a single cell.

As used herein, the term "clonal pools" refers to a cell line generated after transfection and/or selection, which is derived from multiple cells.

As used herein, the term "stable cell clone," "stable cell line," "stable cell pool," or stable cell system refers to the generation of cells using a selection method that specifically stably express a given protein. "Stable cell clone" is derived from a single cell with stable expression of a given protein. "Stable cell pool" is derived from multiple cells with stable expression of a given protein.

As used herein, the term "stable" refers to cells that have long-term (greater than 1 week and lasting months) alteration in protein expression, in the current application resulting from stable transfection or genetic modification.

As used herein, the term "parent" refers to the source cell line prior to additional modifications. For instance, the HEK293 cell line is "parent" to the "3A1" cell line with genomic modifications to EIF4EBP1 and EIF4EBP2, and the "3A1" cell line is parent to the "B10" cell line with genomic modifications to EIF4EBP1, EIF4EBP2, and MTOR.

As used herein, the term "transfection" refers to the process of getting a polynucleotide into a cell.

As used herein, the term "transiently transfected" refers to the process of getting a polynucleotide into a cell resulting in expression of a protein over a period from 12 hours to 7 days.

As used herein, the term "genomic PCR" refers to a polymerase chain reaction (PCR) performed on genomic DNA isolated from a given cell population. The PCR uses primers designed to amplify a specific size of polynucleotide based on qualities of the genomic DNA.

As used herein, the term "mTOR inhibitor" refers to a compound which prevents or reduces mTOR activity.

As used herein, the term "effective", in a specific context, refers to producing a response that results in an increase in luminescence in response to mTOR inhibitors that is similar to WT protein.

As used herein, the term "fold-change" refers to the luminescence observed with inhibitor or chemical treatment divided by the luminescence observed with vehicle only treatment.

As used herein "rapalog" refers to an analog of rapamycin such as temsirolimus, everolimus, deforolimus, and the like.

The present invention relates to mTOR variants sensitivity to treatment, tumor cell sensitivity to treatment, mTOR variants sensitivity to inhibitors and whether compounds inhibit mTOR activity in a cell. In one aspect, the present invention provides highly sensitive methods for determining whether a mTOR variant is sensitive to treatment using a mTOR inhibitor, rapamycin or a rapalog.

Methods include providing a stable cell system containing cDNA constructs with signaling capability to measure the functional interaction between mTOR variants and treatment with a mTOR inhibitor. The mTOR variants may include one or more mutations in the MTOR gene. Identification of the mTOR variants may be obtained from sequencing of a biological sample.

mTOR acts as a serine/threonine kinase that phosphorylates 4E-BP1 and 4E-BP2 (collectively termed 4E-BP). The 4E-BP1 phosphorylation occurs at 4 different sites and regulates the binding of 4E-BP to eIF4E. Binding of 4E-BP to eIF4E inhibits eukaryotic translation that would be promoted through eIF4E activity. However, mTOR-mediated phosphorylation of 4E-BP dissociates 4E-BP from eIF4E, thereby allowing translation to occur. When cells are treated with rapamycin and mTOR is inhibited, 4E-BP phosphorylation is prevented and allows for the 4E-BP/eIF4E complex that inhibits translation and decreases the growth and replication of the cell, thereby inhibiting cancer cells.

In one aspect, the present invention provides a method to determine mTOR activity using a cell based assay. The present cell based assay involves the use of a first cDNA construct and a second cDNA construct transfected into a cell. The first cDNA construct can contain a cDNA that encodes the protein of 4E-BP1 or it can contain a cDNA that encodes the protein of 4E-BP2. The second cDNA construct contains a cDNA that encodes the protein of eIF4E. The first cDNA is designed to link, preferably at the N-terminus of the cDNA encoding the desired 4E-BP protein to a first portion of a luciferase gene. Collectively, the 4E-BP cDNA linked to a first portion of the luciferase gene is the first construct. The second cDNA is designed to link, preferably at the N-terminus of the cDNA encoding eIF4E to a second portion of a luciferase gene. Collectively, the eIF4E cDNA linked to a second portion of the luciferase gene is the second construct. Upon transfection, the first cDNA construct produces 4E-BP1 or 4E-BP2 protein linked to a first portion of the luciferase protein in the cell. Similarly, the second cDNA construct produces the eIF4E protein linked to a second portion of the luciferase protein in the cell. The protein product generated from the first construct interacts with the protein product generated from the second construct to produce a light emission upon addition of a luciferase substrate. The present assay takes advantage of the protein products interaction between 4E-BP1 or 4E-BP2 with eIF4E. It is known that when mTOR is active it will phosphorylate 4E-BP proteins, such that the phosphorylation modulates the protein binding of 4E-BP with eIF4E. The present assay also takes advantage of the activity of mTOR whereas inhibition of mTOR prevents the phosphorylation of 4E-BP proteins, thereby facilitating the protein interaction between 4E-BP and eIF4E. The interaction between the two protein products promote generation of light emission and therefore allows for indirect measurement of mTOR activity.

In certain embodiments, the cell can be a mammalian cell. Preferably the cell can be a human cell. Examples of cells include, but are not limited to, a breast cell, a kidney cell, a liver cell, a leukocyte cell, a brain cell, an endometrial cell, a colo-rectal cell, a renal cell, and the like. In certain embodiments, the cell is a tumor cell. In certain embodiments, the cell has already been transfected and contains a first cDNA and a second cDNA. In a certain embodiment of the invention the cells have a mTOR variant, a first cDNA and a second cDNA. In certain embodiments the cells have genomic modifications of EIF4EBP1 or EIF4EBP2, which may result in a knock down or knockout of 4E-BP1 and/or 4E-BP2 protein. Combinations of genetic modifications are also within the scope of the invention. In certain embodiments, the transfected cells contain a first cDNA construct encoding 4E-BP1 linked to a first portion of the luciferase gene (e.g., SEQ. ID. NO: 2) and a second cDNA encoding eIF4E linked to a second portion of the luciferase gene (e.g., SEQ. ID. NO: 1). In another embodiment the transfected cells contain a first cDNA construct encoding 4E-BP2 linked to a first portion of the luciferase gene (e.g., SEQ. ID. NO: 3) and a second cDNA encoding eIF4E linked to a second portion of the luciferase gene (e.g., SEQ. ID. NO: 1). In another embodiment, the transfected cells contain a first cDNA construct encoding a 4E-BP1 variant linked to a first portion of the luciferase gene and a second cDNA encoding eIF4E linked to a second portion of the luciferase gene. In another embodiment the transfected cells contain a first cDNA construct encoding a 4E-BP2 variant linked to a first portion of the luciferase gene and a second cDNA encoding eIF4E linked to a second portion of the luciferase gene.

In the assay cells of the invention in one embodiment the cells have a genetic modification of endogenous MTOR resulting in reduced expression and/or activity of mTOR protein relative to wild-type mTOR. In another embodiment the cells are stably transfected with the second construct (e.g., SB-eIF4E). In another embodiment the cells are transiently transfected with the first construct (e.g., LB-4E-BP).

The parent cells of the cell lines of the invention are mammalian cells, such as rat, mouse, hamster, monkey, and human cells. Specific examples of parent cell lines of the invention include HEK293 (human embryo kidney), MCF-7 (human breast cancer), HeLa (human cervix epithelial carcinoma), HT29 (human colon adenocarcinoma grade II), A431 (human squamous carcinoma), IMR 32 (human neuroblastoma), K562 (human chronic myelogenous leukemia), U937 (human histiocytic lymphoma), MDA-MB-231 (Human breast adenocarcinoma), SK-N-BE(2) (human neuroblastoma), SH-SY5Y (human neuroblastoma), HL60 (human promyelocytic leukemia), CHO (Chinese hamster ovary), COS-7 (African green monkey kidney, SV40 transformed), S49 (mouse lymphoma), Ltk (mouse C34/connective tissue), NG108-15 (mouse neuroblastoma and Rat glioma hybrid), B35 (rat neuroblastoma), B50 (rat nervous tissue), B104 (rat nervous tissue), C6 (rat glial tumor), Jurkat (human leukemic T cell lymphoblast), BHK (baby Syrian hamster kidney), Neuro-2a (mouse albino neuroblastoma), NIH/3T3 (mouse embryo fibroblast), A549 (human adenocarcinoma alveolar epithelial), Be2C (human neuroblastoma), SW480 (human colon adenocarcinoma), Caco2 (human epithelial colorectal adenocarcinoma), THP1 (human acute monocyte leukemia), IMR90 (human fetal lung fibroblast), HT1080 (human fibrosarcoma), LnCap (human prostate adenocarcinoma), HepG2 (human liver carcinoma) PC12 (rat adrenal gland phaeochromocytoma), or SK-BR-3 (human breast cancer) cells. In another embodiment, the parent cells are U20S (human osteosarcoma) cells. In another embodiment, the parent cells are NCI-60 (human tumor) cell lines, such as, A549, EKVX, T47D, or HT29.

In certain embodiments, the first cDNA encoding 4E-BP1 protein is linked to a first portion of the luciferase gene, together creating a first construct having SEQ. ID. NO: 2. In certain embodiments, the first cDNA encoding 4E-BP2 protein is linked to a first portion of the luciferase gene, together creating a first construct having SEQ. ID. NO: 3. In certain embodiments, the first cDNA is cDNA encoding 4E-BP3 protein is linked to a first portion of the luciferase gene, together creating a first construct. In certain embodiments, the second cDNA encoding eIF4E protein is linked to a second portion of the luciferase gene, together creating the second construct having SEQ. ID. NO: 1. After transfection, the protein products generated from the first and second construct interact to produce a light emission upon addition of a luciferase substrate. The constructs may include other components desirable for adequate expression of the desired protein(s).

In certain embodiments the cDNA encoding for 4E-BP1 contains variants that distinguish 4E-BP1 from wild-type 4E-BP1. In certain embodiments the cDNA encoding for 4E-BP2 contains variants that distinguish 4E-BP2 from wild-type 4E-BP2. In certain embodiments the cDNA encoding for 4E-BP3 contains variants that distinguish 4E-BP3 from wild-type 4E-BP3. In certain embodiments the cDNA encoding for eIF4E contains variants that distinguish eIF4E from wild-type eIF4E.

The exact sequence and size of the first and second portions of the luciferase gene in the first and second constructs may vary provided that when the two portions of the luciferase gene are expressed in an assay cell, the protein products interact to generate a measurable light emission or light signal upon addition of a luciferase substrate. An example of a suitable two-subunit system for detection of protein interaction utilizing luminescent enzymes is Nano-Luc® Binary Technology (NanoBiT).

The present assay can be used in personalized medicine. When genome information is obtained relating to MTOR sequences, one skilled in the art can prepare a cDNA based on the MTOR gene sequence information. The generated cDNA may be a unique cDNA equivalent to a variant or wild-type sequence of the MTOR gene of an individual. In one aspect, the present invention provides an assay to test patient variants in the MTOR gene, as identified by next generation sequencing (NGS), thus determining potentially hyperactive and/or inhibitor resistant mutations. One advantage of the present assay is to transfect the generated cDNA into an assay cell containing a first cDNA encoding 4E-BP1 or 4E-BP2 and a second cDNA encoding eIF4E. The first cDNA and the second cDNA each link at its N-terminus to a separate portion of a luciferase gene, creating linked protein products when the cDNAs are expressed in a cell. When protein products of the two portions of the luciferase gene interact, a signal is created which serves as an indirect measurement of the activity of mTOR produced by the variant or wild-type sequence of the MTOR gene.

In certain embodiments, the cDNA may be transiently transfected into the cell. In certain embodiments the cDNA may be stably transfected into the cell. In certain embodiments, cDNAs may be added to the cell by a combination of transient transfection and stable transfection. In one embodiment the cDNA of mTOR or the mTOR variant is transiently transfected.

In certain embodiments, the mTOR variant contains one mutation. In certain embodiments, the mTOR variant may contain two mutations. In certain embodiments, the mTOR variant may contain three mutations. In certain embodiments the mTOR variant may contain four or more mutations. Similarly, the 4E-BP variant can contain at least one mutation. For example, the 4E-BP variant can contain one, two, three, four or more mutations. Functional variants of eIF4E, 4E-BP1 and 4E-BP2 are those variants that are effective in performing the methods of the invention. These variants can be mutations or polymorphisms. Functional variants can be truncations, such as truncations of 30 amino acid residues or less, or 25 amino acid residues or less, or 20 amino acid residues or less. Examples of functional variants are shown in Table 2 and FIG. 22.

In certain embodiments, the luminescence or light signal is produced by a structural complementation reporter designed for protein to protein interactions such as Nano-Luc® Binary Technology (NanoBiT). In certain embodiments, the luminescence signal is produced by Firefly or Renilla Luciferase. In certain embodiments, the protein to protein interactions are measured by fluorescence signaling systems such as Fluorescence Resonance Energy Transfer (FRET) or by a combination luminescence signal such as Bioluminescence Resonance Energy Transfer (BRET).

In another aspect, the present invention provides a method to determine whether a particular mTOR variant is sensitive to treatment with mTOR inhibitors. The method involves preparing a first cDNA encoding a mTOR variant of interest followed by transfecting the first cDNA into a cell. The cell also is transfected with a second cDNA encoding 4E-BP1 or 4E-BP2, collectively 4E-BP, as well as a third cDNA encoding eIF4E. The second cDNA is linked at its N-terminus to a first portion of a luciferase gene and the third cDNA is linked at its N-terminus to a second portion of a luciferase gene. When the cell is exposed to a mTOR inhibitor, mTOR is inactivated, which allows 4E-BP and eIF4E to interact and facilitates their linked portions of the luciferase protein to come into complex and produce a light signal.

In certain embodiments, the transfected cells (i.e., the cells having the cDNA encoding a mTOR variant, a first construct containing cDNA encoding 4E-BP1 or 4E-BP2 linked to a first portion of a luciferase gene, and a second construct containing cDNA encoding eIF4E linked to a second portion of a luciferase gene) are then exposed to rapamycin or rapalogs. A convenient approach to measure the cells response to rapamycin is to obtain a concentration dependent response. By way of example, rapamycin can be used from 5 nM to 50 nM to 500 nM. In certain embodiments, rapalogs include temsirolimus, everolimus, deforolimus, and the like. The sensitivity of the mTOR variant toward rapamycin or rapalogs can be conveniently measured by an increase in light emission as compared to a negative control (i.e., a vehicle without rapamycin or rapalog).

In certain embodiments, the cell is transfected with a cDNA encoding mTOR. The cDNA can be conveniently prepared using standard methodologies known to one skilled in the art. In certain embodiments, the cDNA can be mTOR wild-type. In certain embodiments the cDNA can be a mTOR variant. In further embodiments, the mTOR variants can contain one or more mutations different from the mTOR wild-type.

In certain embodiments, the present assay can also be used to test if a particular compound has an inhibitory effect toward mTOR protein. The cell system containing the mTOR variant, a construct containing a cDNA encoding 4E-BP1 or 4E-BP2 linked to a first portion of a luciferase gene, and a construct containing a cDNA encoding eIF4E linked to a second portion of a luciferase gene, are exposed to a mTOR inhibitor. The sensitivity of the mTOR variant to treatment with the mTOR inhibitor can be measured by an increase in light emission as compared to a negative control.

In certain embodiments, the cells express a knockout or knock down of endogenous 4E-BP1 and/or 4E-BP2. In certain embodiments, the knock down is a genomic modification of at least a portion of the EIF4EBP1 gene or the EIF4EBP2 gene that results in a loss of protein expression of 4E-BP1 or 4E-BP2, respectively. In certain embodiments, the genomic modification is performed using CRISPR/CAS9 technology. In certain embodiments, the genomic modification is performed using TALENs or recombination technology.

In certain embodiments, the cells express a knock down or knockout of endogenous mTOR. In certain embodiments, the knock down or knockout of mTOR is completed in cells that have a genomic modification of at least a portion of the EIF4EBP1 gene or the EIF4EBP2 gene. In certain embodiments, the knock down or knockout of mTOR is completed by genomic modification of MTOR using CRISPR/CAS9 technology. In certain embodiments, the genomic modification of MTOR is performed using TALENs or recombination technology. In certain embodiments, the knock down or knockout of mTOR protein may be accomplished through siRNA treatment.

In certain embodiments, the present assay may be used to determine whether variants in a patient MTOR gene would create a variant mTOR that will respond to a specific mTOR inhibitor. The method involves preparing a cDNA equivalent to a mTOR variant from a patient followed by transfecting the cDNA into a cell. The cell has undergone a genomic modification to the EIF4EBP1 gene or the EIF4EBP2 gene, resulting in 4E-BP1 or 4E-BP2 knock down or preferably knockout. The cell has been transfected with a first cDNA containing 4E-BP1 or 4E-BP2 as well as a second cDNA containing eIF4E. The first cDNA is linked at its N-terminus to a first portion of a luciferase gene and the second cDNA is linked at its N-terminus to a second portion of a luciferase gene. When mTOR is inactivated, the protein products of the two cDNAs interact and the protein products of the luciferase come into complex to produce a light signal.

In certain embodiments, the present assay may be used to screen new mTOR inhibitor compounds to determine efficacy in the treatment of cancer. mTOR inhibitors that are currently part of cancer treatment studies include rapamycin and rapalogs. Examples of mTOR inhibitors that bind in the ATP-binding pocket are AZD2014, INK128, CC223, PF5212384, LY3023414, and combinations thereof. Depending on the compound to be utilized in the assay, suitable vehicles include DMSO, DMF, water, aliphatic alcohols, and mixtures thereof. In certain embodiments, the present assay may be used to identify new chemical compounds to assess their abilities to inhibit mTOR.

In one aspect, the invention includes a kit for determining mTOR activity in patient cells or for determining a patient's response to mTOR inhibitors. In some embodiments, the invention includes a kit for determining the molecular cancer profile in a subject by identifying patient specific mTOR, 4E-BP1 or 4E-BP2 variant response to mTOR treatments. In another embodiment, the kit comprises at least one means of detecting luciferase activity. Preferably, kits of the invention contain reagents necessary for determining mTOR activity in patient cells. Preferably, kits contain forward and reverse primers designed for subcloning that can be used in a genomic PCR analysis. Kits of the invention may contain diagnostic reagents and printed instructions for use.

The assays of the invention are carried out under culture conditions effective for protein expression from cells. The assays are performed in a vessel capable of holding the cells and reagents and not interfering with assay results. In some embodiments the plates are surface treated to facilitate adherence of the assay cells to the wells of the plate, such treatment is commonly referred to as "tissue culture treated". The surface treatment is typically an oxygen plasma discharge that renders the surface of the wells more hydrophilic. In some embodiments the assays are miniaturized and use multi-well plates known in the art. In certain embodiments, the present assay can be conveniently performed in a 96 well plate, but can also be adopted for high-throughput 384 well plates or 1536 well plates. In some embodiments dispensing the cells and/or reagents for the assays into the wells of the plates is automated. In some embodiments the cells and/or reagents are dispensed continuously at a high speed. In one embodiment an acoustic liquid dispenser is used to dispense the reagents.

The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXPERIMENTAL STUDIES

Example 1 mTOR Activity Assay Involving the Interaction Between eIF4E and 4E-BP1

We developed an assay that measures mTOR activity by examining the interaction between eIF4E and 4E-BP1, such that when the two proteins form a complex, a light signal would be observed. In this assay we use split-luciferase complementation by linking eIF4E and 4E-BP1 to separate portions of a luciferase protein and then we measure the interaction between 4E-BP1 and eIF4E, which is used as a surrogate measure of mTOR activity and the ability of mTOR to respond to rapamycin. The NanoBiT assay system is obtained from Promega (Madison, Wis.) in our split-luciferase complementation design. To implement the assay, we created cDNA encoding eIF4E linked to the "Small BiT" (SB) portion of the luciferase gene and cDNA encoding 4E-BP1 linked to the "Large BiT" (LB) portion of the luciferase gene, and transfected cells with the indicated cDNAs.

Figure 1B:
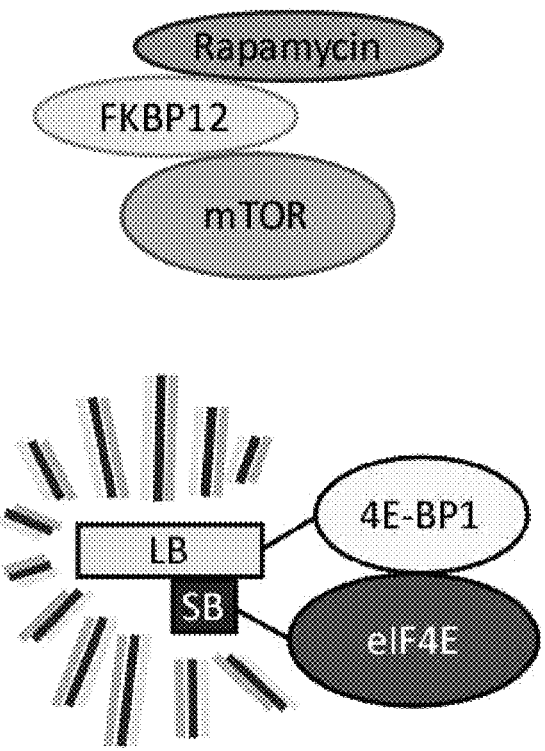

The design of our signal system to measure mTOR activity is depicted in FIG. 1. Under basal conditions inside the cell, mTOR is active and phosphorylates 4E-BP1 at 4 amino acid residues, preventing 4E-BP1 from interacting with eIF4E. In the presence of the mTOR inhibitor rapamycin, mTOR is bound to a rapamycin-FKBP12 complex, which allows 4E-BP1 to interact with eIF4E (FIG. 1). For this assay design, we created full length cDNAs of eIF4E linked to part of the luciferase protein, termed the "Small BiT" (SB) and 4E-BP1 or 4E-BP2 linked to the other portion of the luciferase protein, termed the "Large BiT" (LB) (FIG. 2). We performed PCR and ligated full-length cDNAs of eIF4E and 4E-BP1, obtained from Origene (Rockville, Md.), into NanoBiT designed vectors MCS-4 and the MCS-3, respectively (Promega). Oligonucleotide primers designed for subcloning are indicated in Table 1.

When eIF4E and 4E-BP1 or 4E-BP2 bind, the NanoBiT parts of the luciferase complement each other, and they emit a light signal when the luciferase (NanoGlo) substrate is added. FIG. 2 provides the base pair and amino acid sequences of the SB-linked eIF4E (A,D), LB-linked 4E-BP1 (B,E), and LB-linked 4E-BP2 (C,F).

We performed PCR and ligated full-length cDNAs of eIF4E and 4E-BP1, obtained from Origene (Rockville, Md.), into NanoBiT designed vectors pBiT2.1-N [TK/SmBiT] and the pBiT1.1-N [TK/LgBiT], respectively (Promega). Oligonucleotide primers designed for subcloning are indicated in Table 1.

Figure 3A:
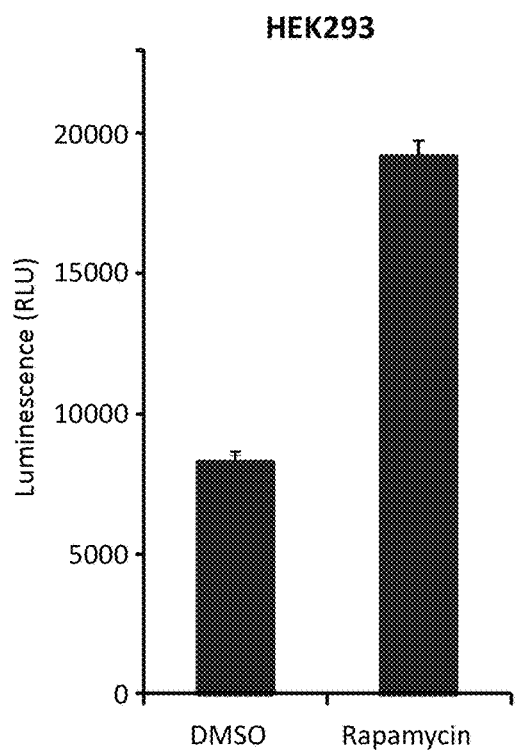
FIG. 3A depicts the luciferase activity in HEK293 cells transfected with SB-eIF4E and LB-4E-BP1 as a measurement of mTOR activity and rapamycin-mediated inhibition of mTOR.
Figure 3B:
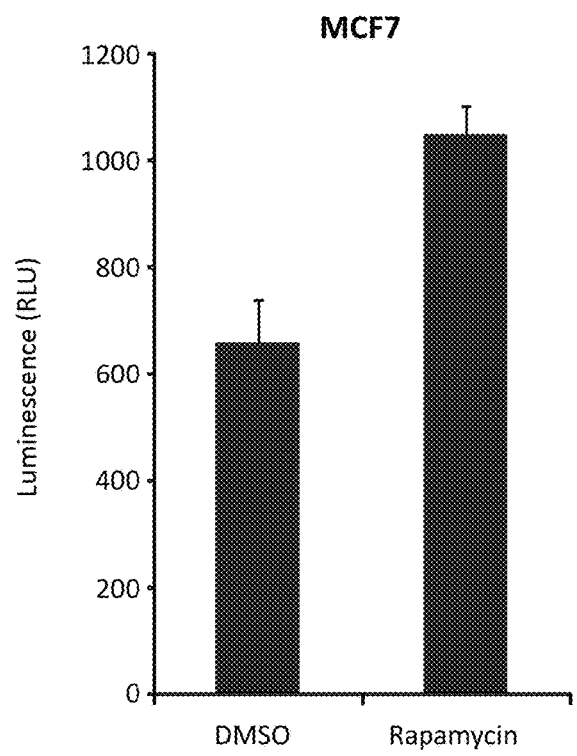
FIG. 3B depicts the luciferase activity in MCF-7 cells transfected with SB-eIF4E and LB-4E-BP1 as a measurement of mTOR activity and rapamycin-mediated inhibition of mTOR.

Example 2 Rapamycin Inhibition of mTOR Activity is Observed with SB-eIF4E/LB-4E-BP1 Assay Using the above mentioned assay design, we transiently transfected either HEK293 cells or MCF-7 cells with the SB-eIF4E and LB-4E-BP1 components and tested for specific mTOR activity using the inhibitor rapamycin (FIG. 3). With treatment of rapamycin, an increase in luminescence was observed, consistent with a decrease in mTOR activity resulting in an increased interaction between SB-eIF4E and LB-4E-BP1. This increase was observed in both HEK293 cells (FIG. 3A) and MCF-7 cells (FIG. 3B). Relative intensities are represented in FIG. 3 as relative luminescence units (RLU). Data represent a sample experiment where each condition was performed in triplicate and represent mean+SD.

Example 3 Different Constructs of eIF4E and 4E-BP1 cDNA

We designed different constructs of cDNAs encoding eIF4E and 4EBP1. Specifically, we created two truncated constructs of eIF4E and four truncated constructs of 4E-BP1 also changing the end of the LB attachment for some of the truncated 4E-BP1 constructs (Table 1). As controls, we also constructed the full-length eIF4E and full-length 4E-BP1 (Table 2). We also found that N-terminal full-length 4E-BP2 (a homologous protein to 4E-BP1) was similar in performance to 4E-BP1.

We made each of the constructs indicated in Table 1 and Table 2 and compared the "fold change" based on the fraction of luminescence activity observed with rapamycin treated cells versus that of the vehicle treated. To examine the ability of the split luciferase to properly assay mTOR activity, we transfected HEK293 cells with eIF4E and 4E-BP1 cDNA constructs, as indicated, and tested the dependence on mTOR activity with a 1 hour (h) treatment with rapamycin (50 nM). We interpreted an increase in signal with rapamycin to coincide with the ability to evaluate mTOR activity by the designed assay.

We tested the N-terminal amino acid requirements of eIF4E and found that shorter iterations of SB-eIF4E were effective, but they decreased the "fold-change" when compared to full-length eIF4E (Table 2). Only the modifications to the assay constructs are indicated in Table 2. The fold-change listed is the average of 2-4 independent experiments per condition±SD.

To investigate the amino acid requirements of 4E-BP1 in this assay, we tested the assay fold-change with the LB on either the N- or C-terminus, and then evaluated the signal in the presence of amino acid truncations from the side where the LB was attached. We found that the assay was not as effective with the LB on the C-terminus, and that the full-length 4E-BP1 performed better than those with amino acid truncations. We also tested the Large BiT on the N-terminus of 4E-BP2, a eIF4E binding protein highly homologous with 4E-BP1, and found that LB-4E-BP2 was similarly capable of interacting with SB-eIF4E with an increased signal upon treatment with rapamycin.

Structural biology data of co-crystallizing eIF4E and 4E-BP1 suggested relatively close proximity of the center of 4E-BP1 with residue 27 of eIF4E (Marcotrigiano et al., 1999, MolCell). However, our data show the optimized the assay with requiring full-length versions of each protein to effectively assay mTOR activity. However, we found that the previously identified N-terminal full-length eIF4E and N-terminal full-length 4E-BP1 provided the best response (Table 2). We also found that N-terminal full-length 4E-BP2 (a homologous protein to 4E-BP1) was similar in performance to 4E-BP1.

TABLE 1

Primers designed for subcloning eIF4E and 4E-BP1 cDNA constructs and truncations into NanoBiT vectors.

| Target/Purpose | Forward Primer | Reverse Primer |
| --- | --- | --- |
| Full-length SB-eIF4E into pBiT2.1-N [TK/SmBiT], XhoI/XbaI ligation | GAGGTGGAGG CTCGAGCGGT ATGGCGACTGTCGAACCGGAAACCA [SEQ. ID.NO: 7] | GCGTACGCGTA TCTAGA TTA AACAACAAACCTA TTTTTAGTGGTGG [SEQ. ID.NO: 8] |
| SB-eIF4E-residues 20 to end into [TK/SmBiT], XhoI/XbaI ligation | GAGGTGGAGG CTCGAGCGGT GAGAAAACGGAATCTAATC [SEQ. ID.NO: 9] | GCGTACGCGTA TCTAGA TTA AACAACAAACCTA TTTTTAGTGGTGG [SEQ. ID.NO: 10] |
| SB-eIF4E-residues 27 to end into pBiT2.1-N [TK/SmBiT], XhoI/XbaI ligation | GAGGTGGAGG CTCGAGCGGT GAGGTTGCTAACCCAGAACACTATA [SEQ. ID.NO: 11] | GCGTACGCGTA TCTAGA TTA AACAACAAACCTA TTTTTAGTGGTGG [SEQ. ID.NO: 12] |
| Full-length 4E-BP1 into pBiT1.1-N [TK/LgBiT], XhoI/XbaI ligation | GAGGTGGAGG CTCGAG CGGT ATGTCCGGGGGCAGCAGCTGCAGCCAG A [SEQ. ID.NO: 13] | CGCGTACGC TCTAGA_TTA AATGTCCATCTCAAACTGTGACTCT [SEQ. ID.NO: 14] |
| LB-4E-BP1-residues 29 to end into pBiT1.1-N [TK/LgBiT], XhoI/XbaI ligation | GAGGTGGAGG CTCGAGCGGT CTCCCGCCCGGGGACTACAGCACGA [SEQ. ID.NO: 15] | CGCGTACGC TCTAGA_TTA AATGTCCATCTCAAACTGTGACTCT [SEQ. ID.NO: 16] |
| Full-length 4E-BP1 with C-terminal LB into pBiT1.1-C [TK/LgBiT], NheI/XhoI ligation | GCGATC GCTAGC ATGTCCGGGGGCAGCAGCTGCA [SEQ. ID.NO: 17] | GCCACCACCG CTCGAG CC AATGTCCATCTCAAACTGTGACTC [SEQ. ID.NO: 18] |
| 4E-BP1 with C-terminal LB at residue 95 into pBiT1.1-C [TK/LgBiT], NheI/XhoI ligation | GCGATC GCTAGC ATGTCCGGGGGCAGCAGCTGCA [SEQ. ID.NO: 19] | GCCACCACCG CTCGAG CC CTGGCTGGCTTCCATGGG [SEQ. ID.NO: 20] |
| 4E-BP1 with C-terminal LB at residue 85 into pBiT1.1-C [TK/LgBiT], NheI/XhoI ligation | GCGATC GCTAGC ATGTCCGGGGGCAGCAGCTGCA [SEQ. ID.NO: 21] | GCCACCACCG CTCGAG CC GGAAGGGCTGGTGACCCCCGG [SEQ. ID.NO: 22] |
| 4E-BP1 with C-terminal LB at residue 75 into pBiT1.1-C [TK/LgBiT], NheI/XhoI ligation | GCGATC GCTAGC ATGTCCGGGGGCAGCAGCTGCA [SEQ. ID.NO: 23] | GCCACCACCG CTCGAG CC AATGTCCATCTCAAACTGTGACTC [SEQ. ID.NO: 24] |
| Full-length LB-4E-BP2 into pBiT1.1-N [TK/LgBiT], XhoI/XbaI ligation | TGGAGGCTCGAGCGGT ATGTCCTCGTCAGCCGGCAGCGGCC [SEQ. ID.NO: 25] | CCGCCCCGACTCTAGA TTAGATGTCCATCTCGAACTGAGCATC [SEQ. ID.NO: 26] |
| Colony PCR and sequencing primers, insertion into NanoBiT vectors | ATGATGACACAAACCCCGCCCAGCGT [SEQ. ID.NO: 27] | CTGCATTCTAGTTGTGGTTTGTCCAAA CTC [SEQ. ID.NO: 28] |

TABLE 2

Amino acid requirements of the SB-eIF4E/LB-4E-BP1 assay.

| Design of constructs | Change in mTOR activity (Fold-change) | Results - Ability of construct to measure mTOR activity |
|---|---|---|
| Full-length SB-eIF4E/Full-length LB-4E-BP1 | 1.98 ± 0.14 | Optimized ability to test mTOR activity |
| Alter SB-eIF4E - residues 20 to end | 1.67 ± 0.12 | Reduced fold-change, but effective |
| Alter SB-eIF4E - residues 27 to end | 1.60 ± 0.30 | Reduced fold-change, but effective |
| Alter LB-4E-BP1 - residues 29 to end | 0.89 ± 0.17 | Not effective |
| Alter 4E-BP1 with C-terminal LB | 1.18 ± 0.38 | Minimally effective |
| Alter 4E-BP1 with C-terminal LB at residue 95 | 0.98 ± 0.25 | Not effective |
| Alter 4E-BP1 with C-terminal LB at residue 85 | 0.89 ± 0.18 | Not effective |
| Alter 4E-BP1 with C-terminal LB at residue 75 | 0.83 ± 0.39 | Not effective - loss of signal/interaction |
| Full-length LB-4E-BP2 replacing LB-4E-BP1 | 1.84 ± 0.44 | As effective as 4E-BP1 in measuring mTOR activity |

The optimized cDNAs for the assay with the Small BiT (SB) to be N-terminally linked to full length eIF4E (A) and the Large BiT (LB) to be N-terminally linked to full length 4E-BP1 (B), or the Large BiT (LB) to be N-terminally linked to full length 4E-BP2 (C) are indicated in FIG. 2. The underlined portion is the SB or LB of the sequence and the italics is 15Gly/Ser flexible linker. The remainder of the cDNA sequence is the cDNA provided by Origene for the expression of the designed protein. All sequences were confirmed by Sanger Sequencing. Based on the cDNA sequences created, we created the SB-eIF4E (D), LB-4E-BP1 (E), and LB-4E-BP2 (F) with the indicated amino acid sequences, when the cDNAs are expressed in mammalian cells.

Example 4 Time Course of Rapamycin Treatment in SB-eIF4E/LB-4E-BP1 Assay

Figure 4:
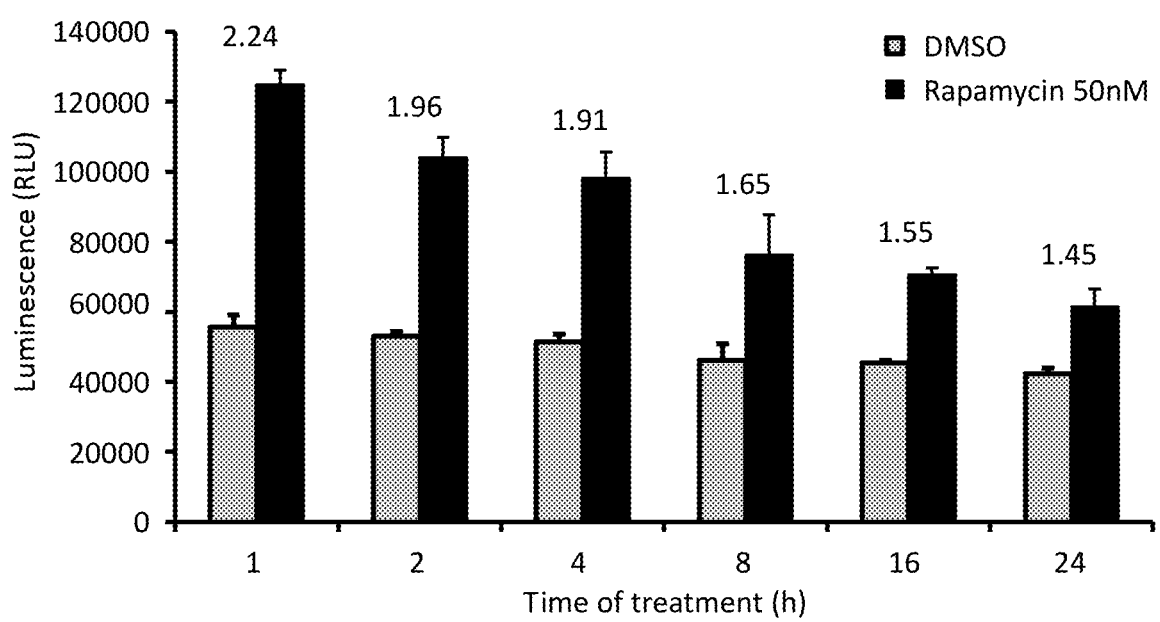
FIG. 4 depicts optimization of the assay by exposing SB-eIF4E/LB-4E-BP1 transfected HEK293 cells to rapamycin over time to observe the activation in response to mTOR inhibition.

We also optimized our assay by examining the time of treatment required to optimize the effect indicated by treating SB-eIF4E/LB-4E-BP1 transfected HEK293 cells with rapamycin from 1-24 hours (FIG. 4). The increase in fold-change, indicated by the numbers above the bars, was the highest at 1 h of treatment, and diminished through 24 h of treatment. Therefore, the SB-eIF4E/LB-4E-BP1 assay performed best with 1 h treatment.

Figure 5A:
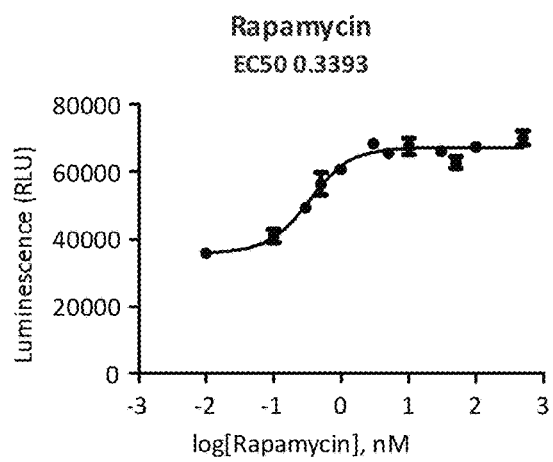
FIG. 5A and FIG. 5B depict the effectiveness of the assay, measured as a concentration-dependent activation of luminescence with rapamycin and everolimus, respectively. HEK293 cells were transiently transfected with SB-eIF4E/LB-4E-BP1 and treated for 1 hour with rapamycin (FIG. 5A) or everolimus (FIG. 5B).
Figure 5B:
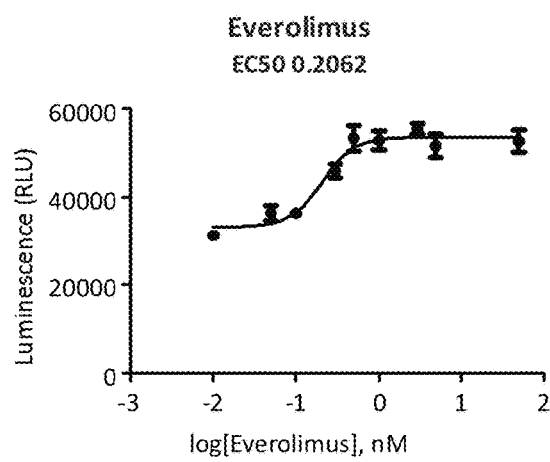

Example 5 Concentration—Dependent Increase in Signal with Rapamycin and Everolimus Based on the effectiveness of the assay created, we measured concentration curves for rapamycin and everolimus (an analog of rapamycin). HEK293 cells were transiently transfected with SB-eIF4E and LB-4E-BP1, as previously indicated, and then treated for 1 h with rapamycin (A) or everolimus (B) at a range of concentrations covering 5 logs. Based on the results, we obtained EC50s for rapamycin at ~0.34 nM and for everolimus at ~0.21 nM (determined using GraphPad Prism software) (FIG. 5).

The reported IC50 for rapamycin in inhibiting phosphorylation of S6 kinase is ~0.1 nM (Edwards & Wandless, 2007). The reported IC50 for everolimus in inhibiting phosphorylation of 4E-BP1 is 1.6-2.4 nM (Sedrani et al., 1998) with both of these studies using Western blot analyses for their measurements. Our designed system is at least as effective at measuring mTOR inhibition using these inhibitors, and performs a higher function of also measuring the downstream function of mTOR inhibition, which is missed with Western blot analyses.

Our assay was also more sensitive, showing more effective inhibition of mTOR than the FKBP12-FRB binding assay (Luker et al., 2004; Dixon et al., 2016), which produces an EC50 of ~4 nM for rapamycin. Further, our assay has the ability to measure the function of full-length mTOR and its genetic variants that may alter function.

Example 6 Site-Directed Mutagenesis of Phosphorylation Sites

Figure 6:
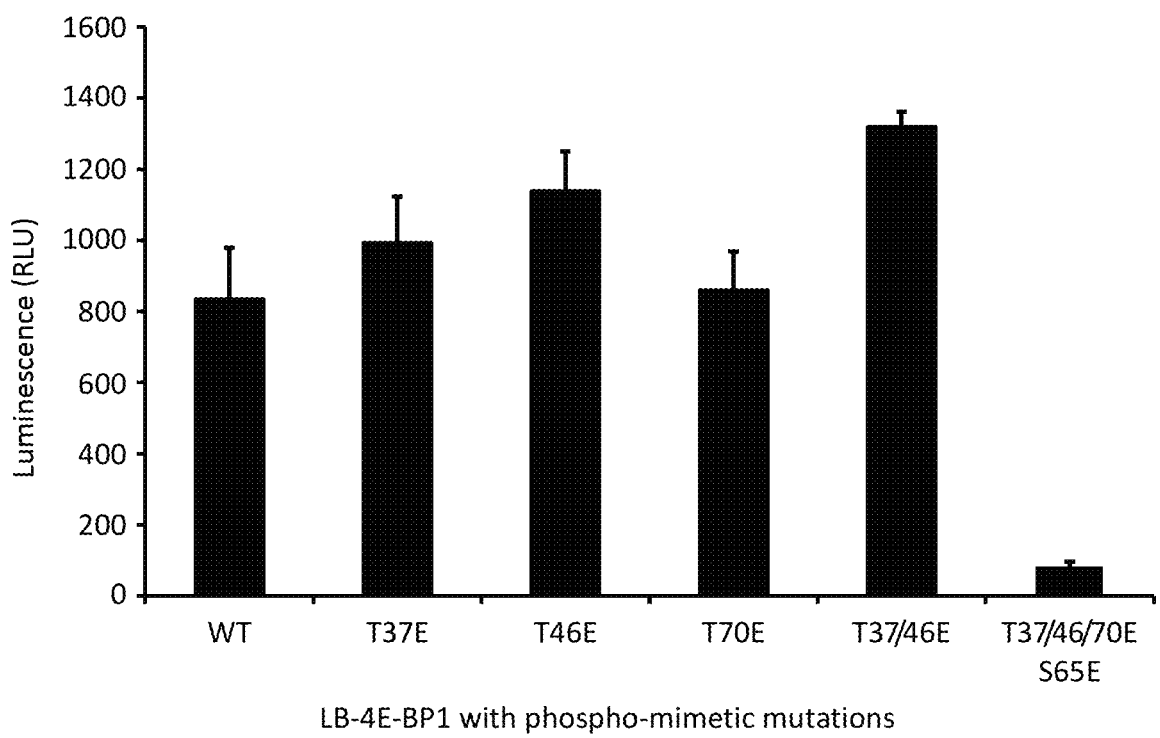
FIG. 6 depicts the phospho-mimetic mutations in 4E-BP1 that selectively alter the ability of 4E-BP1 to bind to eIF4E. Site-directed mutagenesis of phosphorylation sites from threonine residues (T) into glutamate (E) residues revealed mutations of T37E, T46E, and T70E had no effect on binding. Note that individual mutation of residues maintained binding; however mutations at all four phosphorylation sites abrogated protein binding. Analysis showed robust functional activity of the assay.

Within our developed assay, we further confirmed the specificity of phosphorylation statuses as it relates to the downstream binding and activity of the eIF4E/4E-BP1 interaction by mutating the phosphorylation sites on 4E-BP1 to glutamate (E) residues by altering the cDNA sequence on the LB-4E-BP1 construct. Since it is the binding of eIF4E with 4E-BP1 that is the end goal of inhibitors like rapamycin, rather than just identifying phosphorylation status, we mimicked phosphorylation of some of these residues by converting threonine residues (T) into glutamate (E), a bulky, negatively charged amino acid that can create structural changes similar to a phosphorylated residue. We performed site-directed mutagenesis on the LB-4E-BP1 plasmid using the primers indicated in Table 3. We examined T37E, T46E, T70E, T37/46E (double-mutant), and T37/46/70E/S65E (all 4 sites mutated) (FIG. 6).

We found that mutations of T37E, T46E, and T70E did not alter the binding of LB-4E-BP1 to SB-eIF4E. Mutation of all 4 phosphorylation sites to E was the only condition that prevented binding of the proteins, resulting in a loss of luminescence signal similar to that of cells without luciferase present. Importantly, most of the antibody-based assays to measure mTOR activity use the combination of T37/46 phosphorylation; however, mutating both T37/46 to E did not alter the interaction between eIF4E and 4E-BP1. Only a combination of all 4 residues mutated to glutamate removed the interaction, showing mTOR functional activity with the developed assay, rather than a measure of isolated phosphorylation sites. Therefore our designed assay provides the enhanced capability of assessing mTOR functionality and the effectiveness of inhibitors when compared to the measurement of phosphorylated residues.

TABLE 3

LB-4E-BP1 Site-Directed Mutagenesis Primers.

| Target/Purpose | Forward Primer | Reverse Primer |
| --- | --- | --- |
| LB-4E-BP1 with S65E mutation | ATG GAG TGT CGG AAC GAA CCT GTG ACC AAA ACA CC [SEQ. ID.NO: 29] | GGT GTT TTG GTC ACA GGT TCG TTC CGA CAC TCC AT [SEQ. ID.NO: 30] |
| LB-4E-BP1 with T70E mutation | TCGGAACtCACCTGTGACCAAAGAACCC CCAAGGGATCTGCCCACCATT [SEQ. ID.NO: 31] | AATGGTGGGCAGATCCCTTGGGGGTT CTTTGGTCACAGGTGAGTTCCGA [SEQ. ID.NO: 32] |
| LB-4E-BP1 with T37E and T46E mutations | GGGGACTACAGCACGGAGCCCGGCGGC ACGCTCTTCAGCACCGAGCCGGGAGGT ACCAGG [SEQ. ID.NO: 33] | CCTGGTACCTCCCGGCTCGGTGCTGA AGAGCGTGCCGCCGGGCTCCGTGCTG TAGTCCCC [SEQ. ID.NO: 34} |
| LB-4E-BP1 with T46E mutation | GGCGGCACGCTCTTCAGCACCGAG CCGGGAGGTACCAGGATCAT [SEQ. ID.NO: 35] | ATGATCCTGGTACCTCCCGGCTCGGT GCTGAAGAGCGTGCCGCC [SEQ. ID.NO: 36] |
| LB-4E-BP1 with T37E, T46E, S65E, and T70E-reaction performed on cDNA containing T37E and T46E | ATGGAGTGTCGGAACGAACCTGTGACC AAAGAACCCCCAAGGGATCTG [SEQ. ID.NO: 37] | CAGATCCCTTGGGGGTTCTTTGGTCAC AGGTTCGTTCCGACACTCCAT [SEQ. ID.NO: 38] |

Example 7 mTOR Variants Show Differential Response in Assay

Figure 7:
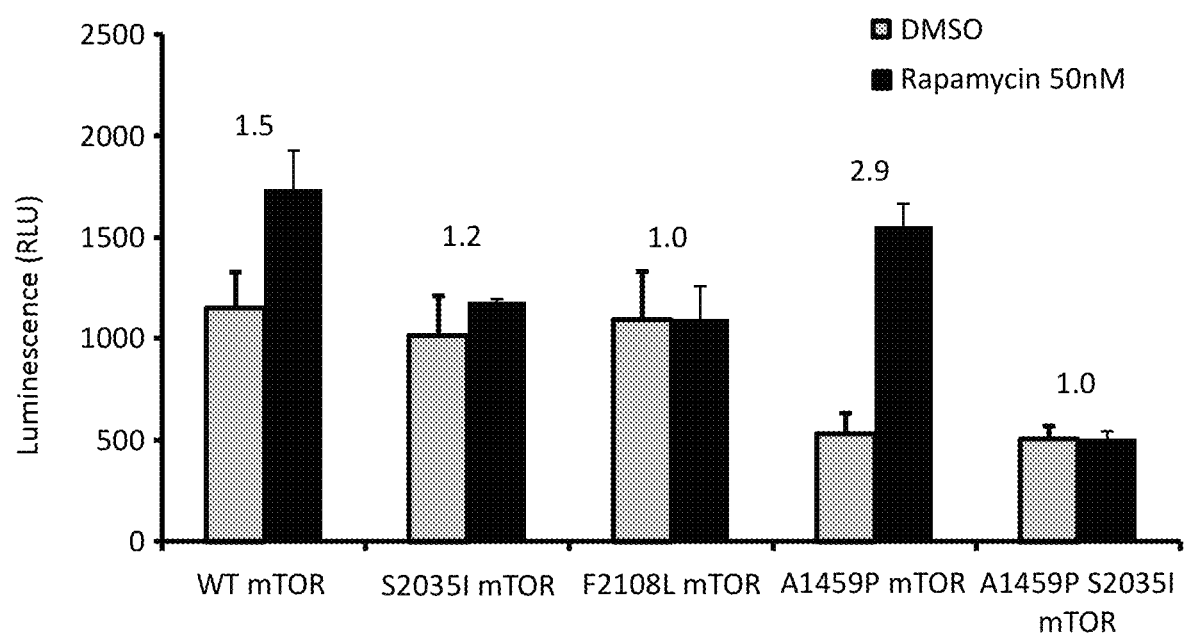
FIG. 7 depicts the effects of mTOR mutation using the SB-eIF4E/LB-4E-BP1 assay. Known mTOR mutations were created by site-directed mutagenesis and co-transfected with SB-eIF4E/LB-4E-BP1. Mutation specific resistance to rapamycin as well as relative activity of mTOR caused by mutations is detectable by the assay. Note that the mTOR variants used were the rapamycin-resistant S2035I and F2108L mutations and the hyperactive A1459P mutation.

We used site directed mutagenesis to create three mTOR variants. To examine the ability of our assay to detect variants in mTOR that affect function, we created the rapamycin-resistant mTOR mutations S2035I (Iiboshi, et al., 1999) and F2108L (Wagle et al., 2014). For comparison, we also created an mTOR mutation noted to be hyperactive but still responsive to rapamycin, A1459P (Grabiner et al., 2014). The mutations in mTOR were created by site-directed mutagenesis. The primers are indicated in Table 4. We co-transfected wild-type (WT) or mutated mTOR along with the SB-eIF4E and LB-4E-BP1, under otherwise the same conditions as previously indicated (FIG. 7). Over-expression of WT mTOR exhibited the previously observed increase in rapamycin-induced signal; however, the rapamycin-resistant mutations S2035I and F2108L did not. In addition, the hyperactive mutation A1459P presented with a lower basal signal in the absence of drug treatment, which would be indicative of greater phosphorylation of 4E-BP1, reducing the interaction with eIF4E. However, this mutation still responded to rapamycin (as expected; Grabiner et al., 2014), yielding a greater fold-change in response to rapamycin. Therefore SB-eIF4E/LB-4E-BP1 assay is capable of determining both mTOR mutant responsiveness to rapamycin and the relative activity level of mTOR mutations.

We further examined combination effects between the hyperactive mutation (A1459P) and a rapamycin-resistant mutation (S2035I) by creating a double-mutant mTOR. When mTOR contained both mutations, both the basal activity of mTOR was lower than WT mTOR, and there was no response to rapamycin, showing that this assay can also identify compounded effects of multiple mutations. The data is provided in Luminescence (RLU) of a single experiment with each condition performed in triplicate and represent average+SD. The numbers provided over each set of bars are a calculation of the "fold-change"—rapamycin treatment divided by the DMSO control.

TABLE 4

Primers For Site-Directed Mutagenesis to Create mTOR Variants

| Target/Purpose | Forward Primer | Reverse Primer |
| --- | --- | --- |
| mTOR S2035I site-directed mutagenesis | ATGA AGGCCTGGAAGAGGCA ATT CGTTTGTACTTTGGGGAAAG [SEQ. ID.NO: 39] | CTTTCCCCAAAGTACAAACG AAT TGCCTCTTCCAGGCCT TCAT [SEQ. ID.NO: 40] |
| mTOR A1459P | AAACTGCACGAGTGGGAGGATCCCCTT GTGGCCTATGACAAGAAAAT [SEQ. ID.NO: 41] | ATTTTCTTGTCATAGGCCACAAGGGG ATCCTCCCACTCGTGCAGTTT [SEQ. ID.NO: 42] |
| mTOR F2108L | TGGGACCTCTATTATCATGTGTTACGAC GAATCTCAAAGCAGCT [SEQ. ID.NO: 43] | AGCTGCTTTGAGATTCGTCGTAACACA TGATAATAGAGGTCCCA [SEQ. ID.NO: 44] |
| mTOR S2215Y | ACCCTTCTGGCCAATGACCCAACATATC TTCGGAAAAACCTCAGCATCCA [SEQ. ID.NO: 45] | TGGATGCTGAGGTTTTTCCGAAGATA TGTTGGGTCATTGGCCAGAAGGGT [SEQ. ID.NO: 46] |
| mTOR L2185A | GCAACGGACATGAGTTTGTTTTC GC TCTAAAAGGCCATGAAGATCTGCG [SEQ. ID.NO: 47] | CGCAGATCTTCATGGCCTTTTAGAGCG AAAACAAACTCATGTCCGTTGC [SEQ. ID.NO: 48] |

Example 8 Stable Expression of SB-eIF4E and LB-4E-BP1 in Cells

Figure 8:
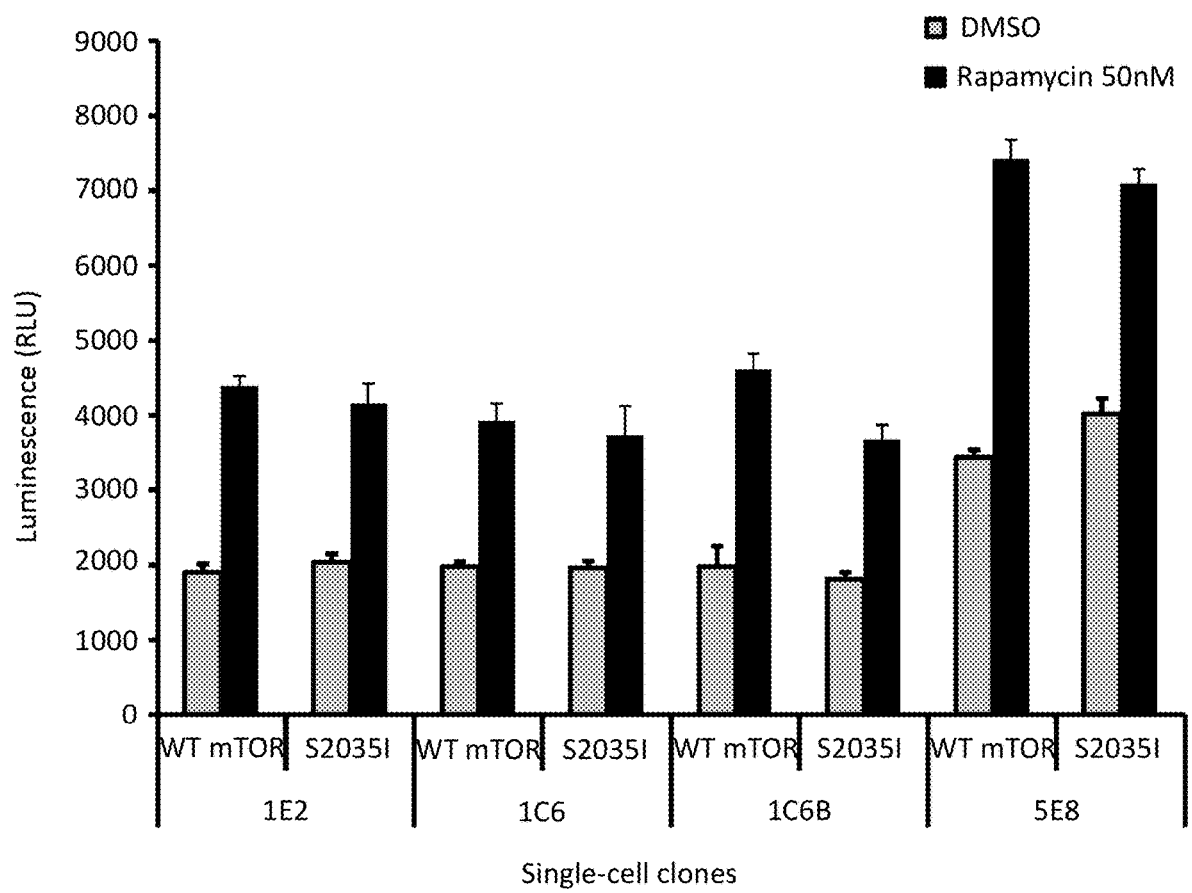
FIG. 8 depicts transient transfection of either mutant mTOR or WT mTOR into single-cell clones stably expressing both SB-eIF4E and LB-4E-BP1. Both the WT and the mutant mTOR responded to rapamycin treatment, contrary to expectations that the S2035I mutation in mTOR depicted would not respond to rapamycin treatment. Note, the ineffectiveness of the assay of mTOR mutations performed in single-cell clones show that stable expression of both SB-eIF4E and LB-4E-BP1 and transient transfection of mTOR did not provide sufficient assay performance.

Within the provided assay design, we then produced stable cell lines using the HEK293 cell parent line expressing SB-eIF4E and LB-4E-BP1. After selection and screening for positive clones using rapamycin-mediated increase in signal, we transfected WT or S2035I mTOR, the rapamycin-resistant mutant, into independent stable single cell clones to determine the ability to detect the rapamycin-resistant mTOR. All of the single-cell clones generated containing the SB-eIF4E/LB-4E-BP1 assay responded to rapamycin with an increase in signal, as previously observed with overexpression of WT mTOR (FIG. 8). However, the S2035I rapamycin-resistant mutation of mTOR responded similarly to WT mTOR, unlike the expected rapamycin-resistant response, as observed in FIG. 7. Based on our data, the effectiveness of assaying the activity of mTOR mutations is therefore dependent on transient transfection of LB-4E-BP1 and mTOR, at minimum, rather than stable expression of LB-4E-BP1 and transient expression of mTOR.

Example 9 Additional mTOR Inhibitors in Cells Expressing SB-eIF4E and LB-4E-BP2

The developed SB-eIF4E/LB-4E-BP1 assay was capable of assessing the activity of mTOR variants and effectiveness of rapamycin and rapalogs by measuring the interaction between eIF4E and 4E-BP1. However, we aimed to extend the assay's function to test additional mTOR inhibitors, since ATP-competitive mTOR inhibitors are currently being tested in clinical trials for treatment of cancer. For the purposes of testing our assay, we examined two additional mTOR inhibitors: AZD2014 produced by AstraZeneca, and INK128 (also known as MLN0128) produced by Millennium/Takeda Pharmaceuticals (both drugs purchased from Selleckchem). We tested HEK293 cells both transiently and stably expressing SB-eIF4E and LB-4E-BP1, at concentrations above and below the reported IC50s for each drug. While we found that there was a transient increase in the luciferase-based luminescence observed with a modest concentration of each new inhibitor, the luminescence decreased with higher concentrations, rather than producing the predicted concentration-dependent increase (Table 5). The data in Table 5 shows the results achieved with transiently transfected HEK293 cells and represent the average fold-change, defined as the relative light units (RLU) achieved with inhibitor divided by that achieved by the vehicle (DMSO) control, ±SD for 1-4 independent experiments.

We hypothesized that endogenous 4E-BP1 and/or 4E-BP2 protein may be conflicting with the SB-eIF4E/LB-4E-BP1 assay. We therefore designed CRISPR single guide RNA (sgRNA) oligonucleotides (oligo) to genomically remove portions of EIF4EBP1 and/or EIF4EBP2 from HEK293 cells. The oligonucleotides used for this design are indicated in Table 6. We designed 4 different sgRNA constructs to genomically modify each EIF4EBP1 and EIF4EBP2, and then we ligated the double stranded oligo into the into pCas-Guide-Nickase plasmid (Origene), where the Cas9 cDNA was constructed so that the amino acid sequence has a D10A mutation. By using a pair of sgRNA constructs with Cas9 D10A, we were capable of specifically targeting the EIF4EBP1 and EIF4EBP2 genes at the N-terminal ends after the initiating ATG for translation and prior to any of the mTOR phosphorylation sites, while minimizing nonspecific off-target effects (Cho et al., 2014). The goal was to create deletions in the genome resulting in a premature termination of the 4E-BP1 and 4E-BP2 translation into protein, thereby effectively "knocking out" 4E-BP1 and 4E-BP2 expression.

Figure 9A:
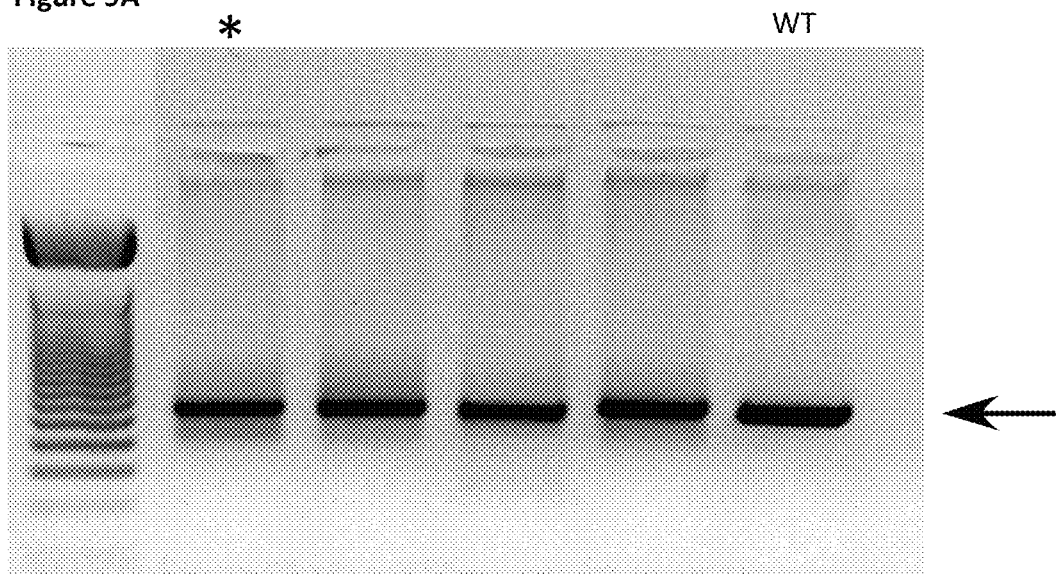
FIG. 9A and FIG. 9B depict the genomic polymerase chain reaction (PCR) of HEK293 cells transiently transfected with CRISPR sgRNA constructs directed against the EIF4EBP1 or EIF4EBP2 gene.
Figure 9B:
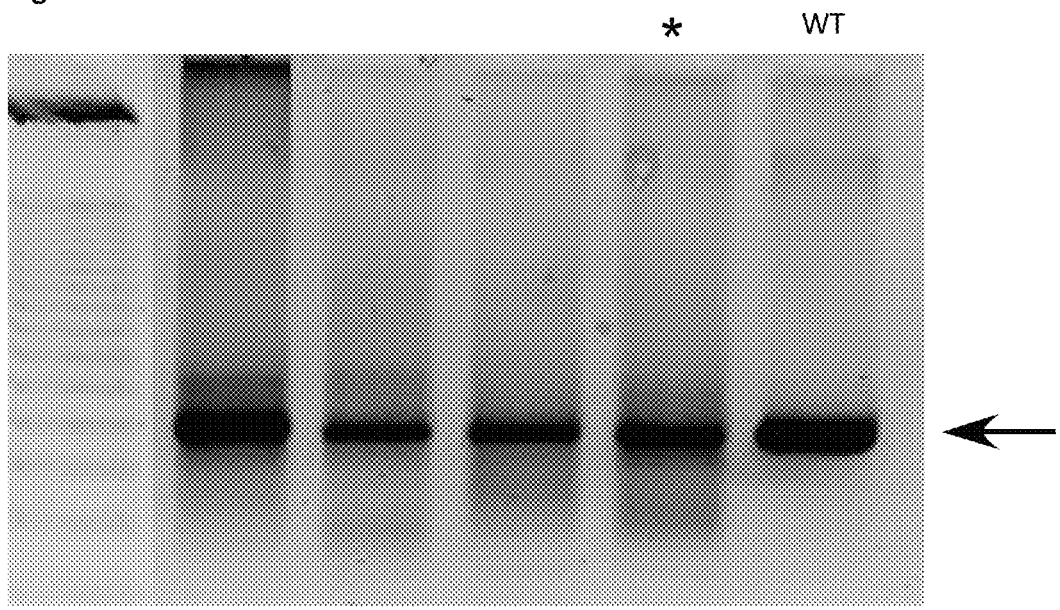
Figure 11A:
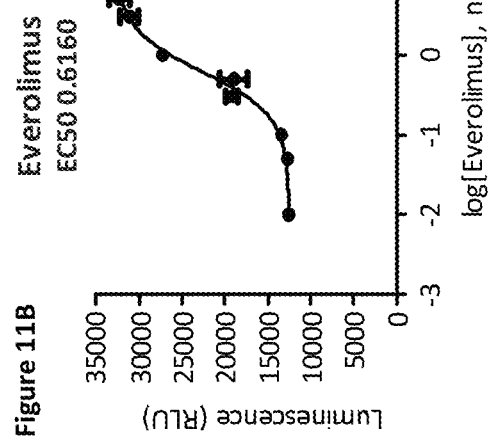
FIG. 11A, FIG. 11B, FIG. 11C, and FIG. 11D depict concentration-dependent activation of luminescence in the 3A1 dKO clone transiently transfected with SB-eIF4E/LB-4E-BP2 cDNAs and treated with rapamycin, everolimus, AZD2014, and INK128, respectively.
Figure 11B:
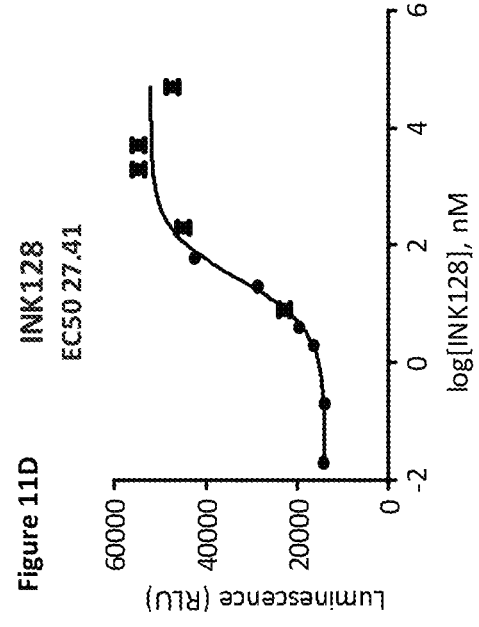
Figure 11C:
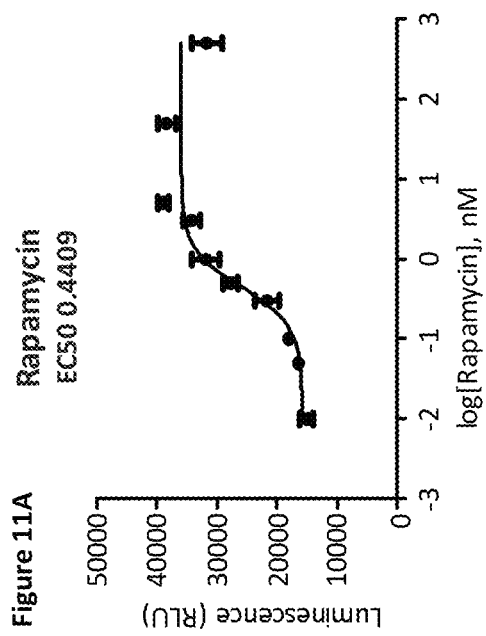
Figure 11D:
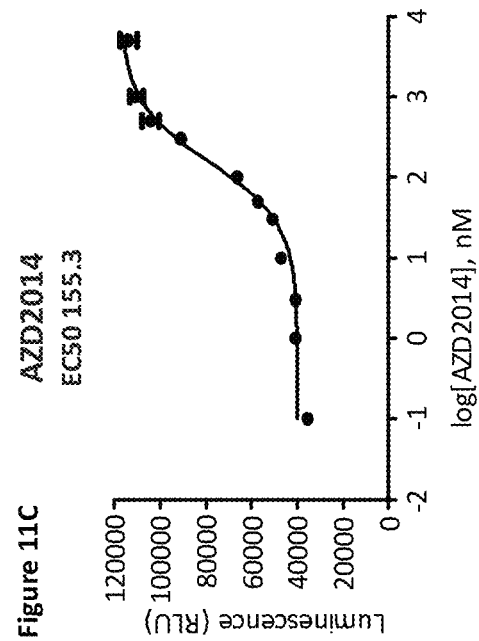
Figure 12A:
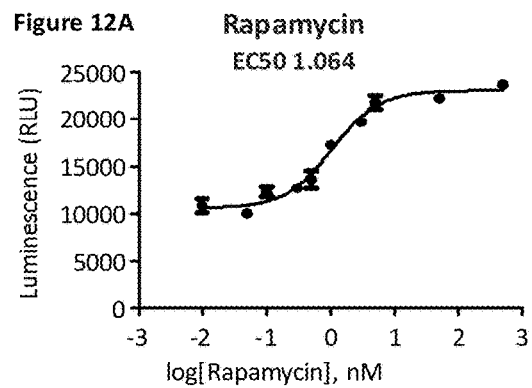
FIG. 12A, FIG. 12B, FIG. 12C, FIG. 12D, FIG. 12E, FIG. 12F, and FIG. 12G depict concentration-dependent activation of luminescence of the 3A1 clone with stable expression of SB-eIF4E/LB-4E-BP2 dependent on rapamycin, everolimus, AZD2014, INK128, CC223 (Celgene), PF05212384 (Pfizer), and LY3023414 (Eli Lily), respectively.
Figure 12B:
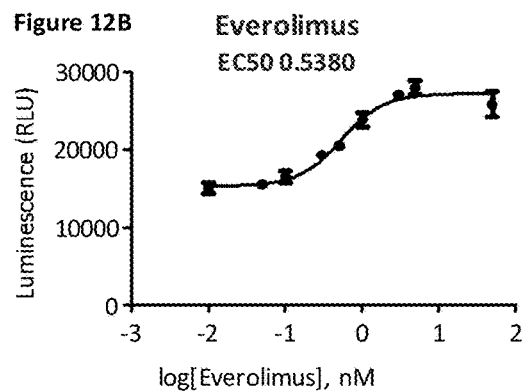
Figure 12C:
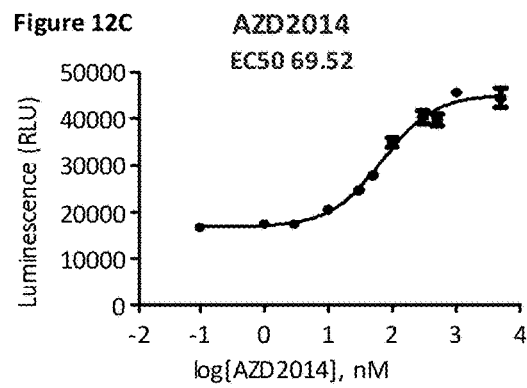
Figure 12D:
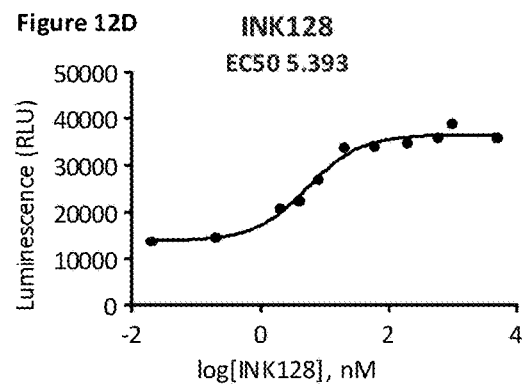
Figure 12E:
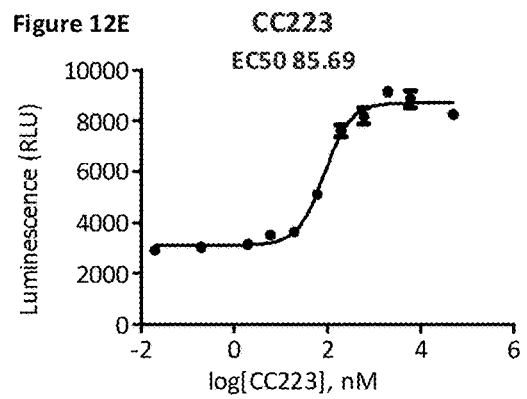
Figure 12F:
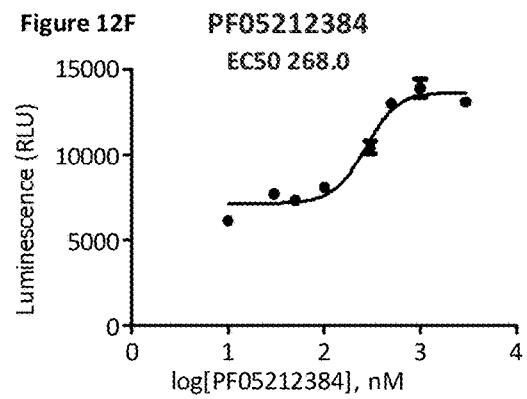
Figure 12G:
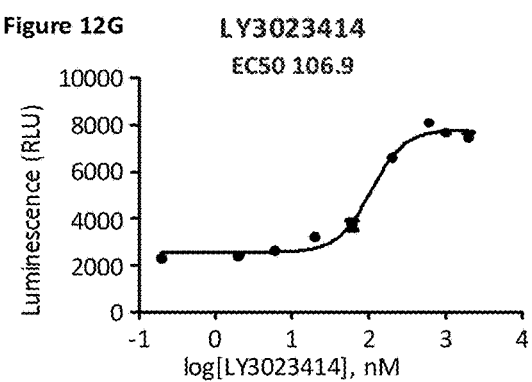
Figure 12H:
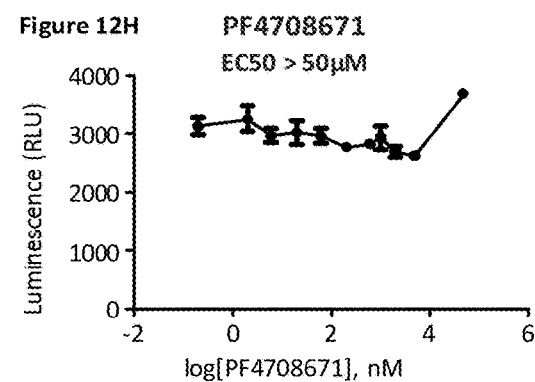
FIG. 12H depicts the 3A1 clone with stably expressed SB-eIF4E/LB-4E-BP2 when exposed to PF4708671 (Pfizer), and S6 kinase inhibitor, does not produce a concentration-dependent activation of luminescence.

The above designed constructs were then transfected into HEK293 cells in pairs such that one top strand pair was matched with a bottom strand pair to create a 5' overhang when the Cas9 cut the single strand of genomic DNA. Afterwards the efficiency of the CRISPR pairs was measured by genomic PCR (FIG. 9) using the primers indicated in Table 6. Each of the genomic PCR designs identified a ~250 bp fragment as the wild-type (WT)/unmodified gene. This is indicated as the arrow to the right. FIG. 9A shows the 4 tested combinations of CRISPR constructs for knockout of 4E-BP1 with untransfected HEK293 cells serving as a WT control on the right. The best performing combination, as indicated with the strongest secondary band, is indicated with an asterisk (*) above the lane. The corresponding selected pair of the best condition was composed of those indicated in Table 6 as "selected". Similarly, FIG. 9B shows the 4 combinations of CRISPR constructs for knockout of 4E-BP2 and the selection of the best performing pair with an asterisk (*). This pair is indicated also as "selected" in Table 6.

The highest efficiency pairs were subsequently transfected into HEK293 cells to produce the CRISPR-modified HEK293 cells. The transfections were performed by calcium phosphate precipitation. After transfecting the CRISPR set for 4E-BP2, the resulting pool of cells were re-plated for transfection with the CRISPR set for 4E-BP1. Single-cell clones were generated and 140 clones were screened by genomic PCR, such that products migrating at a size other than that of 250 bp were considered modified. Cells were screened using both 4E-BP1 and 4E-BP2 genomic PCR conditions. Single-cell clones were selected to contain one of the following conditions: modified 4E-BP1 with WT 4E-BP2, modified 4E-BP2 with WT 4E-BP1, and modifications of 4E-BP1 and 4E-BP2. Clones appearing to be heterozygous (only one chromosome modified and the other chromosome as WT) for either 4E-BP1 or 4E-BP2 were not selected. Seventeen of the clones fit the criteria of selection and were then screened by Western blot analyses for both 4E-BP1 and 4E-BP2. Only those clones containing knockout (KO) of 4E-BP1 and/or 4E-BP2, as determined by a lack of immunoreactivity by Western blot with antibodies directed towards a C-terminal epitope of 4E-BP1 or 4E-BP2 (Cell Signaling Technologies), were selected for additional testing. Assays were performed by transient transfection of SB-eIF4E/LB-4E-BP1 and then treated with mTOR inhibitors, as indicated in Table 5. After screening the originating 140 single-cell clones, we identified 3 independent 4E-BP1 KO cells, one 4E-BP2 KO cell, and 3 independent 4E-BP1/4E-BP2 double KO (dKO) cells.

We then tested the identified single-cell clones by transiently transfecting the cells with SB-eIF4E/LB-4E-BP1 and then treated with 2 concentrations of each inhibitor. The results were analyzed in terms of fold-change, and compared to WT (unmodified) HEK293 cells (Table 5). Each of the KO cell lines produced a better increase/fold-change with AZD2014 or INK128 than the parent WT HEK293 cells. The dKO cell lines performed consistently well, showing a concentration-dependent increase in the fold-change with higher concentration of drug treatment. Therefore, endogenously expressed 4E-BP proteins in HEK293 cells conflicted with adequately measuring the effects of mTOR inhibitors in the SB-eIF4E/LB-4E-BP1 assay.

TABLE 5

Endogenous 4E-BP effects on assay effectiveness with mTOR inhibitors

| Cell line/<br>CRISPR modification<br>knockout (KO) | Rapamycin (concentration) | | AZD2014 (concentration) | | INK128 (concentration) | |
|---|---|---|---|---|---|---|
| | 50 nM | 500 nM | 100 nM | 1000 nM | 20 nM | 200 nM |
| WT HEK293 cells | 1.92 ± 0.23 | 1.96 ± 0.27 | 1.45 ± 0.18 | 1.06 ± 0.19 | 1.34 ± 0.29 | 1.03 ± 0.17 |
| 4E-BP1 KO 1D6 | 1.97 | 2.09 | 1.79 | 2.39 | 2.01 ± 0.42 | 2.29 ± 0.18 |
| 4E-BP1 KO 2B1 | 2.40 ± 0.60 | 2.41 ± 0.52 | 2.04 ± 0.42 | 2.62 ± 0.82 | 2.36 ± 0.46 | 2.67 ± 0.58 |
| 4E-BP1 KO 2B11 | 1.95 | 1.98 | 1.75 | 2.07 | 1.81 ± 0.28 | 1.99 ± 0.21 |
| 4E-BP2 KO 1E3 | 1.96 ± 0.21 | 2.08 ± 0.43 | 1.71 ± 0.24 | 1.95 ± 0.43 | 1.96 ± 0.30 | 1.93 ± 0.26 |
| 4E-BP1/4E-BP2 dKO 1C3 | 2.03 ± 0.26 | 2.05 ± 0.14 | 1.89 ± 0.15 | 2.47 ± 0.21 | 2.09 ± 0.13 | 2.48 ± 0.30 |
| 4E-BP1/4E-BP2 dKO 3A1 | 1.89 ± 0.26 | 1.96 ± 0.21 | 1.96 ± 0.21 | 2.48 ± 0.16 | 2.27 ± 0.14 | 2.57 ± 0.30 |
| 4E-BP1/4E-BP2 dKO 3B3 | 2.07 ± 0.21 | 2.01 ± 0.08 | 1.87 ± 0.15 | 2.23 ± 0.13 | 2.08 ± 0.09 | 2.39 ± 0.21 |

TABLE 6

4E-BP CRISPR primers

| Target/Purpose | Forward Primer/Oligo | Reverse Primer/Oligo |
|---|---|---|
| 4E-BP1 CRISPR top strand-selected | GATCG GCCACTCGCCGGGTGGTGCT G [SEQ. ID.NO: 49] | AAAAC AGCACCACCCGGCGAGTGGC C [SEQ. ID.NO: 50] |
| 4E-BP1 CRISPR bottom strand-selected | GATCG CTGGCTGCAGCTGCTGCCCC G [SEQ. ID.NO: 51] | AAAAC GGGGCAGCAGCTGCAGCCAG C [SEQ. ID.NO: 52] |
| 4E-BP2 CRISPR top strand-selected | GATCG GGCCAGCCGTCCGCCGCGCC G [SEQ. ID.NO: 53] | AAAAC GGCGCGGCGGACGGCTGGCC C [SEQ. ID.NO: 54] |
| 4E-BP2 CRISPR bottom strand-selected | GATCG ATAGTCATGAGGTAGCTGCG G [SEQ. ID.NO: 55] | AAAAC CGCAGCTACCTCATGACTAT C [SEQ. ID.NO: 56] |
| 4E-BP1 genomic PCR | AGGGCAGCGAGAGGTTCGCGGG TGC [SEQ. ID.NO: 57] | TCCAATCCGCGATTCCCGATCCTCC [SEQ. ID.NO: 58] |
| 4E-BP2 genomic PCR | ACAAAGCCGAGAGCCCGCGCCC [SEQ. ID.NO: 59] | AAGCGGCCGGGCACCGAGGCGCCG A [SEQ. ID.NO: 60] |
| 4E-BP1 CRISPR top strand-poor efficiency | GATCG CGCCGGGTGGTGCTCGGCGA G [SEQ. ID.NO: 61] | AAAAC TCGCCGAGCACCACCCGGCG C [SEQ. ID.NO: 62] |
| 4E-BP1 CRISPR bottom strand-poor efficiency | GATCG GGCGAGTGGCGGGGATGGCC G [SEQ. ID.NO: 63] | AAAAC GGCCATCCCCGCCACTCGCC C [SEQ. ID.NO: 64] |
| 4E-BP2 CRISPR top strand-poor efficiency | GATCG CCACACCGGGAGGTGAGCGC G [SEQ. ID.NO: 65] | AAAAC GCGCTCACCTCCCGGTGTGG C [SEQ. ID.NO: 66] |
| 4E-BP2 CRISPR bottom strand-poor efficiency | GATCG CGCGGCGTCGCTGATGGCCA G [SEQ. ID.NO: 67] | AAAAC TGGCCATCAGCGACGCCGCG [SEQ. ID.NO: 68] |

Example 10 Single-Cell Clones Containing Transient Transfection of SB-EIF4E, LB-4E-BP1, and LB-4E-PB2

Of the screened and identified single-cell clones, we selected the clones termed "3A1" and "1C3" for testing our assay with SB-eIF4E and LB-4E-BP1 or LB-4E-BP2 by transient transfection. We compared single-cell clone termed "3A1" (FIG. 10A,B) with single-cell clone termed "1C3" (FIG. 10C,D) in the assay containing either LB-4E-BP1 (FIG. 10A,C) or LB-4E-BP2 (FIG. 10B,D). Previously, in WT HEK293 cells, we did not find any difference between the assay designs of SB-eIF4E with LB-4E-BP1 versus LB-4E-BP2. Using either 4E-BP dKO clone and treating the cells with rapamycin, AZD2014, or INK128, we found a larger fold-change (indicated in the numbers on top of the bars) when the assay contained LB-4E-BP2. Both of the clones showed a similar trend with the only major difference noted as the luminescence (RLU) scale.

Example 11 Concentration Dependent Effect in the 3A1 Clone

FIG. 11 shows concentration dependent activation of the 3A1 clone transiently transfected with the SB-eIF4E/LB-4E-BP2 constructs and treated with the inhibitors rapamycin, everolimus, AZD2014, and INK128. The EC50s are listed under each drug name. The EC50s identified for rapamycin and everolimus were similar to those identified in the SB-eIF4E/LB-4E-BP1 assay transiently transfected in unmodified HEK293 cells. The reported IC50s for AZD2014 and INK128 are 2.8 nM (Guichard et al., 2015) and 1 nM (Hsieh et al., 2012), respectively. However, these are the IC50s in vitro, as produced in cell-free assays. The IC50 for inhibition of phosphorylation of the ribosomal protein S6 with AZD2014 is 210 nM (Guichard et al., 2015), and EC50 for the inhibition of cellular proliferation by INK128 is indicated as 17 nM (Hsieh et al., 2012). These cellular measures of mTOR inhibition are similar to those achieved with our designed assay. The benefits of our assay are ease of operation, clearly defined measurements, and specificity of the activity attributable to mTOR.

Example 12 Cell Clone Containing Stably Expressed SB-eIF4E and LB-4E-BP2

Taking the 3A1 clone, we created a stable cell line pool (cells that underwent a minimum of 2 weeks of hygromycin selection) with stable expression of SB-eIF4E/LB-4E-BP2. Using these cells, we examined the concentration-dependence of our assay treated with additional mTOR inhibitors currently under investigation in clinical trials and determined EC50 values (FIG. 12). Those tested included rapamycin, everolimus, AZD2014, INK128, CC223 (Celgene), PF05212384 (Pfizer), LY3023414 (Eli Lilly), and PF4708671 (Pfizer). Of note, the EC50 values for AZD2014 and INK128 shifted downward, suggesting greater sensitivity of the stable cell line pool in detecting the change in SB-eIF4E/LB-4E-BP2 interaction. Of the other tested chemicals, CC223, PF05212384, and LY3023414 each produced a concentration-dependent increase in luminescence, and PF4708671 did not. CC223 is an mTOR-specific inhibitor and PF05212384 and LY3023414 are dual mTOR/PI3K inhibitors. PF4708671 is an S6 kinase inhibitor, so the lack of response in our assay is expected and supports selectivity of our assay.

Example 13 Creation of Single-Cell Clones Expressing SB-eIF4E and LB-4E-BP2

Figure 13:
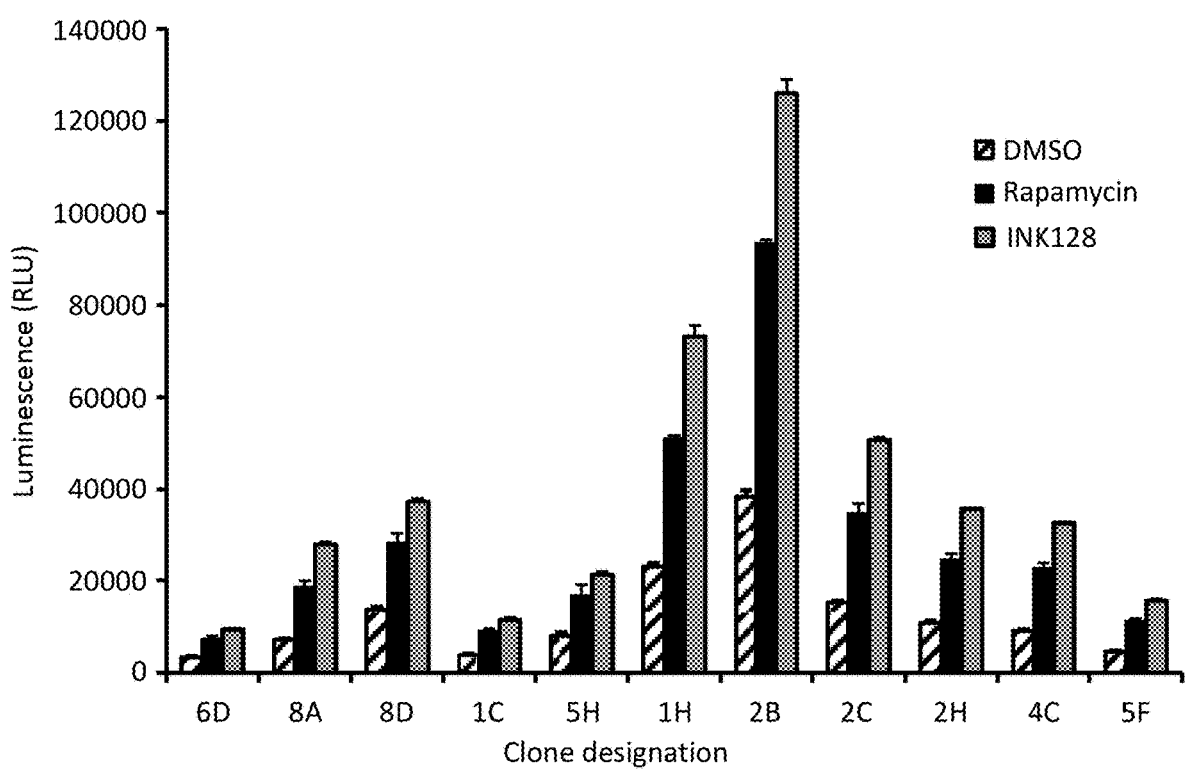
FIG. 13 depicts an increase in luminescence signal with rapamycin or INK128 for 11 generated single-cell clones, each clone having 4E-BP1 and 4E-BP2 deletion and with stable expression of SB-eIF4E and LB-4E-BP2, generated from the parent 3A1 clone.

We also produced single-cell clones using the stable cell line pool with stable expression of SB-eIF4E/LB-4E-BP2, indicated above (FIG. 13), using both rapamycin and INK128 to identify the best increase in response to drug treatment. All single-cell clones produced a similar increased response to rapamycin or INK128. We were therefore capable of producing single-cell clones containing the SB-eIF4E/LB-4E-BP2 assay components to measure the mTOR inhibition response with our assay.

Example 14 Test of mTOR Variants in 4E-BP dKO Cell Clones

Figure 14A:
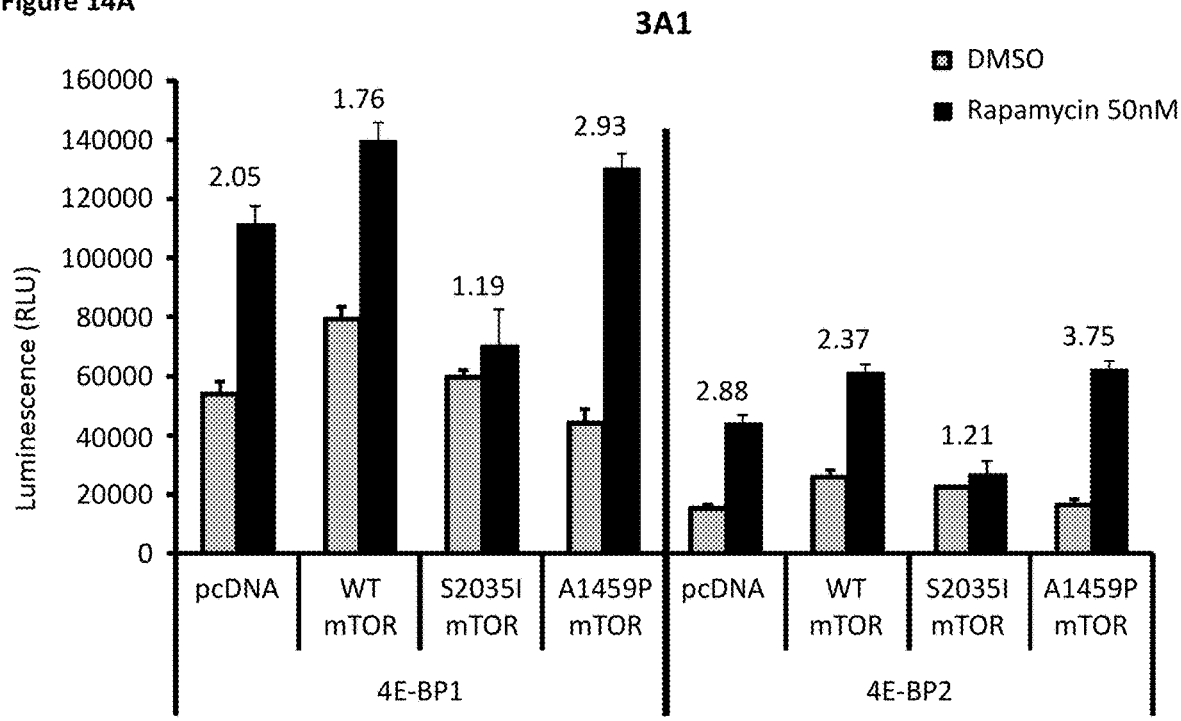
FIG. 14A depicts the effects of mTOR mutations in the assay using 3A1 single-cell clone, transiently expressing mTOR, SB-eIF4E, and LB-4E-BP1 or LB-4E-BP2.
Figure 14B:
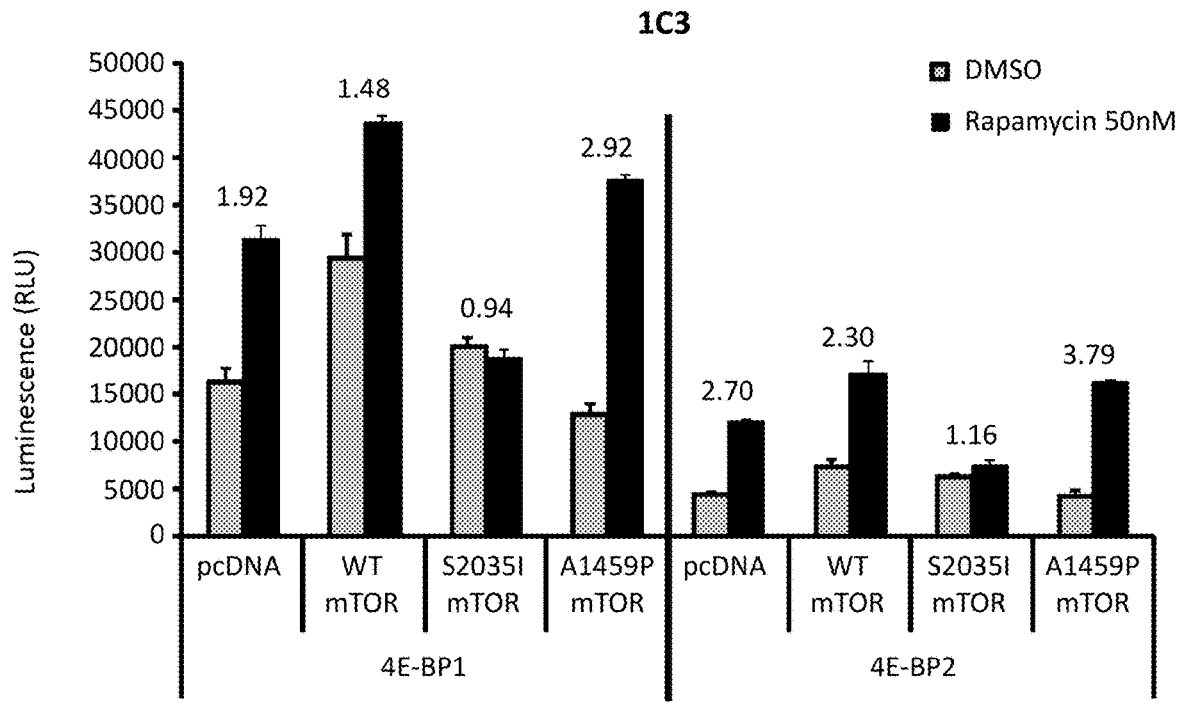
FIG. 14B depicts the effects of mTOR mutation in the assay using the 1C3 single-cell clone, transiently expressing mTOR, SB-eIF4E, and LB-4E-BP1 or LB-4E-BP2. Note that the mTOR variants used were the rapamycin-resistant S2035I mutation and the hyperactive A1459P mutation.

In addition to testing mTOR inhibitors in the currently designed assay, we aimed to test a combination of mTOR inhibitors against mTOR clinical variants to identify if we could detect with our assay mTOR variants that would predict clinical failure. FIG. 14 shows a comparison between 3A1 and 1C3 clones with transient transfection of WT or variant (mutant) mTORs in conjunction with SB-eIF4E and LB-4E-BP1 or LB-4E-BP2. We compared WT mTOR to the rapamycin-resistant S2035I mTOR and the hyperactive A1459P mTOR. We also tested pcDNA as an empty vector control, which would measure the effects of the endogenous mTOR. Both of the 4E-BP dKO clones performed similarly under the conditions tested with LB-4E-BP2 showing a higher fold-change (the numbers indicated above the bars) than LB-4E-BP1 with pcDNA, WT mTOR, and A1459P mTOR. The A1459P mTOR showed the expected decrease in basal activity (with DMSO), resulting in a higher fold-change after rapamycin treatment. The S2035I mTOR did not exhibit much of a response to rapamycin, as expected. The SB-eIF4E/LB-4E-BP2 assay in the 3A1 cell line also provided a better differential response between WT and mutant mTOR than the SB-eIF4E/LB-4E-BP1 assay in unmodified HEK293 cells (FIG. 7).

Example 15 mTOR Variant Response in Cells with Stable Expression of SB-eIF4E and LB-4E-BP2

After achieving a promising response in the 3A1 clone with transient transfection of SB-eIF4E and LB-4E-BP2, we examined the ability of mTOR variants to similarly alter the assay activity with rapamycin treatment in a 3A1 clonal pool stably expressing SB-eIF4E and LB-4E-BP2 (same line as that produced for Example 12). However, over-expression of variant mTORs did not produce the same profound differential response as that observed when SB-eIF4E and LB-4E-BP2 was transiently transfected into the 3A1 clone (FIG. 15—left side compared to FIG. 14A—right side). This result is analogous to the effect we observed when performing the assay on the stable clones with the SB-eIF4E/LB-4E-BP1 assay prior to performing 4E-BP1/4E-BP2 knockout (FIG. 8).

Figure 15:
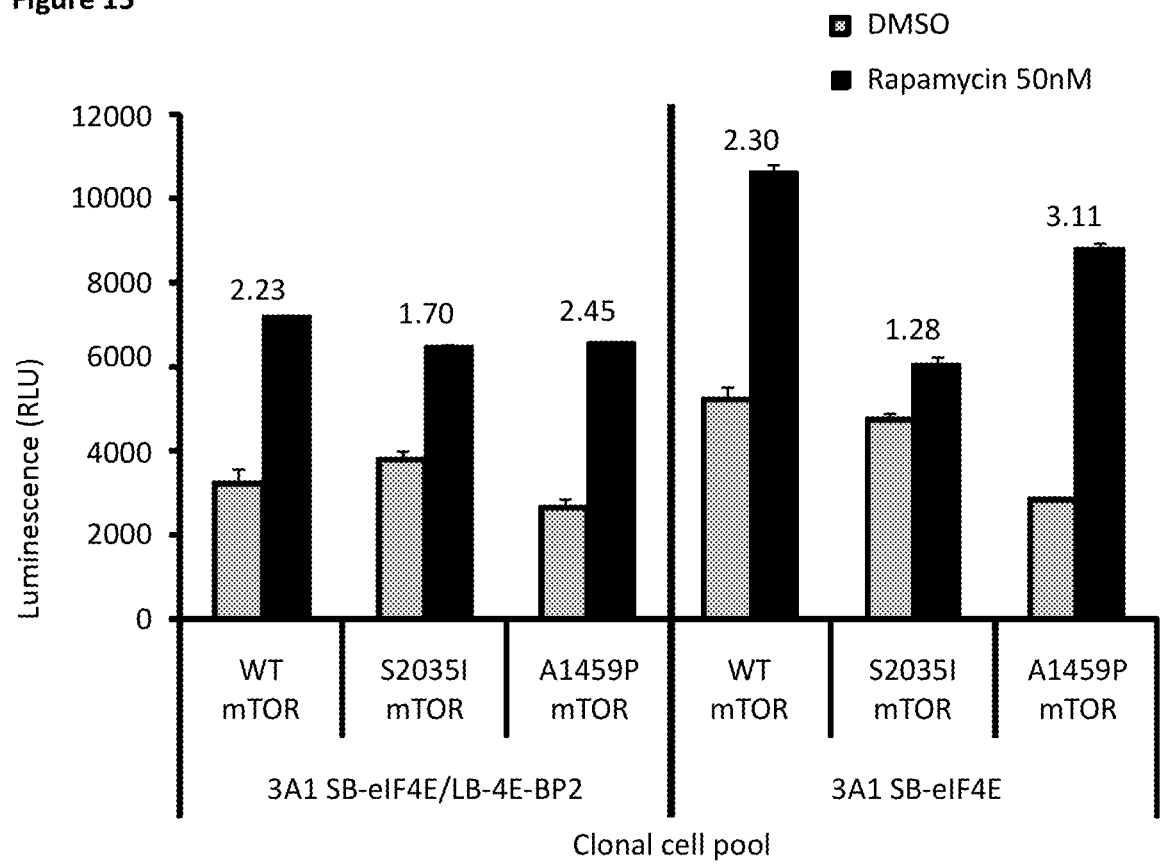
FIG. 15 depicts the responses of the mTOR mutations using clonal pools with 4E-BP1 and 4E-BP2 deletion and stably expressing SB-eIF4E and LB-4E-BP2 (left), compared to clonal pools with 4E-BP1 and 4E-BP2 deletion and stably expressing SB-eIF4E and transiently expressing LB-4E-BP2 (right). The mTOR variants used were the rapamycin-resistant S2035I mutation and the hyperactive A1459P mutation, which showed a mutation-specific response only in the clonal pools with 4E-BP1 and 4E-BP2 deletion, stably expressing SB-eIF4E, and transiently expressing LB-4E-BP2.
Figure 16A:
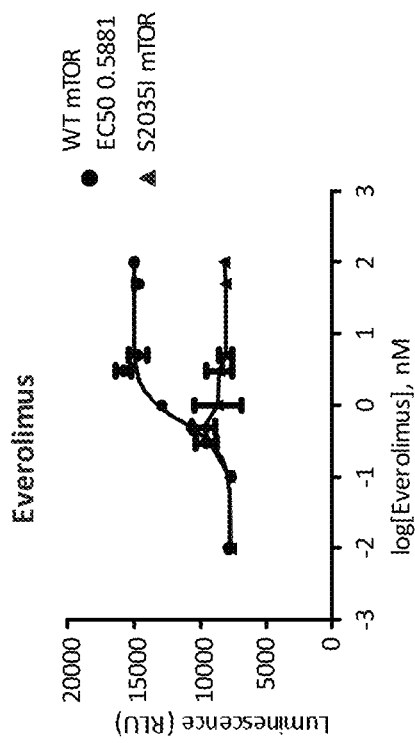
FIG. 16A, FIG. 16B, FIG. 16C, and FIG. 16D depict concentration-dependent effects of rapamycin, everolimus, INK128, and AZD2014, respectively, on using a single-cell clone with 4E-BP1 and 4E-BP2 deletion and stably expressing SB-eIF4E and transiently expressing 4E-BP2 and WT or S2035I (the rapamycin-resistant mTOR mutation) mTOR.
Figure 16B:
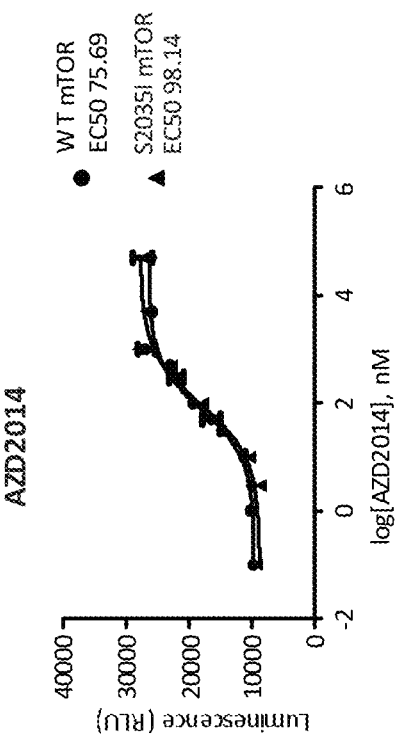
Figure 16C:
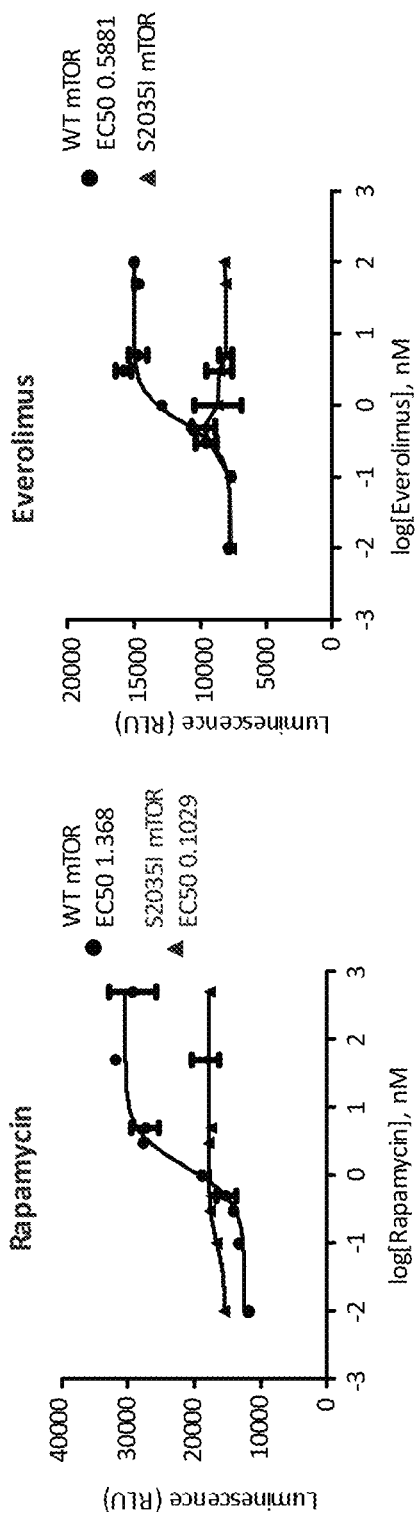
Figure 16D:
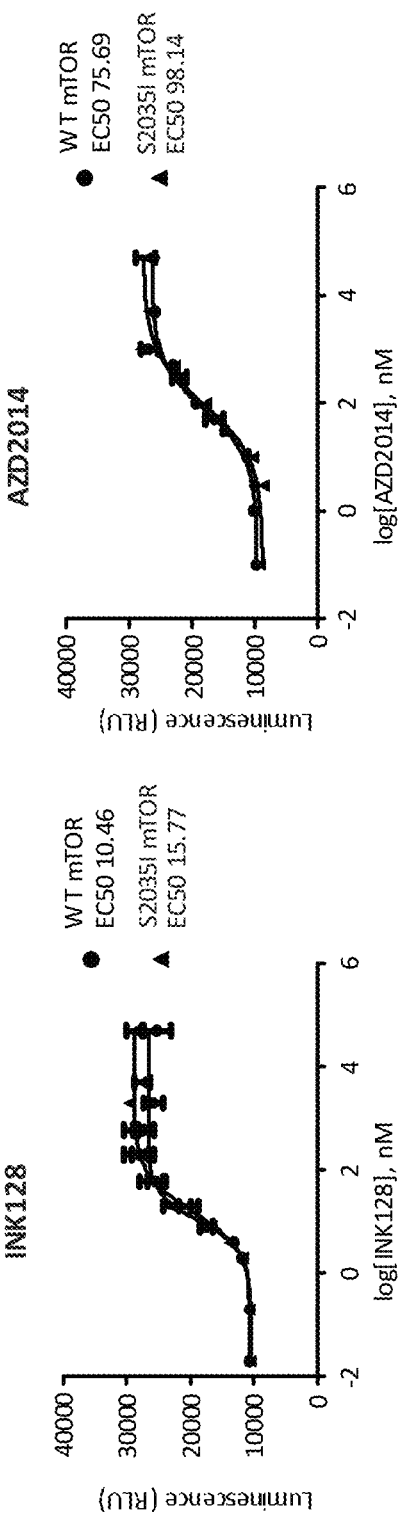

To overcome this issue, we created a stable cell pool with the 3A1 clone, stably expressing only SB-eIF4E. Therefore instead of transiently expressing either all three components or only just the variant mTOR, we transiently expressed only LB-4E-BP2 and the variant mTOR and found a better differential response between the WT and mutant mTORs (FIG. 15—right side). Therefore using the 3A1 clone stably expressing SB-eIF4E as our base cell-line, we were capable of measuring the effects of mTOR mutations and drug treatments.

Example 16 Concentration Curve for mTOR Inhibitor Response to mTOR Variant

In the 3A1 clone stably expressing SB-eIF4E, we completed concentration curves covering at least 5 logs for rapamycin, everolimus, INK128, and AZD2014 in cells transiently expressing LB-4E-BP2 and either WT or S2035I (rapamycin resistant) mTOR (FIG. 16). While all drugs showed a concentration-dependent increase in signal with WT mTOR, only INK128 and AZD2014 showed a concentration-dependent increase with S2035I mTOR. Therefore our assay was capable of identifying the rapamycin resistance as specific to rapamycin and everolimus, but not to INK128 and AZD2014.

Example 17 CRISPR Modification of MTOR Gene

In FIG. 16, although the S2035I mutation in mTOR exhibited a distinct response when compared to WT mTOR with rapamycin and everolimus treatment, a small increase in signal was observed that we attributed to the endogenously expressed mTOR. We therefore used CRISPR technology to genomically modify the MTOR gene and remove mTOR expression. Using primers indicated in Table 7, we aimed to remove Exon 3 of the MTOR gene, which would result in a frame shift and terminate mTOR expression in Exon 4. The best performing sgRNAs designed are indicated in the first 4 lines of Table 7. These were the sgRNAs used for genomic modification.

Figure 17:
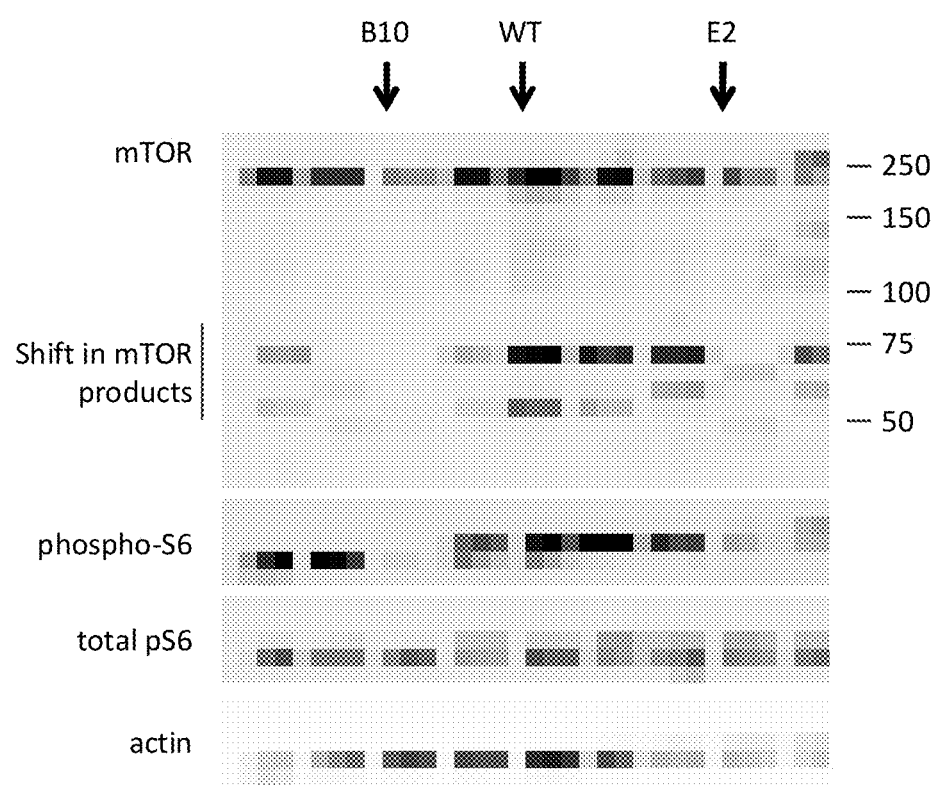
FIG. 17 depicts Western blot analysis of mTOR, phosphorylation of, total S6, and actin on single-cell clones with 4E-BP1 and 4E-BP2 deletion and CRISPR-mediated genomic modifications to the MTOR gene. Specific clones are indicated (B10 and E2) that show reduced mTOR expression and mTOR activity, as exhibited by reduced phosphorylation of S5, when compared to WT.
Figure 18A:
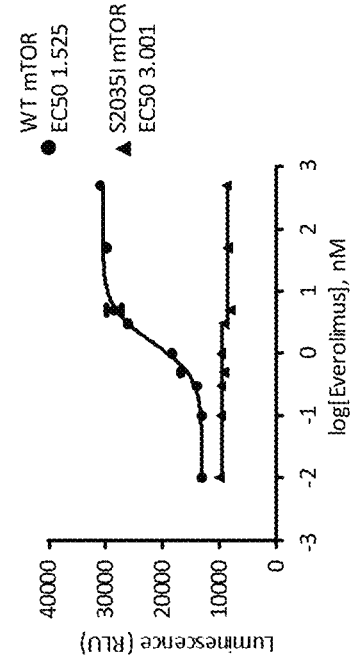
FIG. 18A, FIG. 18B, FIG. 18C, and FIG. 18D depict concentration-dependent effects of rapamycin, everolimus, INK128, and AZD2014, respectively, of mTOR mutation effects generated from the single-cell clone (B10) with 4E-BP1 and 4E-BP2 deletion and MTOR genomic modification, and then stably expressing SB-eIF4E and transiently expressing 4E-BP2 and WT or S2035I mTOR.
Figure 18B:
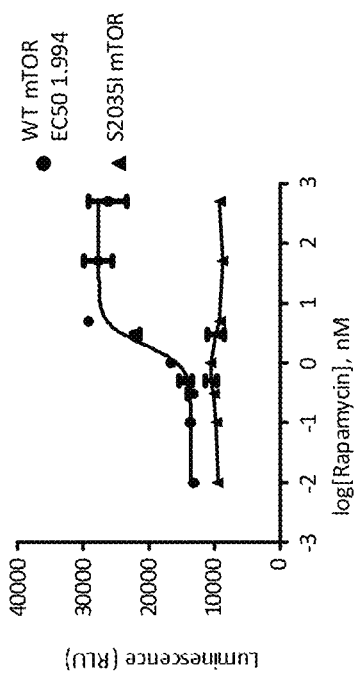
Figure 18C:
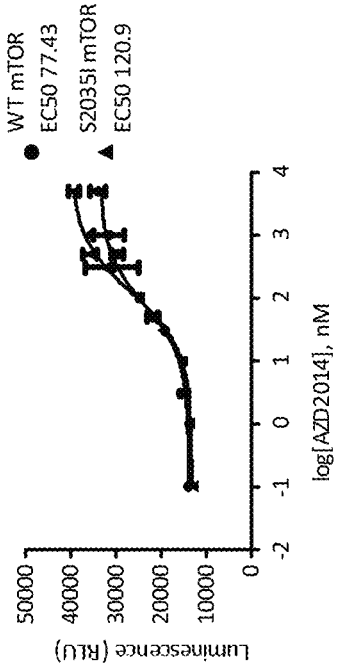
Figure 18D:
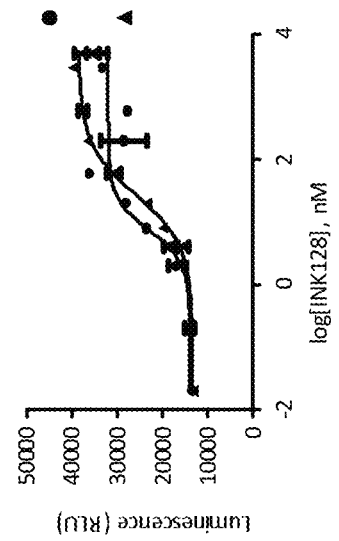

The 3A1 cell clone with the knockout of 4E-BP1 and 4E-BP2 was used as the parent cell line. These cells were transfected and then plated for clonal selection. After genomic PCR confirmation of the deletion of Exon 3, clones were screened by Western blot analyses. These data are provided in FIG. 17. Of the clones identified, only 2 exhibited a significant reduction in mTOR expression and a reduced amount of mTOR activity, measured by the amount of phosphorylation of S6 compared to the 3A1 (WT) clone. Of note, over 100 single-cell clones were screened to identify these 2 positive clones. Furthermore, prior to generating the 3A1 cell clone, previous attempts were made to CRISPR modify the MTOR gene in HEK293 cells that had previously been modified. Three prior attempts were made, with over 100 single-cell clones screened each time, and in none of those cases was a homozygous modification or a reduction in mTOR activity observed. Therefore, the modification of the MTOR gene, such that mTOR expression was prevented, was not going to be possible in this system. Furthermore, this work outlines the difficulty in being able to produce a cell line with reduced mTOR expression and activity through CRISPR modification.

Despite the confirmed genomic modification in the MTOR gene, mTOR expression was still observed. This likely resulted from an alternative initiating ATG in the mRNA, and based on the indicated "shift in mTOR products," the expression of mTOR was N-terminally truncated. Nevertheless, the "B10" indicated clone (shown by arrow in FIG. 17) provided a unique clonal cell line since it contained genomic modifications to EIF4EBP1, EIF4EBP2, and MTOR, resulting in knockout of 4E-BP1 and 4E-BP2 protein and dramatically reduced mTOR expression and activity.

TABLE 7 mTOR CRISPR primers

| Target/Purpose | Forward Primer/Oligo | Reverse Primer/Oligo |
| --- | --- | --- |
| mTOR CRISPR top strand between exons 3 and 4 | GATCG AATGAAATTTAAGAAGCCCG G [SEQ. ID.NO: 69] | AAAAC CGGGCTTCTTAAATTTCATT C [SEQ. ID.NO: 70] |
| mTOR CRISPR bottom strand between exons 3 and 4 | GATCG ATGAACTAGTATCCAGTAAG G [SEQ. ID.NO: 71] | AAAAC CTTACTGGATACTAGTTCAT C [SEQ. ID.NO: 72] |
| mTOR CRISPR top strand between exons 2 and 3 | GATCG TACTAGAAAGAACCTAGGAC G [SEQ. ID.NO: 73] | AAAAC GTCCTAGGTTCTTTCTAGTA C [SEQ. ID.NO: 74] |
| mTOR CRISPR bottom strand between exons 2 and 3 | GATCG ACTGTCTCTGACCTCAAGTC G [SEQ. ID.NO: 75] | AAAAC GACTTGAGGTCAGAGACAGT C [SEQ. ID.NO: 76] |
| mTOR genomic PCR | AAAGGCACCCAACCTGTCACATCCATAA AACATGCAG [SEQ. ID.NO: 77] | ATTTTCTCCCCTACCCCCCAAAAGGG AAA [SEQ. ID.NO: 78] |
| mTOR CRISPR top strand between exons 2 and 3-poor efficiency | GATCG CCTGGTACTAGAAAGAACCT G [SEQ. ID.NO: 79] | AAAAC AGGTTCTTTCTAGTACCAGG C [SEQ. ID.NO: 80] |
| mTOR CRISPR bottom strand between exons 2 and 3-poor efficiency | GATCG TTTCTAGTACCAGGGATAAA G [SEQ. ID.NO: 81] | AAAAC TTTATCCCTGGTACTAGAAA C [SEQ. ID.NO: 82] |
| mTOR CRISPR top strand between exons 3 and 4-poor efficiency | GATCG GCTGCTAGAATTAAAAGCCA G [SEQ. ID.NO: 83] | AAAAC TGGCTTTTAATTCTAGCAGC C [SEQ. ID.NO: 84] |
| mTOR CRISPR bottom strand between exons 3 and 4-poor efficiency | GATCG TAGCAGCAGCCCTGGGCCAC G [SEQ. ID.NO: 85] | AAAAC GTGGCCCAGGGCTGCTGCTA C [SEQ. ID.NO: 86] |
| mTOR CRISPR verification between exons 2 and 3 genomic PCR | ATAACAGTGATTGGGATGGGTTTGGAG AGTT [SEQ. ID.NO: 87] | AGGAGGTATAGTTCAAACCAAAGAAG A [SEQ. ID.NO: 88] |
| mTOR CRISPR verification between exons 3 and 4 genomic PCR | AAGGTGGCATCTTGGCCATAGGTAA [SEQ. ID.NO: 89] | TCAGCTCTGGTAAACTGTCTGAAAAG [SEQ. ID.NO: 90] |

Example 18 Single-Cell Clone Having Reduced Endogenous mTOR Expression and Activity Using the newly generated single-cell clone B10, which exhibited the greatest reduction in endogenous mTOR expression and activity, we stably transfected SB-eIF4E and transiently transfected LB-4E-BP2 and either WT or S2035I mTOR. These data were a replication of that in FIG. 16 with the new clone containing reduced mTOR expression. FIG. 18 shows a cleaner difference between the WT and S2035I mTOR in response to rapamycin and everolimus treatment, while maintaining a concentration-dependent increase for both mTORs with either INK128 or AZD2014 treatment.

Example 19 Differences with CRISPR Modified MTOR Cell Clones

Recently, Wu et al., 2015 (Cell Reports) described the L2185A mutation, which reduced the binding of ATP-competitive mTOR inhibitors like INK128. We therefore compared the originating parent clone (3A1) with knockout of 4E-BP1 and 4E-BP2 and stably expressing SB-eIF4E versus the two clones with CRISPR-modified MTOR also stably expressing SB-eIF4E. We transiently expressed LB-4E-BP2 and either WT or L2185A mTOR in each of these clonal systems to determine the ability to detect the effects of the L2185A mutation (FIG. 19). With INK128 treatment, we found less than one-log shift in EC50 with the parent clone with intact endogenous mTOR (FIG. 19A). The E2 cell clone produced over a one-log shift (FIG. 19B), and the B10 cell clone produced greater than a 1.5-log shift in EC50 (FIG. 19C). The approximately 1-1.5-log shift was previously observed using Western blot analysis comparing the WT mTOR cell line versus a stable cell line with genomically modified mTOR to contain the L2185A mutation (Wu et al., 2015). Therefore, our assay with the CRISPR-modified MTOR cell clone performed at least as good, if not better, than this previously published method.

Figure 20A:
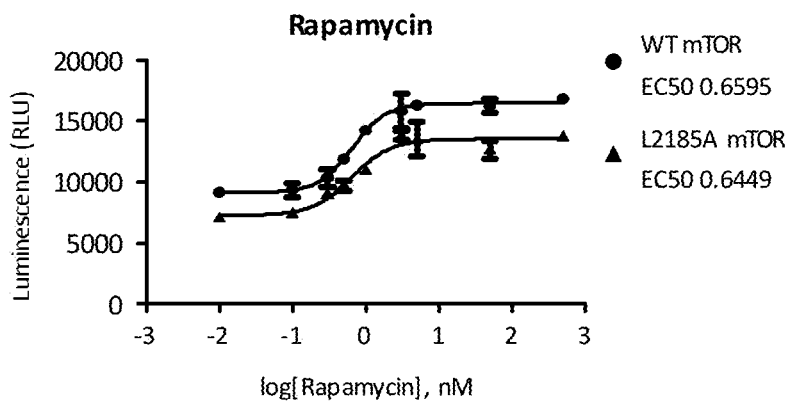
FIG. 20A, FIG. 20B, and FIG. 20C depict concentration-dependent effects of rapamycin, INK128, and AZD2014, respectively, on effects of mTOR mutations using the B10 clone with 4E-BP1 and 4E-BP2 deletion, and MTOR genomic modification, stably expressing SB-eIF4E and transiently expressing LB-4E-BP2 and WT or L2185A mTOR.
Figure 20B:
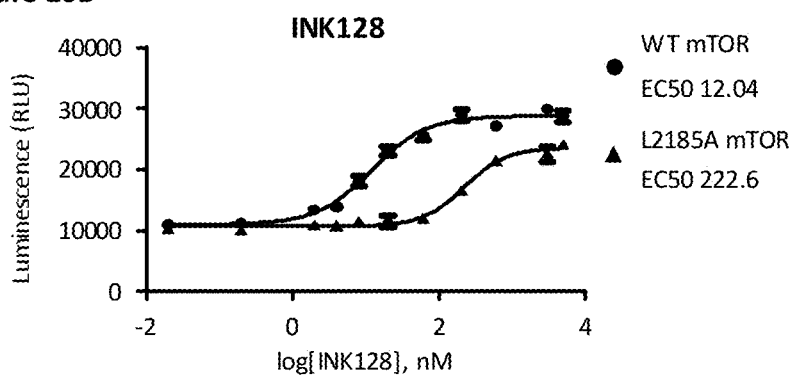
Figure 20C:
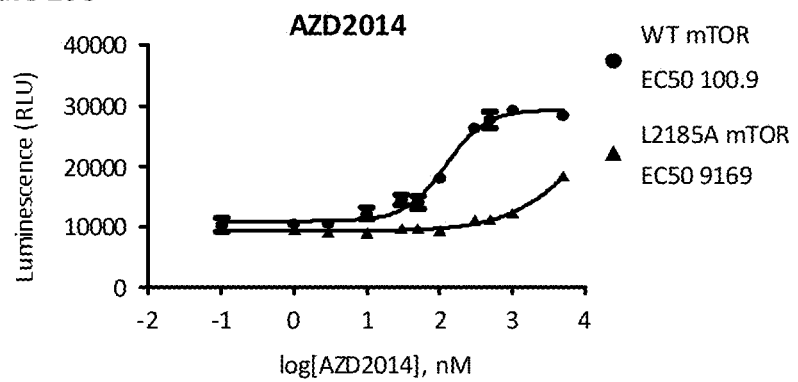

Example 20 Differential Drug Response with mTOR Variant in B10 Cell Clone Stably Expressing SB-eIF4E With the goal of our assay to measure the effects of mTOR mutations in combination with different types of mTOR inhibitors, we performed our assay using the B10 cell clone stably expressing SB-eIF4E and transiently expressing LB-4E-BP2 and either WT or L2185A mTOR. Rapamycin produced a concentration-dependent increase in both mTORs; however, both INK128 and AZD2014 exhibited a greater-than one log shift with L2185A mTOR from that of WT mTOR (FIG. 20). Therefore, our assay is capable of identifying specific rapamycin-resistant mutations in mTOR and mutations or variants that would reduce the efficacy of other classes of mTOR inhibitors.

Example 21 Phospho-Mimetic Mutations in 4E-BP1

Figure 21:
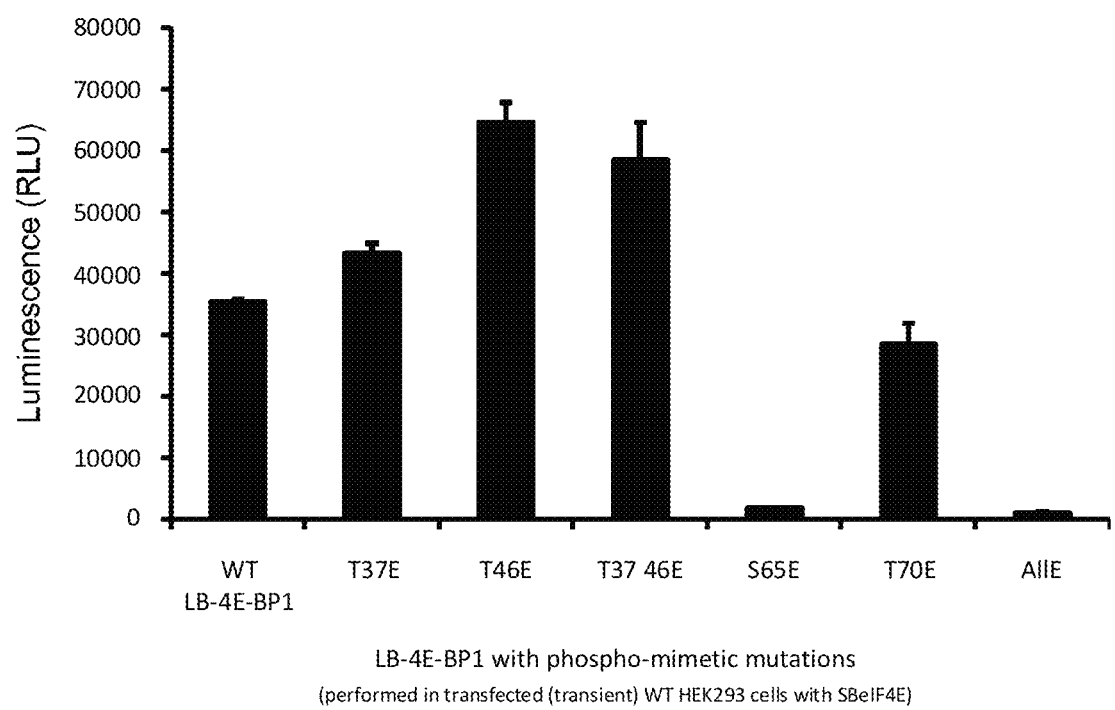
FIG. 21 depicts the phospho-mimetic mutations in 4E-BP1 that selectively alter the ability of 4E-BP1 to bind to eIF4E. Site-directed mutagenesis of phosphorylation sites from threonine residues (T) or serine (S) into glutamate (E) residues were performed on LB-4E-BP1 and transfected with SB-eIF4E into HEK293 cells. The additional S65E mutation in 4E-BP1 shows that this residue is important for binding to eIF4E.

Structural analysis of the interaction of 4E-BP1 and eIF4E show residue S65 of 4E-BP1 directly adjacent to the binding domain (Marcotrigiano et al., 1999). Since S65 of 4E-BP1 can also be phosphorylated by mTOR, we created a site-directed mutation of this residue to E to replicate a phosphorylated residue. We then transfected HEK293 cells with each of the phospho-mimetic mutations to expand on the data provided in FIG. 6. The primers used to create the site-directed mutagenesis are provided in Table 3. As shown before, independent mutations at sites T37, T46, or T70 do not alter the signal and therefore the binding of 4E-BP1 with eIF4E (FIG. 21). However, mutation of S65 to E significantly reduces the signal to levels similar to the 4E-BP1 containing all 4 mutations, suggesting that this residue's phosphorylation is responsible for the lack of interaction between 4E-BP1 and eIF4E caused by mTOR activity.

TABLE 8

Linear 4E-BP1/2 expression PCR

| Target/Purpose | Forward Primer | Reverse Primer |
|---|---|---|
| 4EBP1-R56W | GTACCAGGATCATCTATGAC TGG AAATTCCTGATGGAGTGTCG [SEQ. ID.NO: 91] | CGACACTCCATCAGGAATTT CCA GTCATAGATGATCCTGGTAC [SEQ. ID.NO: 92] |
| 4EBP1-L59Q | TCATCTATGACCGGAAATTC CAG ATGGAGTGTCGGAACTCACCT [SEQ. ID.NO: 93] | AGGTGAGTTCCGACACTCCAT CTG GAATTTCCGGTCATAGATGA [SEQ. ID.NO: 94] |
| 4EBP2-R62P | ACAGAAAGTTTCTGTTGGAT CCT CGCAATTCTCCCATGGCTCA [SEQ. ID.NO: 95] | TGAGCCATGGGAGAATTGCG AGG ATCCAACAGAAACTTTCTGT [SEQ. ID.NO: 96] |
| 4EBP2-D55Y | GAGGAACTCGAATCATTTAT TAC AGAAAGTTTCTGTTGGATCG [SEQ. ID.NO: 97] | CGATCCAACAGAAACTTTCT GTA ATAAATGATTCGAGTTCCTC [SEQ. ID.NO: 98] |
| Linear 4E-BP1/2 expression PCR | ACTGGCCGGTACCTGAGTCTAAATGAGT CT [SEQ. ID.NO: 99] | AAGGAGCTGACTGGGTTGAAGGCT [SEQ. ID.NO: 100] |

Example 22 Mutations in 4E-BP1 Tested in Cells with Genomic Modification of EIF4EBP1 and EIF4EBP2

Figure 22:
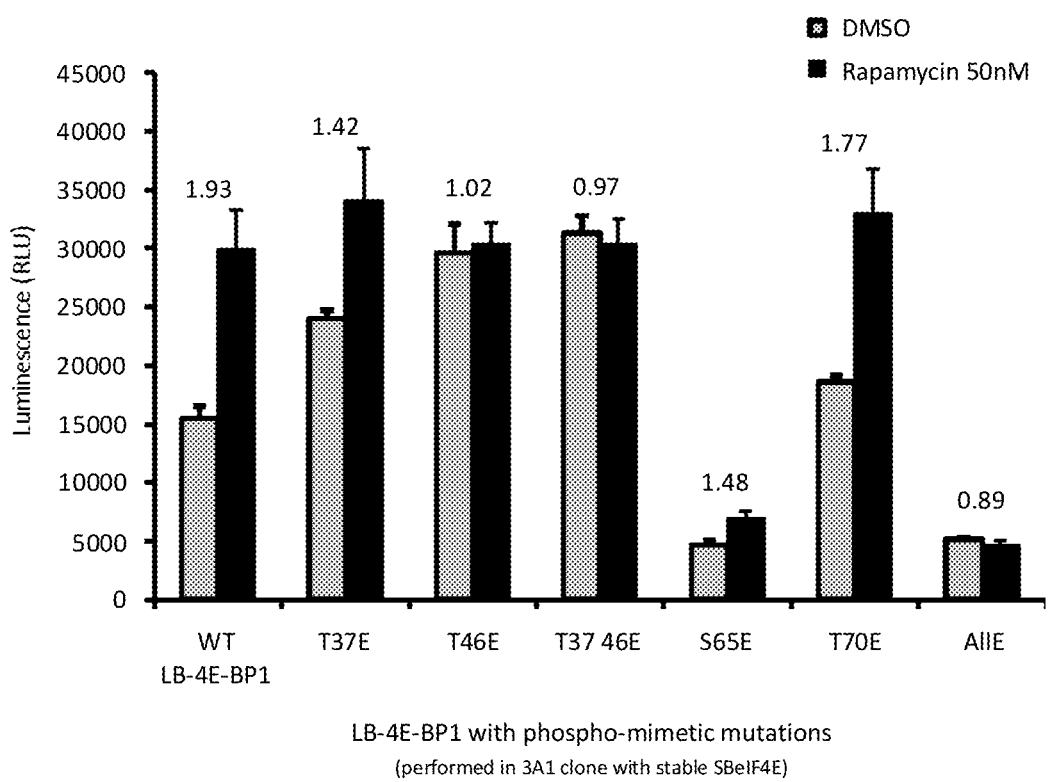
FIG. 22 depicts the phospho-mimetic mutations in 4E-BP1 that selectively alter the ability of 4E-BP1 to bind to eIF4E in the 3A1 cell line with 4E-BP1 and 4E-BP2 knockout, stably expressing SB-eIF4E and transiently expressing LB-4E-BP1 with the indicated mutation. Each condition was also treated with rapamycin to examine the responsiveness to mTOR inhibitors. Results reveal that the T46 residue is predominantly responsible for responsiveness to mTOR inhibitors, while the S65 residue is responsible for binding to eIF4E.

To examine if endogenous 4E-BP1 and 4E-BP2 may be conflicting with the observed changes, or lack of observed changes, in the mutations to 4E-BP1 as observed in FIG. 2l, we transfected the 3A1 clone with knockout of 4E-BP1 and 4E-BP2 protein and stably expressing SB-eIF4E with LB-4E-BP1 containing the phospho-mimetic mutations. In addition, we examined if the phospho-mimetics changed the ability of the interaction to respond to rapamycin. We found that, similar to above, only the S65E or all mutated to E fundamentally obstructed the binding of 4E-BP1 to eIF4E (FIG. 22). However, we also found that the mutation of T46E prevented response to rapamycin treatment (also observed in combinations of T37/46E and all E conditions), while S65E still responded to rapamycin. The fold-change resulting from rapamycin treatment is indicated above the bars. Therefore the T46 residue is responsible for the response by mTOR inhibitors, and the S65 residue is primarily responsible for binding to eIF4E. Given the multifaceted effect of the different phosphorylation sites towards the downstream binding and therefore translation effect caused by mTOR, our assay provides an enhanced method of measuring mTOR variants, mTOR inhibitors, and 4E-BP variants.

Example 23 Mutations in 4E-BP can Prevent Interaction with eIF4E eIF4E is a major effector in mTOR-mediated protein translation (Graves et al., 1995; Haghighat et al., 1995; Beretta et al., 1996). Based on the ability to greatly remove mTOR activity from a cell line no longer expressing 4E-BP1 or 4E-BP2, our results suggest that in the absence of functional 4E-BP1 or 4E-BP2, mTOR inhibitors would lose efficacy. However, clinically associated mutations in 4E-BP1 or 4E-BP2 have not been previously examined in relationship to their functionality.

Figure 23A:
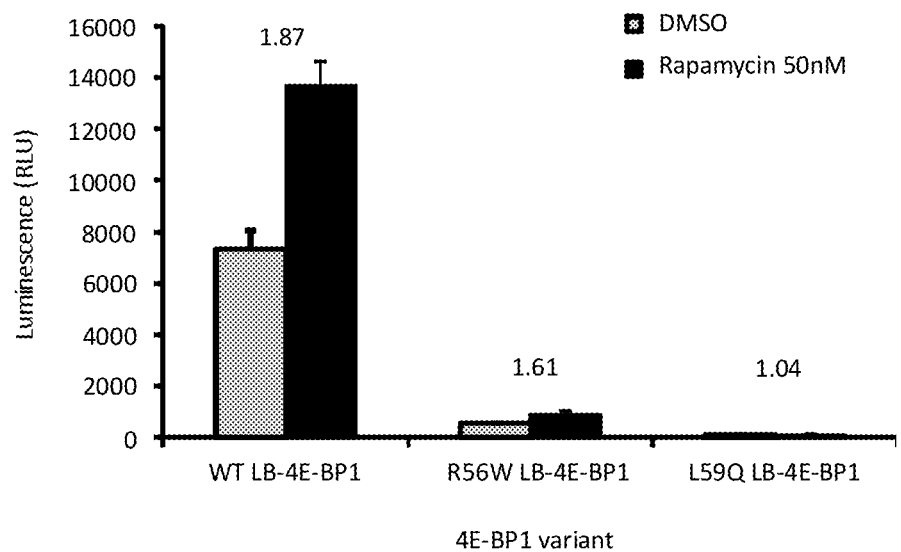
FIG. 23A and FIG. 23B depict patient mutations in EIF4EBP1 and EIF4EBP2, respectively, which were acquired from the COSMIC database and then tested in the 3A1 cell line with 4E-BP1 and 4E-BP2 deletion, stably expressing SB-eIF4E and transiently expressing LB-4E-BP1 or LB-4E-BP2 with the indicated mutation. Each condition was also treated with rapamycin to examine the responsiveness to mTOR inhibitors. Data shows that the patient mutations in 4E-BPs obstruct binding to eIF4E and do not respond to mTOR inhibitors.
Figure 23B:
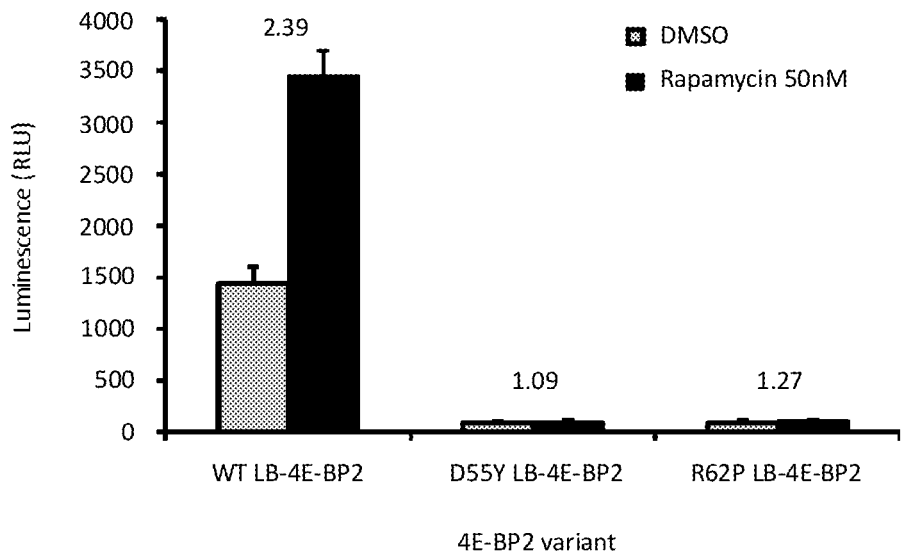

We reviewed the COSMIC database on reported somatic mutations in tumors and selected 2 mutations each in EIF4EBP1 and EIF4EBP2. We then created mutations in the cDNA by linear expression vector procedures in LB-4E-BP1 or LB-4E-BP2. The 3A1 cell line stably expressing SB-eIF4E was then transfected with these created cDNAs and compared to linear WT LB-4E-BP1 or WT LB-4E-BP2. The primers used to create the patient mutations are indicated in Table 8. We found that all 4 of these new mutations obstructed binding with SB-eIF4E (FIG. 23). One of the mutations (R56W LB-4E-BP1) may have retained a small level of binding, since it responded to mTOR inhibitors, as indicated by an increase in luminescence after rapamycin treatment. However, the others did not respond to rapamycin and each had minimal luminescence.

Figure 24:
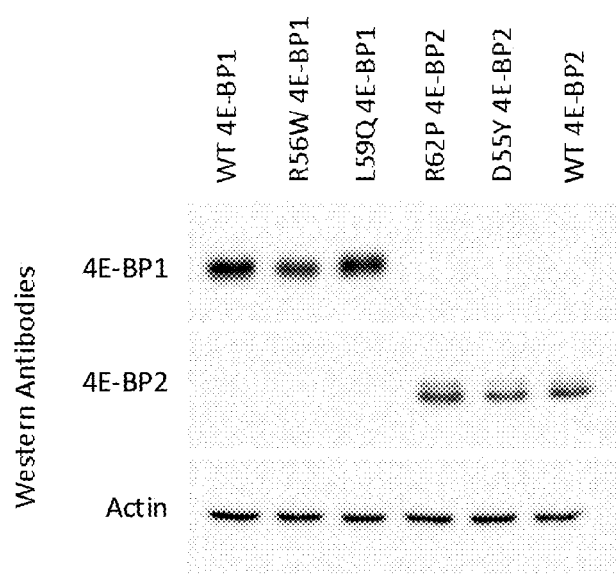
FIG. 24 depicts Western blot analyses performed on samples expressing either WT or patient mutations in 4E-BPs. Replicate Western blots were performed for antibodies specific to 4E-BP1, 4E-BP2, or actin. Results show no difference in expression between WT and mutant 4E-BPs.

To confirm that the newly created 4E-BP mutants did not affect expression, which could also affect the observed luminescence, we performed Western blot analysis with replicate cells that were transfected, as above. We found expression of each 4E-BP was similar (FIG. 24), showing that the altered binding is directly caused by the mutation in the 4E-BPs. Therefore the SB-eIF4E/LB-4E-BP assay is also capable of identifying 4E-BP patient variants that may reduce efficacy of mTOR inhibitors.

Procedures
Subcloning into NanoBiT Vectors

We performed PCR using primers designed to ligate full-length or truncated eIF4E or 4E-BP1 (or 4E-BP2) cDNA into NanoBiT vectors pBiT2.1-N [TK/SmBiT] or pBiT1.1-N [TK/LgBiT], respectively. Both sets of primers incorporated XhoI sites at the 5' end to facilitate ligation into the vectors, and both were designed so that the resulting sequence remained in frame for translation. The 3' end primers contained a stop codon (TAA), followed by XbaI sites for ligation into the vector. Primers used for subcloning are listed in Table 2. The originating cDNAs used for PCR were RC207333 for eIF4E, RC201348 for 4E-BP1, and RC208664 for 4E-BP2 (Origene). PCRs were performed using 2×Q5 mastermix (25 µl; New England Biolabs), 10 ng DNA, 200 nM of each primer, in a final volume of 50 µl. PCR was run on a GeneAmp (Invitrogen) with the following program: 98° C. for 2 min, followed by 98° C. for 30 sec, 58° C. for 30 sec, 68° C. for 2 min for 35 cycles, and then 68° C. for 5 min, followed by 4° C. (at least 5 min). PCR products were resolved on a 1% agarose gel in 1× Tris Acid EDTA (TAE) buffer (Amresco) containing 10 µg/ml ethidium bromide. Product was visualized and excised with a scalpel. Purification of the PCR products was performed using Promega gel purification kit. Equal volume of membrane binding buffer in µl was added to the excised gel piece in mg and heated to 55° C. for up to 30 min and mixed by inversion to dissolve. The resulting mix was pipetted into the Promega spin column and centrifuged at 18,000×g for 1 min. The flow-through is discarded, and the column is washed twice by pipetting 700 µl then 500 µl into the spin column, with each wash followed by centrifugation at 18,000×g for 1 min then discard of the flow-through. After the second wash, the column was the dry spun at 18,000×g for at least 5 min. The column was then placed in a fresh eppendorf tube, and 40 µl of MilliQ water (Millipore) is added to the column and incubated for 3 min. The column is then spun into the eppendorf tube at 18,000×g for 1 min.

Restriction Digest and Purification

To the purified DNA, we added 5 µl of 10× cutsmart buffer, 1 µl of XhoI and 1 µl of XbaI in a final reaction volume of 50 µl. Similarly, a 50 µl reaction volume was set up with 3 µg of pBiT1.1-N [TK/LgBiT] or pBiT2.1-N [TK/SmBiT] vectors with XhoI and XbaI. The mixture was mixed and incubated at 37° C. for 3 hours, after which the DNA was purified using the same gel purification procedures using the Promega gel purification kit, as described above.

DNA Plasmid Ligation, Bacterial Transformation, and DNA Amplification

For the ligation of the resultant products, 3- to 5-fold more by molarity of the eIF4E or 4E-BP1 (or 4E-BP2) digested PCR product was set up with pBiT2.1-N [TK/SmBiT] or pBiT1.1-N [TK/LgBiT], respectively, with 2 µl 5× ligation buffer and 0.5 µl T4 DNA ligase in a final volume of 10 µl (ExpressLink T4 Ligase, Invitrogen). The resultant mixture was incubated at room temperature (RT) for 2-3 hours. After which, 1 µl of the reaction was transformed into Top10 chemically-competent *E coli*. The transformation was performed by incubating on ice 50 µl of Top10 cells with 1 µl of ligation reaction for 20 min, followed by heat-shock for 50 sec at 45° C., and then re-incubation on ice for 2-3 min. Cells were then incubated at 37° C. with shaking at 250 rpm for 20-30 min. After which cells were plated on pre-prepared Luria broth (LB) agar 10 cm plates containing 100 µg/ml ampicillin. Plates were then incubated overnight at 37° C.

Colonies which developed on the LB agar plates were selected and screened for those containing the eIF4E or 4E-BP1 (or 4E-BP2) insert by colony PCR. Primers designed to extend from before the LB or SB region of the vectors (Table 2) were used to amplify the DNA contained in the vectors. The PCR mix and conditions were the same as indicated above, except that instead of using DNA, a scrape of the bacterial colony was added to the tube. The tip scraping the colony was subsequently scraped onto a fresh LB agar plate containing ampicillin and incubated at 37° C. for at least 6 hours. After the running of the PCR, the resulting products were resolved on a 1% agarose gel in TAE buffer containing ethidium bromide. The larger products were determined by size if they contained the insert. These bacterial colonies were then amplified by inoculation of LB broth containing 100 µg/ml of ampicillin and incubated overnight at 37° C.

DNA was then isolated from the resulting bacterial culture by miniprep procedures (Qiagen). The bacterial cultures were pelleted for concentration and re-suspended into 250 µl of Buffer P1 (50 mM Tris-HCl pH 8.0, 10 mM EDTA, 100 µg/ml RNaseA). Afterwards 250 µl of Buffer P2 (200 mM NaOH, 1% SDS) was added and mixed by inversion, then Buffer N3 (4.2 M Gu-HCl, 0.9 M potassium acetate, pH 4.8) was added and mixed by inversion. The resulting lysate was then centrifuged at 18,000×g for at least 10 min. The supernatant was removed and added to a Qiagen spin-column and centrifuged at 18,000×g for 1 min. The columns were then washed with 500 µl Buffer PB (5M Gu-HCl, 30% isopropanol), and centrifuged at 18,000×g for 1 min, followed by wash with Buffer PE (10 mM Tris-HCl pH 7.5, 80% ethanol), and centrifuged at 18,000×g for 1 min. Afterwards, the columns were dry spun at 18,000×g for at least 5 min. DNA was eluted into 40 µl, and sequence was verified by Sanger sequencing (Genewiz).

Transfection of HEK293 Cells for Luciferase Assay

HEK293 cells (ATCC) were maintained in Dulbucco's Modified Eagle's Media (DMEM) containing 4500 mg/L glucose, 4 mM L-glutamine, 10% fetal bovine serum (FBS), 100 U/ml of penicillin, and 100 µg/ml streptomycin (each component from Invitrogen). For transfection, HEK293 cells were washed with phosphate buffered saline, pH7.4 (PBS), trypsinized with 2 ml of trypsin 0.25% EDTA in Hank's Buffered Saline Solution ("trypsin"), and titrated in DMEM with supplements. Cells were then diluted to a concentration of $3 \times 10^5$ cells/ml. For each ml of cells to be transfected, 1 µg of DNA (total) was incubated with 2 µl of TransIT-293 reagent (Mirus Bio) in 100 µl of Opti-Mem (Invitrogen) for 30 min. Transfection mix was the added drop-wise to diluted HEK293 cells and titrated to mix. Afterwards, 100 µl of cells were plated per well of a 96-well plate.

Transfection of MCF-7 Cells for Luciferase Assay

MCF-7 cells (ATCC) were maintained in Eagle's Minimum Essential Media (EMEM; Corning) containing 1.5 g/L sodium bicarbonate, non-essential amino acids, L-glutamine, and sodium pyruvate, supplemented with 10% fetal bovine serum (FBS), 100 U/ml of penicillin, and 100 µg/ml streptomycin. For transfection, media and trypsin were pre-warmed to 37° C. Cells were washed with 7 ml of PBS, and then 1.5 ml of trypsin was added. Cells were titrated in 10 ml of media and diluted to a concentration of $3 \times 10^5$ cells/ml. For each ml of cells to be transfected, 1 µg of DNA (total) was incubated with 2 µl of TransfeX reagent (ATCC) in 100 µl of Opti-Mem (Invitrogen) for 15 min. Transfection mix was the added drop-wise to diluted MCF-7 cells and titrated to mix. Afterwards, 100 µl of cells were plated per well of a 96-well plate.

Luciferase Assay

Approximately 18-24 hours after transfection and plating of cells (unless otherwise stated), cells were treated with indicated inhibitor or vehicle at the indicated concentration for 1 h, unless otherwise specified. Treatment was completed by diluting the drug in DMEM at a 5× concentration of the final treatment concentration, for instance, for a 50 nM treatment, drug was added to the media at a concentration of 250 nM. Then DMEM plus drug was added to the wells at a 25% increase in volume—for example for 100 µl of cells and media in the wells of a 96-well plate, 25 µl of media plus drug was added. The final concentration of dimethyl sulfoxide (DMSO, vehicle) in the wells did not exceed 0.1% for any treatment. Each treatment was matched by the appropriate vehicle control. After treatment, media was removed and replaced by NanoGlo (Promega) buffer plus substrate diluted in PBS, such that each well received 50 µl of NanoGlo containing 1 µl of substrate and was diluted with 100 µl of PBS. Cells were titrated with a pipette and then pipetted into an opaque white 96-well plate (Corning). NanoGlo luminescence was measured at 470 nm on a Spectromax L with 1 or 2 sec integration time. Relative intensities were captured and represented as relative luminescence units (RLU).

Site-Directed Mutagenesis

Site-directed mutagenesis was performed using the QuickChange protocol by Agilent. Primers were designed as indicated in Tables 3 and 4. The PCR reaction contained 1× of the reaction buffer, 10 µg of the cDNA to be altered, 125 ng of each primer, 1 µl of a 10 mM dNTP mix, and 1 µl of PfuUltra DNA polymerase in a 51 µl reaction. The PCR was run on a GeneAmp (Invitrogen) with the following program: 95° C. for 2 min, followed by 95° C. for 30 sec, 58° C. for 30 sec, 68° C. for 3 min or 13 min (3 min for 4E-BP1 and 13 min for mTOR) for 18 cycles, followed by 4° C. (at least 5 min).

After completion of the PCR, 1 µl of DpnI restriction enzyme was added to the reaction and mixed, followed by incubation at 37° C. for 2 h. After which, 1 µl of the reaction was transformed into Top10 chemically-competent *E coli*, as indicated above in the "Subcloning into NanoBiT vectors" subsection. Mutation insertion was verified by Sanger sequencing.

Creation of Stable Cell Lines

The hygromycin expression cassette was removed from pNL2.2 (Promega) with restriction digest enzymes BamHI and SalI, using a 50 µl digest reaction, followed by resolving on a 1% agarose gel and isolation using the Promega gel purification kit, as above. The pBiT2.1-N [TK/SmBiT] plasmid containing SB-eIF4E was concurrently digested with BamHI and SalI, and purified. The hygromycin expression cassette was then ligated into the pBiT2.1-N [TK/SmBiT] plasmid containing SB-eIF4E, as indicated above. The insertion of the cassette was verified by restriction digest of the minipreps, followed by Sanger sequencing.

For transfection, 6-well plates were precoated with 10 µg/ml of poly-D-lysine (Sigma), and washed 3 times with PBS, prior to plating HEK293 cells at $5 \times 10^4$ cells/ml with 2 ml per well. One day after plating, the SB-eIF4E pBiT2.1-N+Hygromycin and the LB-4E-BP1 or LB-4E-BP2 pBiT1.1-N were transfected using Calcium Phosphate Precipitation (Current Protocols of Molecular Biology; Waxman and Giasson, 2010). A total of 3 µg of DNA, split equally with each plasmid, was diluted into $CaCl_2$ (0.5M)

for a total volume of 37.5 µl per well. After mixing, the DNA/CaCl2 mixture was added ⅕$^{th}$ at a time into an equal volume of 2×BES saline solution (50 mM N,N-bis(2-hydroxyethyl)-2-aminoethanesulfonic acid (BES), 280 mM NaCl, 1.5 mM Na$_2$HPO$_4$, pH 6.96), vortexing in between each addition, and creating a final volume of 75 µl of transfection solution per well. The transfection solution was incubated at room temperature for 17-20 min, after which fresh warm media was exchanged on the HEK293 cells and the transfection solution was added on top in a dropwise manner. Approximately 18-24 hours after transfection, the media was removed and cells were washed 2 times with PBS, and fresh warm media was replaced on the cells.

Three to five days after transfection, the transfected cells were trypsinized and replated on to 6-count of 10 cm plates containing 300 µg/ml of hygromycin (ThermoFisher). For 7 days, media was replaced every 2-3 days with fresh hygromycin, after which cells were trypsinized, pooled and concentrated, and counted for plating as single cells on to 96-well plates. Fifty ml containing 400 cells were plated on to 5-count of 96-well plates with each well containing 100 µl of media+cell. DMEM conditioned with previous incubation with HEK293 cells was saved, filtered, and used for single-cell plating. The remainder of the hygromycin treated cells was then pooled and used as "stable pools" for experimentation.

Approximately 3 weeks after the plating of single-cell clones, cell colonies that reached at least 20% confluency were split 1/3 into 96-wells, such that 1 wells was maintained separately for passage, and 2 wells were plated for experimentation. 1-2 days after plating, one of the experimentation wells were treated with DMSO (0.01%), and the other well was treated with rapamycin (50 nM final), and then assayed for luciferase, as above. Clones with a basal signal above 1000 relative light units (RLU) and responsiveness to rapamycin were maintained and assays were performed to validate their use.

For transfection of single-cell clones or pools to validate for the assay, cells were transfected by TransIT-293 as indicated above, in the "Transfection of HEK293 cells for luciferase assay" subsection.

Generation of CRISPR Knock-Out Clonal Cell Lines

CRISPR single-guide RNAs (sgRNA) were designed against the genomic area corresponding to N-terminal domains of 4E-BP1 and 4E-BP2. For MTOR sgRNAs were designed against the intronic regions flanking Exon 3. Complement oligonucleotides were ordered with overhangs on the top strand of gatcg on the 5' end and g on the 3' end and overhangs on the bottom strand of aaaac on the 5' end and c on the 3' end. Oligonucleotides were annealed to each other by dilution to 1 µM in 10 mM Tris, pH 8.4 and then incubation to 95° C. for 2 min in a PCR machine, followed by gradual reduction in temperature to room temperature, over the course of 1 h, accomplished by turning off the PCR machine. The resulting double-stranded oligonucleotide was then ligated into pCas-Guide-Nickase plasmid (Origene), previously digested with restriction enzymes BsmBI and BamHI and purified, as indicated above.

CRISPR clones were verified by co-transfecting top and bottom strand pairs, followed by genomic PCR, using the primers indicated in Table 2 and Table 7. Genomic DNA was isolated using either the Promega genomic DNA isolation kit (low throughput), or the Zymed genomic DNA isolation kit (96-well format). Genomic PCR was completed using OneTaq (New England Biolabs). Isolated genomic DNA (2-3 µl) was added to 1× of 5× OneTaq reaction buffer, containing 0.2 µM of each primer, 200 µM dNTPs, and 0.125 µl of OneTaq enzyme in a 25 µl reaction. PCR was run with the following program: 94° C. for 2 min, followed by 94° C. for 30 sec, 58° C. for 30 sec, 68° C. for 1 min for 30 cycles, and then 68° C. for 3 min, followed by 4° C. (at least 5 min). PCR products were resolved and visualized on a 2% agarose gel. Clones deemed by genomic PCR to have each chromosomal strand of the gene modified were subsequently expanded for Western blot analyses.

Western Blot Analyses

Cells were harvested in 1.5× Laemmli buffer (75 mM Tris-HCl, pH 6.8, 3% SDS, 15% glycerol, 3.75 mM of EDTA, pH 7.4) and boiled. Protein concentration was determined by bicichoninic acid protein assay reagent (Pierce Thermo Scientific, Milwaukee, Wis.) or by A280 on a NanoDrop (Thermo Scientific). Samples were then incubated with dithiothreitol and bromphenol blue and heated to 100° C. for 10 min prior to Western blot analysis. Protein (10 or 15 µg) was resolved by SDS-PAGE gel electrophoresis (12% gels for 4E-BP1/2, S6, and actin; 7% gels for mTOR), followed by electrophoretic transfer onto nitrocellulose membranes (Bio-Rad). Membranes were blocked in Tris-buffered saline (TBS) with 5% dry milk, and then incubated overnight with antibodies directed towards 4E-BP1 (1:1000 dilution in TBS with 5% bovine serum albumin (BSA)), 4E-BP2 (1:500 in TBS with 5% BSA), phospho-S6 (1:1000 in TBS with 5% BSA), actin (1:2000 in TBS with 5% dry milk; Sigma), or mTOR (1:1000 in TBS with 5% dry milk). All antibodies were obtained by Cell Signaling Technology (Danvers, Mass.) unless otherwise specified.

Following overnight incubation with primary antibodies, and 3 washes with TBS, membranes were incubated with goat anti-rabbit (for 4E-BP1/2, phospho-S6, and actin) or goat anti-mouse (for mTOR) conjugated horseradish peroxidase secondary antibodies diluted at 1:2000 in TBS with 5% dry milk for 90 min at room temperature. Membranes were then washed 3 times with TBS, followed by 1 min incubation with chemiluminescence reagent (Advansta Western Bright, Menlo Park, Calif.) and image capture with an ImageQuant LAS4000 system and software (GE).

Generation of Linear Expression Cassette Containing Mutation in 4E-BP1/2

To produce the linear expression cassette for 4E-BP1 or 4E-BP2 containing the patient variant designed for mammalian cell transfection and expression, we performed a PCR using the "Linear 4E-BP1/2 expression PCR" forward primer Table 8 in conjunction with the reverse primer of the mutation we intended on creating, and a second PCR using the forward primer of the mutation we intended on creating with the "Linear 4E-BP1/2 expression PCR" reverse primer. For the implementation of the PCR, we used the Q5 enzyme (New England Biolabs) in the following mix: 1× of 5×Q5 buffer, 10 ng template, 0.2 mM dNTPs, 250 nM primers (each), 0.5 µl Q5 in each 50 µl reaction. The PCR was performed as 98° C. for 2 min, followed by 98° C. for 30 sec, 58° C. for 30 sec, 72° C. for 2 min for 30 cycles, and then 72° C. for 4 min, followed by 4° C. (at least 5 min). After completion of the PCR, products were resolved on a 1% agarose gel containing 1.6 µg/ml crystal violet for visualization. PCR products isolated by excision and purified using the Promega gel isolation kit (as indicated above). Afterwards, the purified DNA product concentrations were measured by NanoDrop, and concentration was determined by A260. For the completed mutated linear cassette, 1 µl of each N-terminal and C-terminal DNA piece created above was added as a template in the same PCR reaction mix, and cycled again, as above. The resulting PCR products were resolved again on a 1% agaorse gel containing 1.6 µg/ml crystal violet, excised, purified, and measured. The resulting product was then used for transfection into HEK293 cells.

Sequences

SEQ. ID. NO: 101:
atgcttggaa ccggacctgc cgccgccacc accgctgcca ccacatctag caatgtgagc
gtcctgcagc agtttgccag tggcctaaag agccggaatg aggaaaccag ggccaaagcc
gccaaggagc tccagcacta tgtcaccatg aactccgag agatgagtca agaggagtct
actcgcttct atgaccaact gaaccatcac attttttgaat tggtttccag ctcagatgcc
aatgagagga aaggtggcat cttggccata gctagcctca taggagtgga aggtgggaat
gccacccgaa ttggcagatt tgccaactat cttcggaacc tcctcccctc caatgaccca
gttgtcatgg aaatggcatc caaggccatt ggccgtcttg ccatggcagg ggacactttt
accgctgagt acgtggaatt tgaggtgaag cgagccctgg aatggctggg tgctgaccgc
aatgagggcc ggagacatgc agctgtcctg gttctccgtg agctggccat cagcgtccct
accttcttct tccagcaagt gcaacccttc tttgacaaca tttttgtggc cgtgtgggac
cccaaacagg ccatccgtga gggagctgta gccgcccttc gtgcctgtct gattctcaca
acccagcgtg agccgaagga gatgcagaag cctcagtggt acaggcacac atttgaagaa
gcagagaagg gatttgatga gaccttggcc aaagagaagg gcatgaatcg ggatgatcgg
atccatggag ccttgttgat ccttaacgag ctggtccgaa tcagcagcat ggagggagag
cgtctgagag aagaaatgga agaaatcaca cagcagcagc tggtacacga caagtactgc
aaagatctca tgggcttcgg aacaaaacct cgtcacatta cccccttcac cagtttccag
gctgtacagc cccagcagtc aaatgccttg gtggggctgc tggggtacag ctctcaccaa
ggcctcatgg gatttgggac ctcccccagt ccagctaagt ccaccctggt ggagagccgg
tgttgcagag acttgatgga ggagaaattt gatcaggtgt gccagtgggt gctgaaatgc
aggaatagca agaactcgct gatccaaatg acaatcctta atttgttgcc ccgcttggct
gcattccgac cttctgcctt cacagatacc cagtatctcc aagataccat gaaccatgtc
ctaagctgtg tcaagaagga gaaggaacgt acagcggcct tccaagccct ggggctactt
tctgtggctg tgaggtctga gtttaaggtc tatttgcctc gcgtgctgga catcatccga
gcggccctgc ccccaaagga cttcgcccat aagaggcaga aggcaatgca ggtggatgcc
acagtcttca cttgcatcag catgctggct cgagcaatgg ggccaggcat ccagcaggat
atcaaggagc tgctggagcc catgctggca gtgggactaa gccctgccct cactgcagtg
ctctacgacc tgagccgtca gattccacag ctaaagaagg acattcaaga tgggctactg
aaaatgctgt ccctggtcct tatgcacaaa cccttcgcc acccaggcat gcccaagggc
ctggcccatc agctggcctc tcctggcctc acgaccctcc ctgaggccag cgatgtgggc
agcatcactc ttgccctccg aacgcttggc agctttgaat ttgaaggcca ctctctgacc
caatttgttc gccactgtgc ggatcatttc ctgaacagtg agcacaagga gatccgcatg
gaggctgccc gcacctgctc ccgcctgctc acaccctcca tccacctcat cagtggccat
gctcatgtgg ttagccagac cgcagtgcaa gtggtggcag atgtgcttag caaactgctc
gtagttggga taacagatcc tgaccctgac attcgctact gtgtcttggc gtccctggac
gagcgctttg atgcacacct ggcccaggcg gagaacttgc aggccttgtt tgtggctctg
aatgaccagg tgtttgagat ccgggagctg gccatctgca ctgtgggccg actcagtagc
atgaaccctg cctttgtcat gccttttcctg cgcaagatgc tcatccagat tttgacagag
ttggagcaca gtgggattgg aagaatcaaa gagcagagtg cccgcatgct ggggcacctg
gtctccaatg ccccccgact catccgcccc tacatggagc ctattctgaa ggcattaatt -continued

```
ttgaaactga aagatccaga ccctgatcca aacccaggtg tgatcaataa tgtcctggca acaataggag aattggcaca ggttagtggc ctggaaatga ggaaatgggt tgatgaactt tttattatca tcatggacat gctccaggat tcctctttgt tggccaaaag gcaggtggct ctgtggaccc tgggacagtt ggtggccagc actggctatg tagtagagcc ctacaggaag taccctactt tgcttgaggt gctactgaat tttctgaaga ctgagcagaa ccagggtaca cgcagagagg ccatccgtgt gttagggctt ttagggctt tggatcctta caagcacaaa gtgaacattg gcatgataga ccagtcccgg gatgcctctg ctgtcagcct gtcagaatcc aagtcaagtc aggattcctc tgactatagc actagtgaaa tgctggtcaa catgggaaac ttgcctctgg atgagttcta cccagctgtg tccatggtgg ccctgatgcg gatcttccga gaccagtcac tctctcatca tcacaccatg gttgtccagg ccatcacctt catcttcaag tccctgggac tcaaatgtgt gcagttcctg ccccaggtca tgcccacgtt ccttaacgtc attcgagtct gtgatggggc catccgggaa tttttgttcc agcagctggg aatgttggtg tcctttgtga agagccacat cagacctttat atggatgaaa tagtcaccct catgagagaa ttctgggtca tgaacacctc aattcagagc acgatcattc ttctcattga gcaaattgtg gtagctcttg ggggtgaatt taagctctac ctgccccagc tgatcccaca catgctgcgt gtcttcatgc atgacaacag cccaggccgc attgtctcta tcaagttact ggctgcaatc cagctgtttg gcgccaacct ggatgactac ctgcatttac tgctgcctcc tattgttaag ttgtttgatg cccctgaagc tccactgcca tctcgaaagg cagcgctaga gactgtggac cgcctgacgg agtccctgga tttcactgac tatgcctccc ggatcattca ccctattgtt cgaacactgg accagagccc agaactgcgc tccacagcca tggacacgct gtcttcactt gtttttcagc tggggaagaa gtaccaaatt ttcattccaa tggtgaataa agttctggtg cgacaccgaa tcaatcatca gcgctatgat gtgctcatct gcagaattgt caagggatac acacttgctg atgaagagga ggatcctttg atttaccagc atcggatgct taggagtggc caagggggatg cattggctag tggaccagtg gaaacaggac ccatgaagaa actgcacgtc agcaccatca acctccaaaa ggcctgggc gctgccagga gggtctccaa agatgactgg ctggaatggc tgagacggct gagcctggag ctgctgaagg actcatcatc gccctccctg cgctcctgct gggccctggc acaggcctac aacccgatgg ccagggatct cttcaatgct gcatttgtgt cctgctggtc tgaactgaat gaagatcaac aggatgagct catcagaagc atcgagttgg ccctcacctc acaagacatc gctgaagtca cacagaccct cttaaacttg gctgaattca tggaacacag tgacaagggc cccctgccac tgagagatga caatggcatt gttctgctgg gtgagagagc tgccaagtgc gagcatatg ccaaagcact acactacaaa gaactggagt tccagaaagg ccccacccct gccattctag aatctctcat cagcattaat aataagctac agcagccgga ggcagcggcc ggagtgttag aatatgccat gaaacacttt ggagagctgg agatccaggc tacctggtat gagaaactgc acgagtggga ggatgccctt gtggcctatg acaagaaaat ggacaccaac aaggacgacc cagagctgat gctgggccgc atgcgctgcc tcgaggcctt ggggaatgg ggtcaactcc accagcagtg ctgtgaaaag tggaccctgg ttaatgatga acccaagcc aagatggccc ggatggctgc tgcagctgca tggggtttag gtcagtggga cagcatggaa gaatacacct gtatgatccc tcgggacacc catgatgggg cattttatag agctgtgctg gcactgcatc aggacctctt ctccttggca caacagtgca ttgacaaggc cagggacctg ctggatgctg aattaactgc gatgcagga gagagttaca gtcgggcata tgggggccatg gtttcttgcc acatgctgtc cgagctggag
```

-continued

```
gaggttatcc agtacaaact tgtccccgag cgacgagaga tcatccgcca gatctggtgg gagagactgc agggctgcca gcgtatcgta gaggactggc agaaaatcct tatggtgcgg tcccttgtgg tcagccctca tgaagacatg agaacctggc tcaagtatgc aagcctgtgc ggcaagagtg gcaggctggc tcttgctcat aaaactttag tgttgctcct gggagttgat ccgtctcggc aacttgacca tcctctgcca acagttcacc ctcaggtgac ctatgcctac atgaaaaaca tgtggaagag tgcccgcaag atcgatgcct ccagcacat gcagcatttt gtccagacca tgcagcaaca ggcccagcat gccatcgcta ctgaggacca gcagcataag caggaactgc acaagctcat ggcccgatgc ttcctgaaac ttggagagtg gcagctgaat ctacagggca tcaatgagag cacaatcccc aaagtgctgc agtactacag cgccgccaca gagcacgacc gcagctggta caaggcctgg catgcgtggg cagtgatgaa cttcgaagct gtgctacact acaaacatca gaaccaagcc cgcgatgaga agaagaaact gcgtcatgcc agcggggcca acatcaccaa cgccaccact gccgccacca cggccgccac tgccaccacc actgccagca ccgagggcag caacagtgag agcgaggccg agagcaccga gaacagcccc accccatcgc cgctgcagaa gaaggtcact gaggatctgt ccaaaaccct cctgatgtac acggtgcctg ccgtccaggg cttcttccgt tccatctcct tgtcacgagg caacaacctc caggatacac tcagagttct caccttatgg tttgattatg gtcactggcc agatgtcaat gaggccttag tggagggggt gaaagccatc cagattgata cctggctaca ggttatacct cagctcattg caagaattga tacgcccaga cccttggtgg gacgtctcat tcaccagctt ctcacagaca ttggtcggta ccaccccag gccctcatct acccactgac agtggcttct aagtctacca cgacagcccg gcacaatgca gccaacaaga ttctgaagaa catgtgtgag cacagcaaca ccctggtcca gcaggccatg atggtgagcg aggagctgat ccgagtggcc atcctctggc atgagatgtg gcatgaaggc ctggagagg catctcgttt gtactttggg gaaaggaacg tgaaaggcat gtttgaggtg ctggagcct tgcatgctat gatgaacgg ggcccccaga ctctgaagga aacatccttt aatcaggcct atggtcgaga tttaatggag gcccaagagt ggtgcaggaa gtacatgaaa tcagggaatg tcaaggacct caccaagcc tgggacctct attatcatgt gttccgacga atctcaaagc agctgcctca gctcacatcc ttagagctgc aatatgtttc cccaaaactt ctgatgtgcc gggaccttga attggctgtg ccaggaacat atgaccccaa ccagccaatc attcgcattc agtccatagc ccgtctttg caagtcatca catccaagca gaggccccgg aaattgacac ttatgggcag caacggacat gagtttgttt tccttctaaa aggccatgaa gatctgcgcc aggatgagcg tgtgatgcag ctcttcggcc tggttaacac ccttctggcc aatgacccaa catctcttcg gaaaaacctc agcatccaga gatacgctgt catccctta tcgaccaact cgggcctcat ggctgggtt ccccactgtg acacactgca cgccctcatc cgggactaca gggagaagaa gaagatcctt ctcaacatcg agcatcgcat catgttgcgg atggctccgg actatgacca cttgactctg atgcagaagg tggaggtgtt tgagcatgcc gtcaataata cagctgggga cgacctggcc aagctgctgt ggctgaaaag ccccagctcc gaggtgtggt tgaccgaag aaccaattat acccgttctt tagcggtcat gtcaatggtt gggtatattt taggcctggg agatagacac ccatccaacc tgatgctgga ccgtctgagt gggaagatcc tgcacattga ctttgggac tgctttgagg ttgctatgac ccgagagaag tttccagaga agattccatt tagactaaca agaatgttga ccaatgctat ggaggttaca ggcctggatg gcaactacag aatcacatgc cacacagtga tggaggtgct gcgagagcac aaggacagtg tcatggccgt gctggaagcc
```

-continued

```
tttgtctatg accccttgct gaactggagg ctgatggaca caaataccaa aggcaacaag cgatcccgaa cgaggacgga ttcctactct gctggccagt cagtcgaaat tttggacggt gtggaacttg gagagccagc ccataagaaa acggggacca cagtgccaga atctattcat tctttcattg gagacggttt ggtgaaacca gaggccctaa ataagaaagc tatccagatt attaacaggg ttcgagataa gctcactggt cgggacttct ctcatgatga cactttggat gttccaacgc aagttgagct gctcatcaaa caagcgacat cccatgaaaa cctctgccag tgctatattg gctggtgccc tttctggtaa
```

SEQ. ID. NO: 102
```
atgtccgggg gcagcagctg cagccagacc ccaagccggg ccatccccgc cactcgccgg gtggtgctcg gcgacggcgt gcagctcccg cccggggact acagcacgac ccccggcggc acgctcttca gcaccacccc gggaggtacc aggatcatct atgaccggaa attcctgatg gagtgtcgga actcacctgt gaccaaaaca ccccaaggg atctgcccac cattccgggg gtcaccagcc cttccagtga tgagcccccc atggaagcca gccagagcca cctgcgcaat agcccagaag ataagcgggc gggcggtgaa gagtcacagt ttgagatgga catttaa
```

SEQ. ID. NO: 103
```
atgtcctcgt cagccggcag cggccaccag cccagccaga gccgcgccat ccccacccgc accgtggcca tcagcgacgc cgcgcagcta cctcatgact attgcaccac gcccggggg acgctcttct ccaccacacc gggaggaact cgaatcattt atgacagaaa gtttctgttg gatcgtcgca attctcccat ggctcagacc ccaccctgcc acctgcccaa tatcccagga gtcactagcc ctggcacctt aattgaagac tccaaagtag aagtaaacaa tttgaacaac ttgaacaatc acgacaggaa acatgcagtt ggggatgatg ctcagttcga gatggacatc taa
```

SEQ. ID. NO: 104
```
atggcgactg tcgaaccgga aaccacccct actcctaatc ccccgactac agaagaggag aaaacggaat ctaatcagga ggttgctaac ccagaacact atattaaaca tccctacag aacagatggg cactctggtt ttttaaaaat gataaaagca aaacttggca agcaaacctg cggctgatct ccaagtttga tactgttgaa gactttggg ctctgtacaa ccatatccag ttgtctagta atttaatgcc tggctgtgac tactcacttt ttaaggatgg tattgagcct atgtgggaag atgagaaaaa caaacggggg ggacgatggc taattacatt gaacaaacag cagagacgaa gtgacctcga tcgcttttgg ctagagacac ttctgtgcct tattggagaa tcttttgatg actacagtga tgatgtatgt ggcgctgttg ttaatgttag agctaaaggt gataagatag caatatggac tactgaatgt gaaaacagag aagctgttac acatatagg agggtataca aggaaaggtt aggacttcct ccaaagatag tgattggtta tcagtcccac gcagacacag ctactaagag cggctccacc actaaaaata ggtttgttgt ttaa
```

REFERENCES

Kunz J, Henriquez R, Schneider U, Deuter-Reinhard M, Movva N R, Hall M N. Target of rapamycin in yeast, TOR2, is an essential phosphatidylinositol kinase homolog required for G1 progression. Cell 1993; 73:585-96.

Kuruvilla F G, Schrieber S L. The PIK-related kinases intercept conventional signaling pathways. Cell Biol 1999; 6:R129-36.

Graves L M, Bornfeldt K E, Argast G M, Krebs E G, Kong X, Lin T A, Lawrence J C Jr. cAMP- and rapamycin-sensitive regulation of the association of eurkaryotic initiation factor 4E and the translational regulator PHAS-I in aortic smooth muscle cells. Proc Natl Acad Sci USA 1995; 92:7222-6.

Haghighat A, Mader S, Pause A, Sonenberg N. Repression of cap-dependent translation by 4E-binding protein 1: competition with p220 for binding to eurkaryotic initiation factor-4E. EMBO J 1995; 14:5701-9.

Beretta L, Gingras A C, Svitkin Y V, Hall M N, Sonenberg N. Rapamycin blocks the phosphorylation of 4E-BP1 and inhibits cap-dependent initiation of translation. EMBO J 1996; 15:658-64.

Murakami M, Ichisaka T, Maeda M, Oshiro N, Hara K, Edenhofer F, Kiyama H, Yonezawa K, Yamanaka S.

mTOR is essential for growth and proliferation in early mouse embryos and embryonic stem cells. Mol Cell Biol 2004; 24:6710-8.

Zhang H, Stallock J P, Ng J C, Reinhard C, Neufeld T P. Regulation of cellular growth by the *Drosophila* target of rapamycin dTOR. Genes Dev 2000; 14:2712-24.

Brown E J, Albers M W, Shin T B, Ichikawa K, Keith C T, Lane W S, Schreiber S L. A mammalian protein targeted by G1-arresting rapamycin-receptor complex. Nature 1994; 369:756-8.

Grabiner B C, Nardi V, Birsoy K, Possemato R, Shen K, Sinha S, Jordan A, Beck A H, Sabatini D M. A diverse array of cancer-associated MTOR mutations are hyperactivating and can predict rapamycin sensitivity. Cancer Discov 2014; 4:554-63.

Wagle N, Grabiner B C, Van Allen E M, Amin-Mansour A, Taylor-Weiner A, Rosenberg M, Gray N, Barletta J A, Guo Y, Swanson S J, Ruan D T, Hanna G J, Haddad R I, Getz G, Kwiatkowski D J, Carter S L, Sabatini D M, Janne P A, Garraway L A, Lorch J H. Response and acquired resistance to everolimus in anaplastic thyroid cancer. N Engl J Med 2014; 371:1426-33.

Luker K E, Smith M C, Luker G D, Gammon S T, Piwnica-Worms H, Piwnica-Worms D. Kinetics of regulated protein-protein interactions revealed with firefly luciferase complementation imaging in cells and living animals. Proc Natl Acad Sci USA 2004; 101:12288-93.

Dixon A S, Schwinn M K, Hall M P, Zimmerman K, Otto P, Lubben T H, Butler B L, Binkowski B F, Machleidt T, Kirkland T A, Wood M G, Eggers C T, Encell L P, Wood K V. NanoLuc Complementation Reporter Optimized for Accurate Measurement of Protein Interactions in Cells. ACS Chem Biol 2016; 11:400-8.

Thoreen C C, Kang S A, Chang J W, Liu Q, Zhang J, Gao Y, Reichling L I, Sim T, Sabatini D M, Gray N S. An ATP-competitive mammalian target of rapamycin inhibitor reveals rapamycin-resistant functions of mTORC1. J Biol Chem 2009; 284:8023-32.

Schenone S, Brullo C, Musumeci F, Radi M, Botta M. ATP-competitive inhibitors of mTOR: an update. Curr Med Chem 2011; 18:2995-3014.

Wu T J, Wang X, Zhang Y, Meng L, Kerrigan J E, Burley S K, Zheng X F. Identification of a Non-Gatekeeper Hot Spot for Drug-Resistant Mutations in mTOR Kinase. Cell Rep 2015; 11:446-59.

Rodrik-Outmezguine V S, Okaniwa M, Yao Z, Novotny O, McWhirter C, Banaji A, Won H, Wong W, Berger M, de Stanchina E, Barratt D G, Cosulich S, Klinowska T, Rosen N, Shokat K M. Overcoming mTOR resistance mutations with a new-generation mTOR inhibitor. Nature 2016; 534:272-6.

Marcotrigiano J, Gingras A C, Sonenberg N, Burley S K. Cap-dependent translation initiation in eukaryotes is regulated by a molecular mimic of eIF4G. Mol Cell 1999; 3:707-16.

Edwards S R, Wandless T J. The rapamycin-binding domain of the protein kinase mammalian target of rapamycin is a destabilizing domain. J Biol Chem 2007; 282:13395-401.

Sedrani R, Cottens S, Kallen J, Schuler W. Chemical modification of rapamycin: the discovery of SDZ RAD. Transplant Proc 1998; 30:2192-4.

Iiboshi Y, Papst P J, Kawasome H, Hosoi H, Abraham R T, Houghton R I, Terada N. Amino acid-dependent control of p70(s6k). Involvement of tRNA aminoacylation in the regulation. J Biol Chem 1999; 274:1092-9.

Guichard S M, Curwen J, Bihani T, D'Cruz C M, Yates J W, Grondine M, Howard Z, Davies B R, Bigley G, Klinowska T, Pike K G, Pass M, Chresta C M, Polanska U M, McEwen R, Delpuech O, Green S, Cosulich S C. AZD2014, an Inhibitor of mTORC1 and mTORC2, Is Highly Effective in ER+ Breast Cancer When Administered Using Intermittent or Continuous Schedules. Mol Cancer Ther 2015; 14:2508-18.

Hsieh A C, Liu Y, Edlind M P, Ingolia N T, Janes M R, Sher A, Shi E Y, Stumpf C R, Christensen C, Bonham M J, Wang S, Ren P, Martin M, Jessen K, Feldman M E, Weissman J S, Shokat K M, Rommel C, Ruggero D. The translational landscape of mTOR signalling [sic] steers cancer initiation and metastasis. Nature 2012; 485:55-61.

Waxman E A, Giasson B I. A novel, high-efficiency cellular model of fibrillar alpha-synuclein inclusions and the examination of mutations that inhibit amyloid formation. J Neurochem 2010; 113:374-388.

What is claimed is:

1. A method of determining the kinase activity of a full length mTOR variant in a cell, comprising the steps of:
   a. preparing a cDNA of a mTOR variant, said mTOR variant is suspected of having an altered kinase activity relative to a wild-type mTOR;
   b. preparing a cDNA of wild-type mTOR;
   c. providing a first and second cell, said first and second cells having a first construct comprising cDNA selected from the group consisting of cDNA encoding 4E-BP1 protein and cDNA encoding 4E-BP2 protein, said cDNA in the first construct is linked at its N-terminus to a first portion of a luciferase gene, and a second construct having a cDNA of SEQ ID. NO. 1,
      wherein when the protein products of said first construct and said second construct are expressed they interact to form a complex which generates a light emission upon addition of a luciferase substrate;
   d. transfecting said mTOR variant prepared in step a into the first cell provided in step c;
   e. transfecting said wild-type cDNA prepared in step b into the second cell provided in step c;
   f. measuring the light emission in said transfected cell having said mTOR variant in step d and said transfected cell having wild-type mTOR in step e; and
   g. determining if there is an increase or decrease in kinase activity as evidenced by a decrease or increase, respectively, in light emission in said cell transfected with said mTOR variant as compared to that in said cell transfected with said wild-type mTOR.

2. The method of claim 1, wherein said mTOR variant is obtained from a biological sample of a patient.

3. The method of claim 1, wherein said cDNA of the mTOR variant and the cDNA of the wild-type mTOR are transiently transfected and said first and second constructs are stably transfected or transiently transfected.

4. The method of claim 1, wherein said first and second cell is a HEK293 cell or said first and second cell is a MCF-7 cell.

5. A method of determining the kinase activity of mTOR variant in a cell, comprising the steps of:
   a. preparing a cDNA of a mTOR variant, said mTOR variant is suspected of having an altered kinase activity relative to a wild-type mTOR;
   b. preparing a cDNA of wild-type mTOR;
   c. providing a first and second cell, said first and second cells having a first construct comprising cDNA selected from the group consisting of SEQ. ID. NO: 2 and SEQ. ID. NO: 3, and a second construct having cDNA of SEQ. ID. NO: 1, wherein when the protein products of said first construct and said second construct are expressed they interact to form a complex which generates a light emission upon addition of a luciferase substrate;
   d. transfecting said mTOR variant prepared in step a into the first cell provided in step c;
   e. transfecting said wild-type cDNA prepared in step b into the second cell provided in step c;
   f. measuring the light emission in said transfected cell having said mTOR variant in step d and said transfected cell having wild-type mTOR in step e; and
   g. determining if there is an increase or decrease in kinase activity as evidence by a decrease or increase, respectively, in light emission in said cell transfected with said mTOR variant as compared to that in said cell transfected with said wild-type mTOR.

6. A method of determining whether a tumor cell is sensitive to treatment with rapamycin or a rapalog, comprising the steps of:
   a. obtaining a tumor cell;
   b. transfecting into said tumor cell: a first construct comprising a cDNA selected from the group consisting of cDNA encoding 4E-BP1 protein and cDNA encoding 4E-BP2 protein, said cDNA in the first construct is linked at its N-terminus to a first portion of a luciferase gene, and a second construct having a cDNA of SEQ. ID. NO: 1, wherein when the protein products of said first construct and said second construct are expressed they interact to form a complex which generates a light emission upon addition of a luciferase substrate;
c. exposing said transfected cell to rapamycin or a rapalog;
d. repeating steps a and b, then exposing said cell so transfected to a vehicle; and
e. determining whether said tumor cell is sensitive to treatment with said rapamycin or a rapalog by measuring an increase in light emission relative that of said vehicle.

7. The method of claim 6, wherein said tumor cell is a breast tumor cell, a kidney tumor cell, a liver tumor cell, a leukocyte tumor cell, a brain tumor cell, or a lung tumor cell.

8. The method of claim 6, wherein said tumor cell is a breast tumor cell or a kidney tumor cell.

9. The method of claim 6, wherein said rapalog is everolimus.

10. A method of determining whether a tumor cell is sensitive to treatment with rapamycin or a rapalog, comprising the steps of:
a. obtaining a tumor cell;
b. transfecting into said tumor cell with: a first construct having a cDNA selected from the group consisting of SEQ. ID. NO: 2 and SEQ. ID. NO: 3; and a second construct having a cDNA of SEQ. ID. NO: 1,
wherein when the protein products of said first construct and said second construct are expressed they interact to form a complex which generates a light emission upon addition of a luciferase substrate;
c. exposing said transfected cell to rapamycin or a rapalog;
d. repeating steps a and b, then exposing said cell so transfected to a vehicle; and
e. determining whether said tumor cell is sensitive to treatment with said rapamycin or a rapalog by measuring an increase in light emission relative that of said vehicle.

11. A method of determining whether a compound inhibits mTOR protein activity a cell, comprising the steps of:
a. providing a cell, said cell having:
i. a genomic modification of at least one gene selected from the group consisting of EIF4EBP1 and EIF4EBP2; and
ii. a first construct comprising a cDNA selected from the group consisting of cDNA encoding 4E-BP1 protein and cDNA encoding 4E-BP2 protein, said cDNA in the first construct is linked at its N-terminus to a first portion of a luciferase gene, and a second construct having a cDNA of SEQ. ID. No. 1,
wherein when the protein products of said first construct and said second construct are expressed they interact to form a complex which generates a light emission upon addition of a luciferase substrate;
b. exposing said cell to a compound;
c. repeating step a, then exposing the cell to a vehicle;
d. measuring the light emissions in said exposed cell after step b and step c;
e determining whether said compound inhibits mTOR activity in said cell as indicated by an increase in said measured light emission relative that of the cell exposed to a vehicle.

12. The method of claim 11, wherein said cell is a HEK239 or a MCF-7.

13. The method of claim 11, wherein said cell is a HEK239.

14. A method of determining whether a compound inhibits mTOR activity in a cell, comprising the steps of:
a. providing a cell, said cell having:
i. a genomic modification of at least one gene selected from the group consisting of EIF4EBP1 and EIF4EBP2; and
ii. a first construct having a cDNA selected from the group consisting of SEQ. ID. NO: 2 and SEQ. ID. NO: 3, and a second construct having a cDNA of SEQ. ID. NO: 1,
wherein when the protein products of said first construct and said second construct are expressed they interact to form a complex which generates a light emission upon addition of a luciferase substrate;
b. exposing said cell to a compound;
c. repeating step a, then exposing the cell to a vehicle;
d. measuring the light emissions in said exposed cell after step b and step c;
e. determining whether said compound inhibits mTOR activity in said cell as evidenced by an increase in said measured light emission relative that of the cell exposed to a vehicle.

15. A method of determining whether a 4E-BP1 variant or a 4E-BP2 variant is sensitive to treatment with a mTOR inhibitor in a cell, comprising the steps of:
a. preparing a first construct comprising a cDNA selected from the group consisting of cDNA encoding a 4E-BP1 variant protein and cDNA encoding a 4E-BP2 variant protein, said cDNA in the first construct is linked at its N-terminus to a first portion of a luciferase gene, and preparing a second construct comprising a cDNA encoding eIF4E protein, said cDNA of the second construct is linked at its N-terminus to a second portion of a luciferase gene;
b. transfecting said first construct and said second construct into a mammalian cell, wherein when the protein products of said first construct and said second construct are expressed they interact to form a complex which generates a light emission upon addition of a luciferase substrate;
c. exposing said cell to a mTOR inhibitor;
d. repeating steps a and b, then exposing the cell so transfected to a vehicle; and
e. determining whether said 4E-BP1 variant protein or said 4E-BP2 variant protein is sensitive to treatment with said mTOR inhibitor by measuring the generated light emissions,
wherein an increase in light emission of the cell exposed to the mTOR inhibitor relative to that of the cell exposed to the vehicle is indicative of 4E-BP1 variant protein or 4E-BP2 variant protein sensitivity to treatment,
f. wherein genomic modification is carried out using CRISPR/Cas9 technology.

16. The method of claim 15, wherein said 4E-BP1 variant or said 4E-BP2 variant is obtained from a biological sample of a patient.

17. The method of claim 15, wherein said mTOR inhibitor is rapamycin.

18. A method of determining whether a 4E-BP variant is capable of functioning in its capacity of binding eIF4E in a cell, comprising the steps of:
a. preparing a first construct comprising a cDNA of a 4E-BP variant, said 4E-BP variant containing at least one mutation as compared to wild-type 4E-BP, wherein said cDNA in the first construct is linked at its N-terminus to a first portion of a luciferase gene, and preparing a second construct having a cDNA of SEQ. ID. NO. 1;
b. transfecting said first construct and said second construct into a first mammalian cell,
wherein when the protein products of said first construct and said second construct are expressed they interact to form a complex which generates a light emission upon addition of a luciferase substrate;
c. repeating steps a and b except that said first construct contains cDNA of wild-type 4E-BP and transfecting is into a second mammalian cell;
d. determining whether said 4E-BP variant is capable of functioning in its capacity of binding eIF4E by comparing the light signal generated by said cell transfected with 4E-BP variant compared to that of the cell transfected with wild-type 4E-BP.

19. The method of claim 18, wherein said 4E-BP variant is obtained from a biological sample of a patient.

20. The method of claim 18, wherein said cell contains genomic modification of EIF4EBP1 or EIF4EBP2.

21. A cell line, said cell line comprising cells transfected with:
a. a first construct comprising a first cDNA selected from the group consisting of cDNA encoding 4E-BP1 protein and cDNA encoding 4E-BP2 protein, said first cDNA is linked at its N-terminus to a first portion of a luciferase gene, said first construct having cDNA selected from the group consisting of SEQ. ID. NO: 2 or SEQ. ID. NO; 3;
b. a second construct comprising a second cDNA encoding eIF4E protein, said second cDNA is linked at its N-terminus to a second portion of a luciferase gene, said second construct having cDNA of SEQ. ID. NO: 1,
wherein when the protein products of said first construct and said second construct interact a complex is formed which generates a light emission in the presence of a luciferase substrate.

22. The cell line of claim 21 further comprising a genetic modification of EIF4EBP1, EIF4EBP2, or both.

23. The cell line of claim 21, wherein the parent cells are HEK293, MCF-7, Hela, HT29, A431, MIR 32, K562, U937, MDA-MB231, SK-N-BE(2), SH-SY5Y, HL60, CHO, COS-7, S49, Ltk, NG108-15, B35, B50, B104, C6, Jurkat, BHK, Neuro-2a, NIH/3T3, A549, Be2C, SW480, Caco2, THP1, IMR90, HT1080, LnCap, HepG2, PC12, or SKBR3 cells.

24. The cell line of claim 21, wherein the parent cells are HEK293 or MCF-7 cells.

* * * * *